(12) United States Patent
Zhong et al.

(10) Patent No.: US 10,272,098 B2
(45) Date of Patent: Apr. 30, 2019

(54) CHELATED DRUG DELIVERY SYSTEMS

(71) Applicant: Drexel University, Philadelphia, PA (US)

(72) Inventors: Yinghui Zhong, Bala Cynwyd, PA (US); Zhiling Zhang, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 14/773,883

(22) PCT Filed: Mar. 14, 2014

(86) PCT No.: PCT/US2014/027739
§ 371 (c)(1),
(2) Date: Sep. 9, 2015

(87) PCT Pub. No.: WO2014/152790
PCT Pub. Date: Sep. 25, 2014

(65) Prior Publication Data
US 2016/0022707 A1    Jan. 28, 2016

Related U.S. Application Data

(60) Provisional application No. 61/785,228, filed on Mar. 14, 2013.

(51) Int. Cl.
| | | |
|---|---|---|
| *A61K 31/65* | (2006.01) | |
| *A61K 47/69* | (2017.01) | |
| *A61K 9/14* | (2006.01) | |
| *A61K 31/704* | (2006.01) | |
| *A61K 9/00* | (2006.01) | |
| *A61K 9/06* | (2006.01) | |
| *A61K 31/496* | (2006.01) | |
| *A61K 47/60* | (2017.01) | |
| *A61K 47/52* | (2017.01) | |
| *A61K 47/58* | (2017.01) | |
| *A61K 47/59* | (2017.01) | |
| *A61K 47/61* | (2017.01) | |
| *A61K 47/64* | (2017.01) | |

(52) U.S. Cl.
CPC ............ *A61K 31/65* (2013.01); *A61K 9/0019* (2013.01); *A61K 9/0024* (2013.01); *A61K 9/06* (2013.01); *A61K 9/141* (2013.01); *A61K 31/496* (2013.01); *A61K 31/704* (2013.01); *A61K 47/52* (2017.08); *A61K 47/58* (2017.08); *A61K 47/59* (2017.08); *A61K 47/60* (2017.08); *A61K 47/61* (2017.08); *A61K 47/645* (2017.08); *A61K 47/6903* (2017.08); *A61K 47/6921* (2017.08); *A61K 47/6927* (2017.08)

(58) Field of Classification Search
None
See application file for complete search history.

(56) References Cited

U.S. PATENT DOCUMENTS

| | | | |
|---|---|---|---|
| 4,039,285 A * | 8/1977 | Teipel | G01N 31/02 |
| | | | 436/13 |
| 5,932,248 A | 8/1999 | Chen et al. | |
| 6,277,393 B1 | 8/2001 | Yrjänheikki et al. | |
| 6,566,350 B2 | 5/2003 | Ono et al. | |
| 7,744,644 B2 | 6/2010 | Weber et al. | |
| 7,863,258 B1 | 1/2011 | Sung et al. | |
| 7,863,259 B1 | 1/2011 | Sung et al. | |
| 7,871,988 B1 | 1/2011 | Sung et al. | |
| 7,871,989 B1 | 1/2011 | Sung et al. | |
| 7,879,312 B1 | 2/2011 | Sung et al. | |
| 7,897,585 B1 | 3/2011 | Sung et al. | |
| 7,919,072 B1 | 4/2011 | Sung et al. | |
| 7,998,458 B2 | 8/2011 | Sung et al. | |
| 8,007,768 B1 | 8/2011 | Sung et al. | |
| 8,048,404 B1 | 11/2011 | Sung et al. | |
| 8,048,453 B1 | 11/2011 | Sung et al. | |
| 2002/0155999 A1* | 10/2002 | Han | C07H 15/252 |
| | | | 514/1.3 |
| 2005/0026218 A1* | 2/2005 | Malek | C07H 21/04 |
| | | | 435/7.1 |
| 2005/0281797 A1* | 12/2005 | Gong | A61K 31/704 |
| | | | 424/94.3 |
| 2007/0110804 A1* | 5/2007 | Royer | A61K 9/06 |
| | | | 424/468 |
| 2007/0203079 A1* | 8/2007 | Caldwell | A61K 31/00 |
| | | | 514/27 |
| 2010/0129448 A1 | 5/2010 | Talton et al. | |
| 2010/0196481 A1 | 8/2010 | Pritchard et al. | |
| 2010/0285001 A1* | 11/2010 | Land | C12Q 1/6886 |
| | | | 424/130.1 |
| 2010/0324110 A1 | 12/2010 | Alur et al. | |
| 2012/0263721 A1* | 10/2012 | Stagg | A61K 39/39558 |
| | | | 424/135.1 |
| 2014/0242188 A1 | 8/2014 | Myntti et al. | |

OTHER PUBLICATIONS

Janes, Chitosan nanoparticles as delivery systems for doxorubicin, Journal of Controlled Release 73 (2001) 255-267.*

Mitra, Tumour targeted delivery of encapsulated dextran—doxorubicin conjugate using chitosan nanoparticles as carrier, Journal of Controlled Release 74 (2001) 317-323.*

Gewirtz, A Critical Evaluation of the Mechanisms of Action Proposed for the Antitumor Effects of the Anthracycline Antibiotics Adriamycin and Daunorubicin, Biochemical Pharmacology, vol. 57, pp. 727-741, 1999.*

(Continued)

*Primary Examiner* — Jennifer A Berrios
(74) *Attorney, Agent, or Firm* — Saul Ewing Arnstein & Lehr LLP; Kathryn Doyle; Domingos J. Silva

(57) ABSTRACT

The present invention provides drug delivery compositions that allow for immediate and/or sustained release of a therapeutic agent contained within the system. The present invention also provides drug delivery compositions that preserve the stability of the therapeutic agent contained within during the sustained release. The present invention further provides a method of treating, ameliorating, or preventing an inflammation-related disease or disorder in a subject using the compositions of the invention.

15 Claims, 34 Drawing Sheets

(56) References Cited

OTHER PUBLICATIONS

Holmkvista, Hydrophobic ion pairing of a minocycline/Ca2+/AOT complex for preparation of drug-loaded PLGA nanoparticles with improved sustained release, International Journal of Pharmaceutics 499 (2016) 351-357 (Year: 2016).*

Wallis et al., Interaction of Norfloxacin with Divalent and Trivalent Pharmaceutical Cations. In Vitro Complexation and in Vivo Pharmacokinetic Studies in the Dog, Journal of Pharmaceutical Sciences /vol. 85, No. 8, Aug. 1996 (Year: 1996).*

PCT International Search Report and Written Opinion for PCT International Application No. PCT/US2014/027739 dated Aug. 22, 2014.

Hannah, "Written Preliminary Exam—Dr. Maren Roman", Retrieved Jul. 29, 2014. Retrieved from the Internet <URL: http://filebox.vt.edu/s/ssegnere/SHannah%20-%20RomanPrelimResponse.doc>, [Online] Oct. 2007.

Hyun, "Clinical and experimental advances in regeneration of spinal cord injury", J Tissue Eng. 2010, Article ID 650857, Nov. 2, 2010, 1-20.

Kang, et al., "Thermosensitive Polymer-based Hydrogel Mixed with the Anti-inflammatory Agent Minocycline Induces Axonal Regeneration in Hemisected Spinal Cord", Macromolecular Research 18(4), 2010, 399-403.

Perale, et al., "Hydrogels in spinal cord injury repair strategies", ACS Chem Neurosci. 2(7), Jul. 20, 2011, 336-345.

Shoichet, et al., "Strategies for Regeneration and Repair in the Injured Central Nervous System." Indwelling Neural Implants: Strategies for Contending with the in Vivo Environment. Boca Raton (FL): CRC Press/ Taylor & Francis; Chapter 8, 2008.

* cited by examiner

Fig. 3
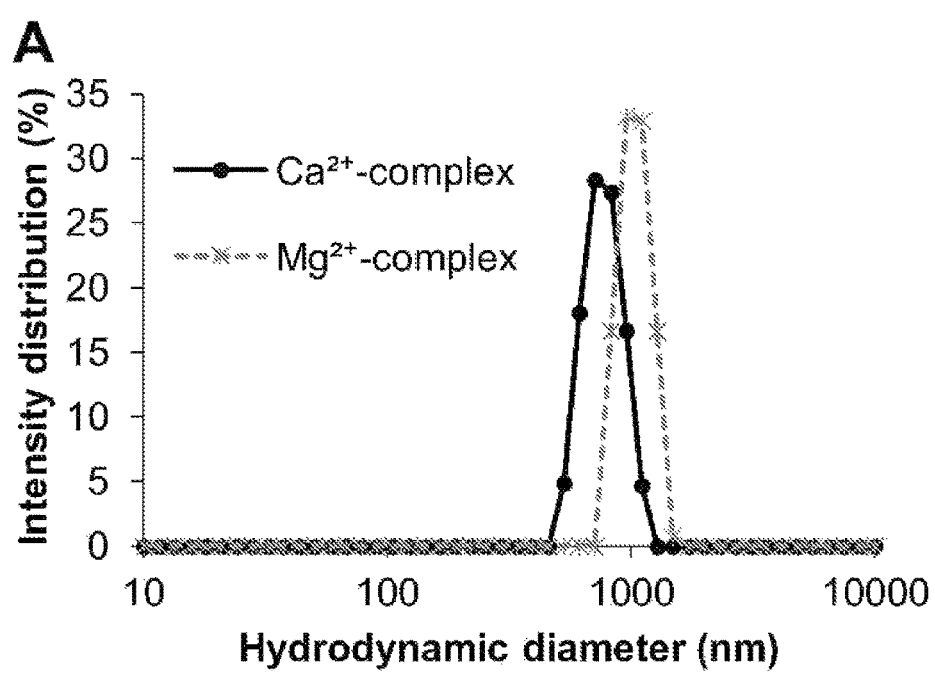
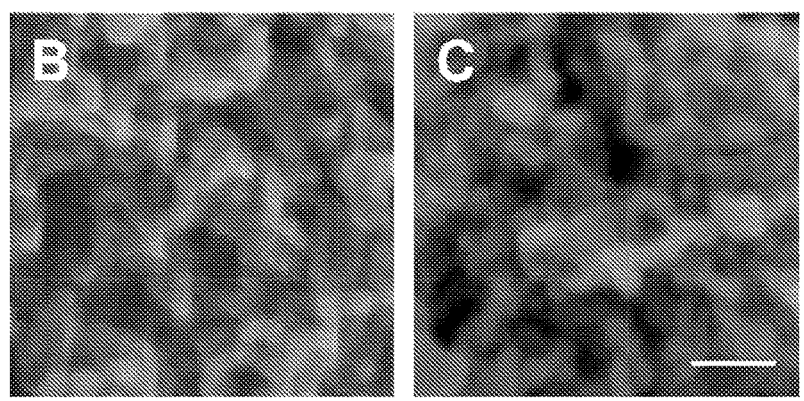

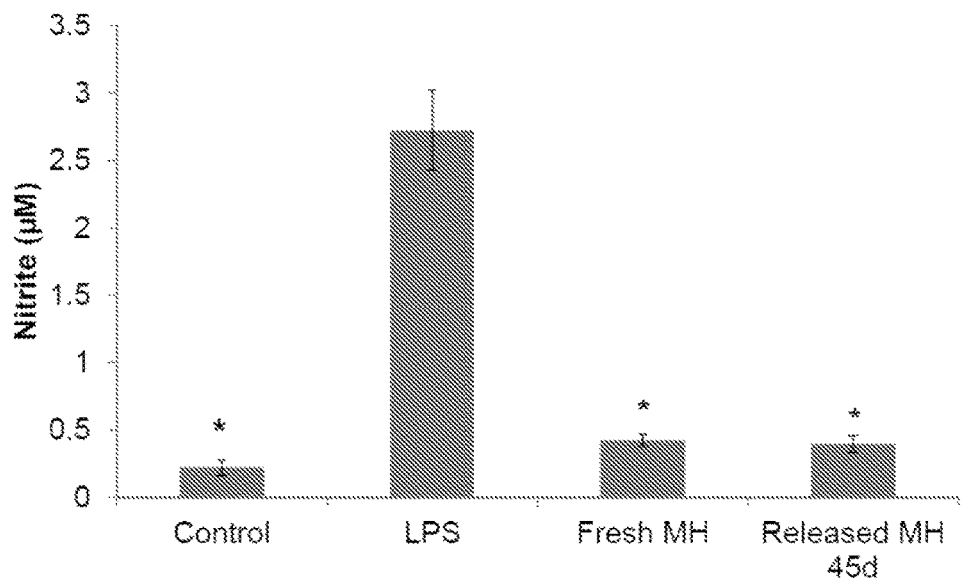
Fig. 26
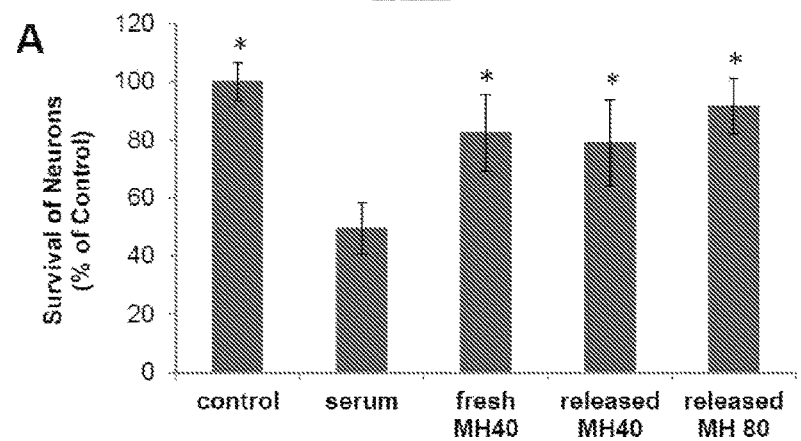
Fig. 27
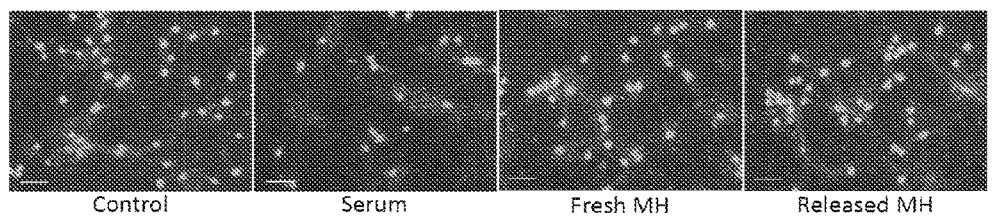

Fig. 33
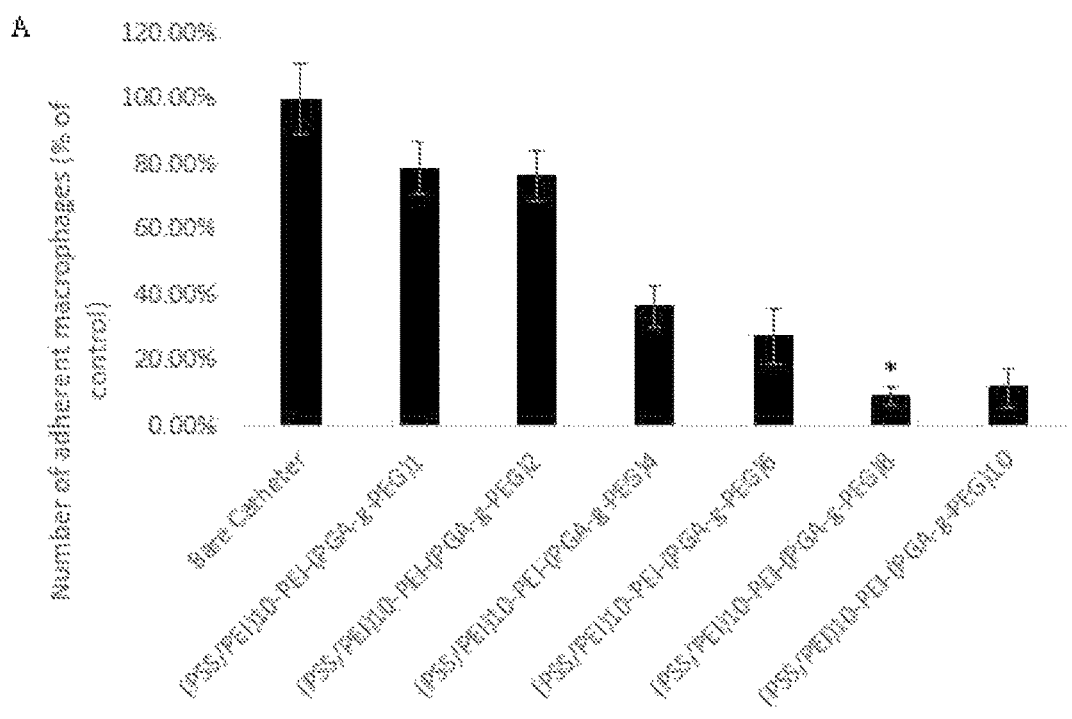
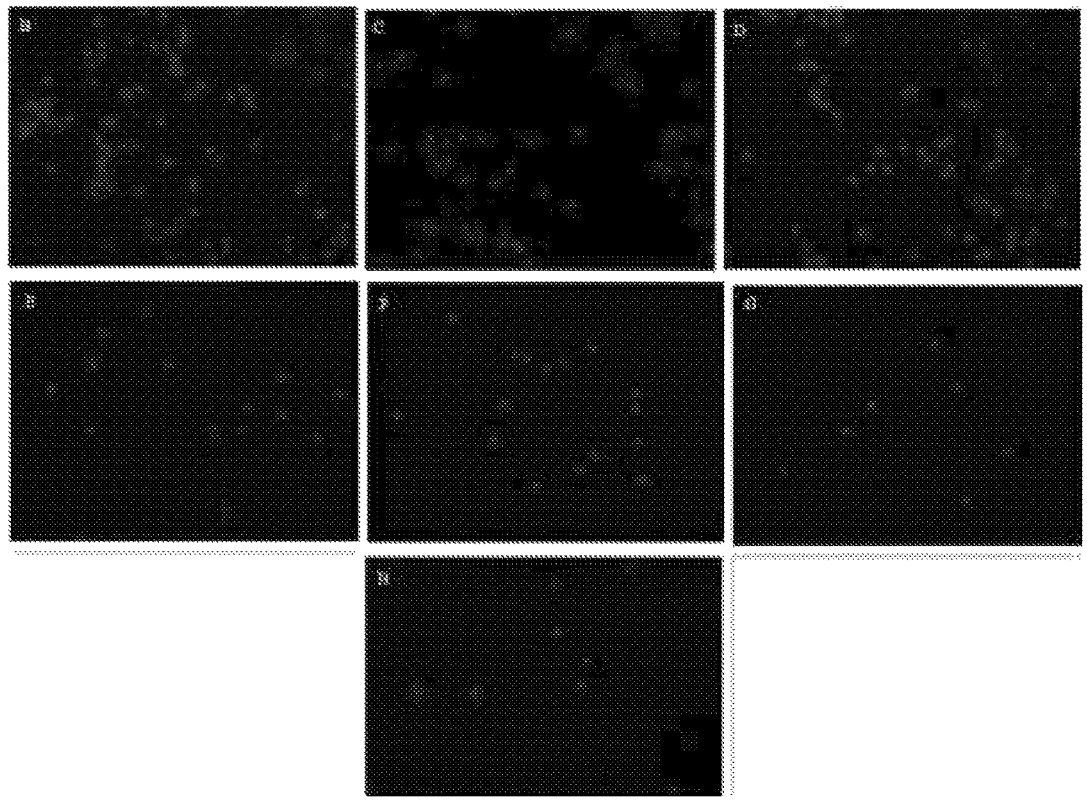

E. coli (Uncoated)  E. coli (Coated)

A. Baumannii (Uncoated)  A. Baumannii (coated)

US 10,272,098 B2

CHELATED DRUG DELIVERY SYSTEMS

CROSS-REFERENCE TO RELATED APPLICATIONS

The present application is a 35 U.S.C. § 371 national phase application from, and claims priority to, International Application No. PCT/US2014/027739, filed Mar. 14, 2014, and published under PCT Article 21(2) in English, which claims priority under 35 U.S.C. § 119(e) to U.S. Provisional Application No. 61/785,228, filed Mar. 14, 2013, all of which applications are incorporated herein by reference in their entireties.

STATEMENT REGARDING FEDERALLY SPONSORED RESEARCH OR DEVELOPMENT

This invention was made with government support under Contract No. R21 NS084379 awarded by the National Institutes of Health. The government has certain rights in the invention.

BACKGROUND OF THE INVENTION

With the proliferation of biomedical implants, there has been an interest in modifying the implant's surface with biocompatible materials, in order to allow for its integration with local tissue (Hetrick et al., 2006, Chem. Soc. Rev. 35:780-789). The implant surface should be biocompatible and/or bioactive, have the ability to prevent or reduce local inflammatory responses, and ideally prevent post-operation infection (Hezi-Yamit et al., 2009, J. Biomed. Mater. Res. A 90:133-141).

Neural prostheses generally make use of electrodes. Stimulating electrodes are widely used in cochlear implants and deep brain stimulation (DBS) to restore hearing and alleviate the symptoms of Parkinson's disease (PD). Recording electrodes are used to restore movement in patients paralyzed by head trauma, spinal cord trauma or neurodegenerative diseases, by reading neural signals from the brain and translating them into movement commands.

Infection and inflammation may affect the longevity and even cause failure of the electrodes. The infection rate for DBS is 9-10% (Williams et al., 2010, Lancet Neurol. 9:581-591; Weaver et al., 2009, JAMA 301:63-73). Recording electrodes normally fail weeks to months after implantation, mostly due to inflammation and resultant neuronal loss. Glial scar encapsulation, a typical inflammatory response of the tissue in the central nervous system, increases the stimulation threshold, with detrimental effects on both the tissue and the electrode (Winter et al., 2007, J. Biomed. Mater. Res. B Appl. Biomater. 81:551-563). Poor performance of recording electrodes presents an obstacle for the development of next generation DBS, wherein closed-loop would integrates the neural signal recording system as feedback so that the stimulus is delivered in reaction to the ongoing brain activity.

Approximately 1 million Americans live with PD, and 60,000 are diagnosed with PD each year. The economic impact of PD in the U.S. is estimated at $23 billion/year. There is no known cure or disease regression treatment for PD, and current treatments (DBS or medication) only manage symptoms. DBS, or DBS plus medication, is more effective than medication alone in improving patient self-reported quality of life (Williams et al., 2010, Lancet Neurol. 9:581-591; Weaver et al., 2009, JAMA 301:63-73). Recording electrodes could in principle be used for a paralyzed PD patient to regain movement functions.

Minocycline hydrochloride (MH) is a small molecule tetracycline antibiotic commonly used to treat inflammation and infection. MH is not only a potent neuroprotectant, but also a BMP (bone morphogenic protein) inhibitor, reducing hypertrophic scaring and even preventing restenosis after stent implantation (Hua et al., 2006, Brain Research 1090: 172-181; Yrjanheikki et al., 1999, Proc. Natl. Acad. Sci. USA 96:13496-13500; Henry et al., 2007, Plast. Reconstr. Surg. 120:80-88; Pinney et al., 2003, J. Cardiovasc. Pharm. 42:469-476). MH has shown remarkable therapeutic potential in a variety of neural injuries and neurological disorders, including traumatic brain injury (TBI), spinal cord injury (SCI), stroke, intracerebral hemorrhage (ICH), Parkinson's disease, Alzheimer's disease, multiple sclerosis, and amyotrophic lateral sclerosis (ALS), due to its anti-inflammatory, anti-oxidant, and anti-apoptotic properties.

MH, with its neuroprotective and anti-inflammatory properties, has great potential to reduce inflammation and neuronal loss around implanted neural electrodes, and improve their functionality and longevity. Local release of MH from coatings on neural prostheses would expose tissue at the implantation site to high local concentrations of MH (not achievable by systemic administration) and avoid the deleterious side effects from systemic exposure.

Unfortunately, use of MH is limited because systemic administration of a safe dose of MH cannot achieve sufficiently high local concentration of MH to be neuroprotective or inhibit neointima formation. For example, systemic administration of 200 mg of MH daily (equivalent to 3 mg/kg, standard human dose) results in only about 0.5 µg/mL MH in the cerebrospinal fluid (CSF) in human subjects (Maier et al., 2007, Neurobiol. Dis. 25:514-525), which is far below the level required for neuroprotection (10-75 µg/mL) (Hua et al., 2006, Brain Research 1090:172-181; Fagan et al., 2010, Stroke 41:469-476). A dosage of 70-100 mg/kg/d of MH is required for reducing neointima formation in rats; however this dosage is much higher than the standard human dosage of 3 mg/kg/d (equivalent to 200 mg/daily) and is accompanied by toxicity (Pinney et al., 2003, J Cardiovasc Pharmacol. 42:469-476).

Systemic administration of MH for 1-6 days reduces secondary injury and improves functional recovery in SCI animal models (Lee et al., 2003, J. Neurotrauma 20:1017-1027; Stirling et al., 2004, J. Neurosci. 24:2182-2190; Teng et al., 2004, Proc. Natl. Acad. Sci. USA 101:3071-3076; Wells et al., 2003, Brain 126:1628-1637; Yune et al., 2007, J. Neurosci. 27:7751-7761). However, the doses of MH used in these studies (45-90 mg/kg) were much higher than the standard human dose (3 mg/kg) (Xu et al., 2004, BMC Neurol. 4:7). Likewise, oral administration of MH increased the quality and longevity of chronic neural recordings and post-cochlear implants (Rennaker et al., 2007, J. Neural Eng. 4:L1-5), but only at doses far above the maximum normal dose. Taken together, these facts indicate that systemic administration of MH cannot achieve high local concentrations sufficient for neuroprotection, scar prevention, and hyperplasia minimization. In particular, local delivery of MH may expose neural cells at the injury site to high drug concentration, while avoiding the deleterious side effects from systemic exposure. Further, sustained delivery may render feasible long-term treatments for maximum efficacy.

Minocycline is unstable in aqueous solution, especially at body temperature. Therefore, there is a need to develop a drug delivery system capable of sustained release and stabilization of minocycline. Sustained release of MH using solid macroparticles or nanoparticles has been attempted. Solid macro- or nanoparticles may be fabricated using, for example, double emulsion to make hydrophobic particles, or precipitation of oppositely charged polyelectrolytes by electrostatic interactions. The former mechanism was used to fabricate PLGA macrospheres, while the latter mechanism was used to create polyion complex (PIC) micelles (Soliman et al., 2010, Macromol. Biosci. 10:278-288). However, the acidic degradation products of PLGA can reduce local tissue pH and subsequently elicit host inflammation (Liu H, et al., 2006, Int'l J. Nanomed. 1:541), and this may exacerbate secondary injury. In addition, PLGA microspheres or nanoparticles have very low entrapment efficiency for hydrophilic drugs such as MH. The highest entrapment efficiency for MH reported so far is only 1.92% (Kashi T, et al., Int'l J. Nanomed. 7:221-234).

When attempting long-term delivery as used in MH treatment, release kinetics are paramount. Zero-order release (i.e., a drug release rate independent of time) enables drug delivery to be matched with the local drug requirement and is useful in the area of stent design (Hetrick et al., 2006, Chem. Soc. Rev. 35:780-789; Hezi-Yamit et al., 2009, J. Biomed. Mater. Res. A 90:133-141). Short-term super-clinical dosages rapidly reach clinically relevant dosages and can control acute local response to the newly inserted stent, while long-term release prevents chronic responses. Similar "burst" doses of MH prevent damage caused by brain lesion (Hua et al., 2006, Brain Research 1090:172-181). Depending on the clinical usage and local tissue response, a tunable release kinetic may allow for optimal chronic delivery dosing that enhances efficacy and reduces side effects.

There is a need in the art for a novel drug delivery system that affords sustained release of a therapeutic agent directly to a target site in a subject, thereby circumventing the need for systemic administration of the therapeutic agent. There is also a need in the art for compositions and methods that effectively reduce infection and inflammation associated to a neural prosthesis implanted in a subject, thus improving prosthetic longevity and reducing infection rate in the subject. The present invention addresses this unmet need in the art.

BRIEF SUMMARY OF THE INVENTION

In one aspect, the invention provides a composition comprising a therapeutic agent or a salt thereof, a polyelectrolyte and a polyvalent metal ion, wherein the therapeutic agent chelates at least a fraction of the polyvalent metal ion, and wherein the polyelectrolyte comprises a polyanion, a predominantly polyanionic polyampholyte, or any combinations thereof.

In another aspect, the invention provides a particle comprising a composition of the invention.

In yet another aspect, the invention provides a biocompatible hydrogel comprising at least one selected from the group consisting of a composition of the invention and a particle of the invention.

In yet another aspect, the invention provides a biocompatible layer-by-layer (LbL) assembly comprising two or more overlaid multilayer units, wherein each multilayer unit independently comprises a composition comprising a therapeutic agent or a salt thereof, a polyelectrolyte, a polyvalent metal ion, and optionally a polycation; wherein the polyelectrolyte comprises a polyanion, a predominantly polyanionic polyampholyte, or any combinations thereof.

In yet another aspect, the invention provides a method of treating, ameliorating or preventing a disease or disorder in a subject in need thereof, the method comprising administering to the subject a therapeutically effective amount of at least one biocompatible composition selected from the group consisting of: (a) a particle comprising a composition comprising a therapeutic agent or a salt thereof, a polyelectrolyte and a polyvalent metal ion; (b) a hydrogel comprising a composition comprising a therapeutic agent or a salt thereof, a polyelectrolyte, and a polyvalent metal ion; and, (c) a layer-by-layer (LbL) assembly comprising a composition comprising a therapeutic agent or a salt thereof, a polyelectrolyte, and a polyvalent metal ion; wherein the therapeutic agent chelates at least a fraction of the polyvalent metal ion; wherein the polyelectrolyte comprises a polyanion, a predominantly polyanionic polyampholyte, or any combinations thereof, and wherein the composition is essentially free of a polycation or further comprises a polycation.

In yet another aspect, the invention provides a technological device, wherein the device is used for insertion, implantation or injection into a subject, wherein at least a portion of the surface of the device to be inserted, implanted or injected into the subject is coated with a layer-by-layer (LbL) assembly comprising a composition comprising a therapeutic agent or a salt thereof, a polyelectrolyte, and a polyvalent metal ion, wherein the therapeutic agent chelates at least a fraction of the polyvalent metal ion; wherein the polyelectrolyte comprises a polyanion, a predominantly polyanionic polyampholyte, or any combinations thereof; and wherein the composition is essentially free of a polycation or further comprises a polycation.

In yet another aspect, the invention provides a method of derivatizing a technological device, wherein the device is used for insertion, implantation or injection into a subject, wherein the method comprises coating at least a portion of the surface of the device to be inserted, implanted or injected into the subject with a layer-by-layer (LbL) assembly comprising a composition comprising a therapeutic agent or a salt thereof, a polyelectrolyte, and a polyvalent metal ion, wherein the therapeutic agent chelates at least a fraction of the polyvalent metal ion; wherein the polyelectrolyte comprises a polyanion, a predominantly polyanionic polyampholyte, or any combinations thereof; and wherein the composition is essentially free of a polycation or further comprises a polycation.

In certain embodiments, the composition is essentially free of a polycation. In other embodiments, the composition further comprises a polycation. In yet other embodiments, the polycation comprises chitosan, poly(L-lysine), polyethyleneimine (PEI), gelatin type A (GA), protamine, multiple bilayers of PEI/polystyrene sulfonate (PSS), or any combinations thereof.

In certain embodiments, the polyvalent metal ion is divalent, trivalent or tetravalent. In other embodiments, the divalent metal ion comprises $Ca^{2+}$, $Mg^{2+}$, $Ba^{2+}$, $Be^{2+}$, $Cd^{2+}$, $Hg^{2+}$, $Pb^{2+}$, $Zn^{2+}$, $Fe^{2+}$, $Ni^{2+}$, $Cu^{2+}$, $Sn^{2+}$, or any combinations thereof.

In certain embodiments, the polyelectrolyte comprises dextran sulfate, heparin, chondroitin sulfate, hyaluronic acid, alginate, alginate sulfate, polyacrylic acid, poly(methyl methacrylate) (PMMA), poly(vinylsulfonic acid) (PVSA), poly(L-aspartic acid), poly(L-glutamic acid), poly(L-aspartic acid)-grafted-poly(ethylene glycol) (PAA-g-PEG), poly (L-glutamic acid)-grafted-poly(ethylene glycol) (PGA-g-

PEG), poly(sodium 4-styrenesulfonate) (PSS), dermatan sulfate, carboxymethyl cellulose (CMC), or any combinations thereof.

In certain embodiments, the therapeutic agent is selected from the group consisting of an analgesic, anesthetic, antifungal, antibiotic, anti-inflammatory, anthelmintic, antidote, antiemetic, antihistamine, antihypertensive, antimalarial, antimicrobial, antipsychotic, antipyretic, antiseptic, antiarthritic, antituberculotic, antitussive, antiviral, cardioactive drug, cathartic, chemotherapeutic agent, colored or fluorescent imaging agent, corticoid, antidepressant, depressant, diagnostic aid, diuretic, enzyme, expectorant, hormone, hypnotic, mineral, nutritional supplement, parasympathomimetic, potassium supplement, radiation sensitizer, radioisotope, sedative, sulfonamide, stimulant, sympathomimetic, tranquilizer, urinary anti-infective, vasoconstrictor, vasodilator, vitamin, xanthine derivative, small organic molecule, naturally isolated entity or its analogs, organometallic agent, chelated metal or metal salt, peptide-based drug, peptidic or non-peptidic receptor targeting or binding agent, and any combinations thereof. In other embodiments, the therapeutic agent is selected from the group consisting of a tetracycline antibiotic, quinolone, anthracenedione, anthracyclin, statin, chemotherapeutic drug, and any combinations thereof. In yet other embodiments, the therapeutic agent is minocycline, tetracycline, ciprofloxacin, doxorubicin, a salt thereof, or any combinations thereof. In yet other embodiments, the therapeutic agent is minocycline hydrochloride.

In certain embodiments, the particle comprises a nanoparticle. In other embodiments, the hydrogel is essentially free of a polycation. In yet other embodiments, the hydrogel further comprises a polycation. In yet other embodiments, the hydrogel further comprises agarose, alginate, alginate sulfate, dextran sulfate, hyaluronan, chitosan, collagen, pectin, carrageenan, gelatin, or any combinations thereof. In yet other embodiments, the therapeutic agent or salt thereof is essentially free of at least one decomposition or denaturating product thereof. In yet other embodiments, the hydrogel affords at least one selected from the group consisting of sustained release and rapid release of the therapeutic agent or salt thereof. In yet other embodiments, the therapeutic agent is doxorubicin and the polyelectrolyte is dextran sulfate. In yet other embodiments, the ratio of doxorubicin to dextran sulfate is about 1:1 (w/w).

In certain embodiments, each multilayer unit is independently a bilayer or trilayer unit. In other embodiments, at least one multilayer unit comprises a layer of dextran sulfate and a layer of gelatin type A. In yet other embodiments, at least one multilayer unit comprises a layer of dextran sulfate and a layer of alginate or alginate sulfate. In yet other embodiments, at least one multilayer unit comprises a layer of polyelectrolyte, a layer of the therapeutic agent or salt thereof, and a layer of polycation, wherein the polyvalent metal ion is present in the layer of polyelectrolyte; wherein the polyvalent metal ion is independently optionally present in the layer of the therapeutic agent or salt thereof and in the layer of polycation; and wherein the therapeutic agent or salt thereof chelates the polyvalent metal ion.

In certain embodiments, the assembly comprises between about 2 and about 24 overlaid multilayer units. In other embodiments, the assembly affords sustained release of the therapeutic agent or salt thereof. In yet other embodiments, the thickness of the two or more overlaid multilayer units is equal to or less than about 10 µm.

In certain embodiments, the at least one biocompatible composition is inserted, implanted or injected in the subject. In other embodiments, the at least one biocompatible composition is fluid at the temperature used for insertion, implantation or injection, and is a gel at the subject's body temperature.

In certain embodiments, the disease or disorder is selected from the group comprising chronic inflammation, autoimmune disease, spinal cord injury, stroke, myocardial infarction, chronic heart failure, diabetes, circulatory shock, chronic inflammatory disease, cancer, neurodegenerative disorder, traumatic brain injury, severing of a peripheral nerve, nerve root impingement, traumatic injury, and any combinations thereof. In other embodiments, the disease comprises inflammation. In yet other embodiments, the therapeutic agent comprises minocycline. In yet other embodiments, the disease comprises inflammation and the therapeutic agent comprises minocycline. In yet other embodiments, the disease comprises cancer and the therapeutic agent comprises doxorubicin.

In certain embodiments, the subject is a mammal. In other embodiments, the mammal is human.

In certain embodiments, the device is selected from the group consisting of a medical implant, cosmetic implant, vascular implant, auditory implant, cochlear implants, orthopedic implant, bone plate, screw, joint prosthetic, breast implant, artificial larynx implant, maxillofacial prosthetic, dental implant, pacemaker, cardiac defibrillator, penile implant, drug pump, drug delivery device, sensors, monitor, neurostimulator, incontinence alleviating device, intraocular lens, water transporting sack, electrolyte transporting sack, glucose transporting sack, oxygen transporting sack, cells replacing a lost or damaged function of the human body, tissues replacing a lost or damaged function of the human body, neural prosthetic, recording electrode, cochlear implant, and any combinations thereof. In other embodiments, the therapeutic agent comprises minocycline, tetracycline, ciprofloxacin, doxorubicin, a salt thereof, or any combinations thereof.

BRIEF DESCRIPTION OF THE DRAWINGS

The following detailed description of preferred embodiments of the invention will be better understood when read in conjunction with the appended drawings. For the purpose of illustrating the invention, illustrated in the drawings are specific embodiments. It should be understood, however, that the invention is not limited to the precise arrangements and instrumentalities of the embodiments illustrated in the drawings.

FIGS. 2A-2D, illustrates the entrapment efficiency of DS and MH in the DS/MH/metal ion complexes. FIG. 2A is a graph illustrating the entrapment efficiency of the DS/MH/$Ca^{2+}$ complexes as a function of $Ca^{2+}$ concentration. FIG. 2B is a graph illustrating the entrapment efficiency of the DS/MH/$Ca^{2+}$ complexes as a function of ratio of DS to MH. FIG. 2C is a graph illustrating the entrapment efficiency of the DS/MH/$Mg^{2+}$ complexes as a function of $Mg^{2+}$ concentration. FIG. 2D is a graph illustrating the entrapment efficiency of the DS/MH/$Mg^{2+}$ complexes as a function of ratio of DS to MH.

FIG. 3, comprising FIGS. 3A-3C, illustrates the size of the DS/MH/metal ion complexes. FIG. 3A is a graph illustrating the measurement of size of the DS/MH/metal ion complexes using dynamic light scattering (DLS). FIGS. 3B-3C illustrate scanning electron microscopy (SEM) images of MH/DS/metal ion complexes under magnification; FIG. 3B, MH/DS/$Ca^{2+}$ complexes; FIG. 3C, MH/DS/$Mg^{2+}$ complexes. Scale bar=100 nm.

FIGS. 4A-4B, illustrates the release profile of MH from the MH/DS/metal ion complex as a function of metal ion concentration; FIG. 4A for $Ca^{2+}$, and FIG. 4B for $Mg^{2+}$.

FIGS. 5A-5B, illustrates the release profile of MH from the MH/DS/metal ion complex as a function of pH; FIG. 5A for MH/DS/$Ca^{2+}$ complexes, and FIG. 5B for MH/DS/$Mg^{2+}$ complexes.

FIGS. 6A-6B, illustrates the antibiofilm activity of MH/DS/metal ion complex. FIG. 6A is a series of images illustrating fluorescent images of *E. coli, S. aureus*, and *A. baumannii* without any treatment, treated with fresh MH, or MH released from $Ca^{2+}$-based or $Mg^{2+}$-based complexes. The cells were stained with "live" SYTO 9 stain (green fluorescence). Biofilm formation was inhibited by MH treatment. Scale bar=20 µm. FIG. 6B is a graph illustrating that XTT assay for quantification of surviving bacteria demonstrates significant antibiofilm activity of fresh MH, as well as MH released from the complexes. * $P<0.05$ compared with untreated control. Data illustrated were average±STD (n=4).

FIG. 7, comprising FIG. 7A is a graph illustrating cell counting assay result of 3T3 fibroblast after 24 hours treatment with MH/DS/$Ca^{2+}$ complexes, MH/DS/$Mg^{2+}$ complexes, or fresh MH. Cells without any treatment were used as controls. No significant difference in bioactivity was observed between the MH released from MH/DS/metal ion complexes and MH released from the control ($P<0.05$ compared with control). FIG. 7B is a graph illustrating nitrite production by macrophages treated with either LPS alone, LPS plus MH released from MH/DS/$Ca^{2+}$ complexes on day 55, LPS plus MH released from MH/DS/$Mg^{2+}$ complexes on day 71, or LPS plus fresh MH. Cells without any treatment were used as control. The level of nitrite was used as an indicator of the amount of nitric oxide (NO) produced by the macrophage induced by LPS. *$P<0.05$ compared with LPS-treated culture. Data illustrated were average±STD (n=3). FIG. 7C is an image of control 3T3 fibroblast cells. FIG. 7D is an image of 3T3 fibroblast cells treated with MH/DS/$Ca^{2+}$ complexes for 24 hours. FIG. 7E is an image of 3T3 fibroblast cells treated with MH/DS/$Mg^{2+}$ complexes for 24 hours. FIG. 7F is an image of 3T3 fibroblast cells treated with fresh MH for 24 hours. FIG. 7C-7F confirmed that the fibroblast cells were healthy after complex treatment. The 3T3 cells were stained with cresyl violet prior to imaging. FIG. 7G is a graph illustrating nitrite production by macrophage treated with LPS, LPS and fresh MH (40 and 1 µg/mL), or LPS and MH released on day 1 (diluted to 40 µg/mL), day 52 (diluted to 1 µg/mL, Ca-based particle), and day 62 (diluted to 1 µg/mL, Mg-based particle). Cells without any treatment were used as control. *$P<0.05$ compared with LPS-treated culture. FIG. 7G demonstrates that MH released on day 52 from Ca-based particles and day 62 from Mg-based particles maintained the same bioactivity as fresh MH.

FIG. 10, comprising

FIG. 11, comprising

FIGS. 14A-14D, illustrates possible mechanism of $Ca^{2+}$ LBL assembly. FIG. 14A is a graph illustrating how monitoring of the UV absorbance of MH during DS/MH bilayer coating showed that the binding of MH to DS relied on the $Ca^{2+}$ in DS layers. FIG. 14B is a graph illustrating how monitoring of the UV absorbance of MH during DS/MH/GA trilayer coating indicated that the incorporation of MH into LBL assembly also relied on $Ca^{2+}$ present in DS layers. FIG. 14C is a graph illustrating how monitoring of the fluorescent intensity of FITC-GA showed that $Ca^{2+}$ was not required for DS/GA LBL assemblies. FIG. 14D is a graph depicting the thickness growth of film versus the number of deposited bilayers for $(DS+Ca^{2+}/MH+Ca^{2+}/GA+Ca^{2+})_8$. Data illustrated are average±STD (n=3).

FIGS. 20A-20B, illustrates the antibiofilm activity of the coatings. FIG. 20A illustrates XTT assays that demonstrate inactivation of bacteria in biofilms, and the efficacy of MH release from coating polymers. The virulent pathogens were allowed to developed 24 hour biofilms in 96-well plates coated with polymer alone or polymer with MH. A significant antibiofilm activity is observed throughout biofilm assay in the wells coated with MH-polymer. *, P<0.05 compared to uncoated control (polystyrene), +, P<0.05 compared to coating without MH. Data were presented as mean±SD (n=3). FIG. 20B is a series of fluorescent images of E. coli, S. aureus, and A. baumannii without any treatment, treated with fresh MH, or MH released from $Ca^{2+}$- or $Mg^{2+}$-based complexes. The cells were stained with "live" SYTO 9 stain (green fluorescence). Biofilm formation was inhibited by MH treatment. Scale bar=20 μm.

FIGS. 21A-21B, illustrates $Mg^{2+}$-based assembly of LbL films. FIG. 21A is a graph illustrating the UV absorbance of MH as a function of the number of trilayers. In each data set, the data points refer to, respectively: $DS+Mg^{2+}$/MH/GA; $DS/Mg^{2+}$/MH+$Mg^{2+}$/GA; $DS+Mg^{2+}$/MH/GA+$Mg^{2+}$; and $DS+Mg^{2+}$/MH+$Mg^{2+}$/GA+$Mg^{2+}$. FIG. 21B is a graph illustrating the thickness versus the number of ($DS+Ca^{2+}$/MH+$Ca^{2+}$/GA) trilayers.

FIGS. 23A-23B, illustrates the concentration effect of $Mg^{2+}$ added to DS layers of LbL assemblies in terms of (FIG. 23A) MH loading and (FIG. 23B) MH release.

FIG. 26 is a graph illustrating nitrite production by macrophage treated with LPS, LPS and fresh MH (0.5 μg/mL), or LPS and MH released on day 45 (diluted to 0.5 μg/mL). Cells without any treatment were used as control (con). *P<0.05 compared with LPS-treated culture.

FIG. 27, comprising FIGS. 27A-27B, illustrates the neuroprotective activity of released MH. Cultured neurons were treated with serum, serum and fresh MH (40 μg/mL), or serum and MH released on day 1 (diluted to 40 μg/mL and 80 μg/mL). Cells without any treatment were used as control. FIG. 27A is a graph depicting the result of the LDH assay. FIG. 27B is a series of images illustrating live/dead staining of cells. *P<0.05 denotes a significant decrease of nitrite level compared to LPS-treated culture. Data were presented as mean±SD (n=3).

FIG. 33, comprising FIGS. 33A-33H, is a series of images and graphs illustrating a study of macrophage adhesion on anti-adhesive coating. FIG. 33A is a bar graph illustrating macrophage adhesion on bare and coated catheters. FIGS. 33B-33H are a set of images illustrating remaining mouse macrophage adhesion on bare and coated catheters.

FIGS. 36A-36B, is a series of graphs illustrating the relationship between entrapment efficiency and DS/DOX ratio for $Ca^{2+}$ (FIG. 36A) and $Mg^{2+}$ (FIG. 36B) systems.

FIGS. 37A-37B, is a series of graphs illustrating the relationship between entrapment efficiency, and $Ca^{2+}$ concentration (FIG. 37A) and $Mg^{2+}$ concentration (FIG. 37B).

FIGS. 39A-39C, is a series of graphs illustrating the effect of metal ion on DOX release.

FIGS. 43A-43C, is a series of graphs illustrating the time-dependent formation of agarose/methylcellulose hydrogels.

FIGS. 45A-45B, is a series of bar graphs illustrating the bioactivity of released DOX.

FIGS. 46A-46B, is a series of bar graphs illustrating the time-dependent release of DOX.

FIGS. 47A-47E, illustrates the anti-cancer activity of complex-loaded hydrogel, as evidenced by Alamar blue assays (FIG. 47A) and microscopic imaging (FIGS. 47B-47E).

FIGS. 48A-48E, illustrates the safety of complex-loaded hydrogel, as evidenced by Alamar blue assays (FIG. 48A) and microscopic imaging (FIGS. 48B-48E).

DETAILED DESCRIPTION OF THE INVENTION

Figure 1:
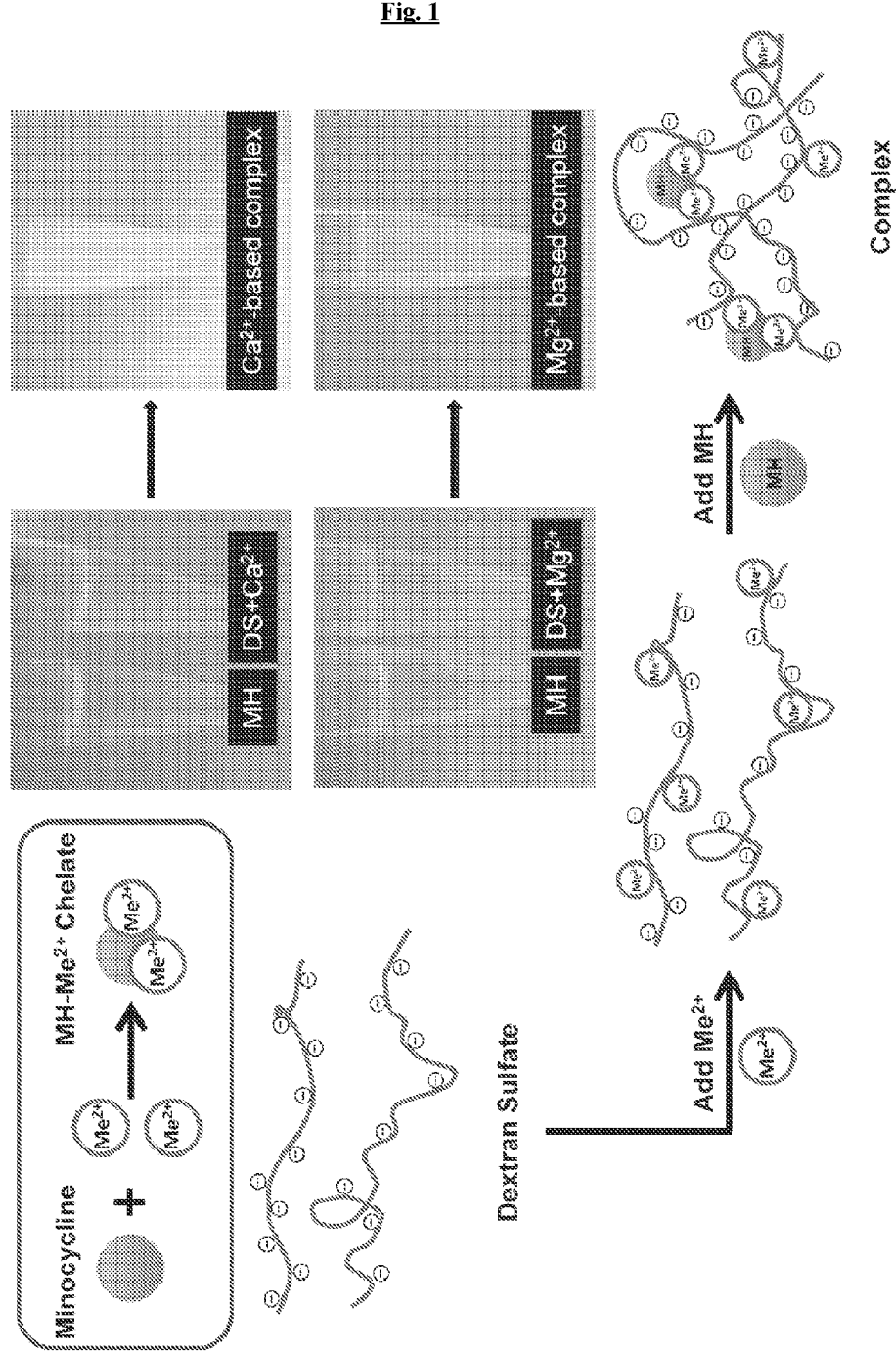
FIG. 1 is a series of images illustrating the mechanism of $Ca^{2+}$ or $Mg^{2+}$-mediated particle formation and macroscopic observations of the DS/MH/metal ion complexes. DS, MH and metal ions ("Me") are highly soluble in aqueous solution. A solution comprising these three components formed an insoluble DS/MH/metal ion complex. The suspension of the DS/MH/$Ca^{2+}$ complex had a bright yellow color, while the suspension of the DS/MH/$Mg^{2+}$ complex had a slightly yellow color.

The present invention relates to the unexpected discovery of novel compositions comprising a therapeutic agent, a polyelectrolyte, and a polyvalent metal ion, wherein the compositions are useful for localized drug delivery. The present invention further provides particles comprising the compositions of the invention. The present invention further provides ultrathin layer-by-layer (LbL) drug-containing films that are useful for localized drug delivery, including coating of surgical and medical equipment. The present invention further provides methods of preparing the compositions described herein. The present invention further provides methods of treating, ameliorating, or preventing a disease or disorder in a subject in need thereof, using the compositions of the invention.

In certain embodiments, the polyelectrolyte comprises a polyanion, a predominantly polyanionic polyampholyte, or any combinations thereof. In other embodiments, the composition is essentially free of a polycation. In yet other embodiments, the composition further comprises a polycation.

In certain embodiments, the compositions of the invention preserve the stability of the therapeutic agent during its rapid and/or sustained release. In yet other embodiments, the therapeutic agent and polyelectrolyte form a chelate with the polyvalent metal ion, forming a therapeutic agent/polyelectrolyte/metal ion complex. In other embodiments, the particles comprise nanoparticles. In yet other embodiments, the particles are embedded in a hydrogel. In yet other embodiments, the therapeutic agent is rapidly released from the compositions, and/or is released in a sustained release manner.

In certain embodiments, the disease or disorder comprises inflammation. In other embodiments, the disease or a disorder comprises spinal cord injury.

In certain embodiments, the compositions of the invention coat at least a portion of the surface of a technological device, such as but not limited to a neural prosthesis, such as but not limited to a stimulating electrode, recording electrode, or cochlear implant, wherein the technological device is implanted or inserted into a subject, as to treat or prevent inflammation and/or infection in the subject due to the implantation and/or insertion of the device into the subject.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "abnormal" when used in the context of organisms, tissues, cells or components thereof, refers to those organisms, tissues, cells or components thereof that differ in at least one observable or detectable characteristic (e.g., age, treatment, or time of day) from those organisms, tissues, cells or components thereof that display the "normal" (expected) respective characteristic. Characteristics that are normal or expected for one cell or tissue type might be abnormal for a different cell or tissue type.

As used herein, a "disease" is a state of health of an animal wherein the animal cannot maintain homeostasis, and wherein if the disease is not ameliorated then the animal's health continues to deteriorate.

As used herein, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, a disease or disorder is "alleviated" if the severity of a symptom of the disease or disorder, the frequency with which such a symptom is experienced by a patient, or both, is reduced.

As used herein, the terms "patient," "subject," "individual" and the like are used interchangeably, and refer to any animal, or cells thereof whether in vitro or in situ, amenable to the methods described herein. In a non-limiting embodiment, the patient, subject or individual is a human.

As used herein, the term "therapeutic" treatment refers to a treatment administered to a subject who exhibits signs of pathology, for the purpose of diminishing or eliminating those signs.

As used herein, the term "treating a disease or disorder" means reducing the frequency with which a symptom of the disease or disorder is experienced by a patient. Disease and disorder are used interchangeably herein.

As used herein, the term "therapeutically effective amount" refers to an amount that is sufficient or effective to prevent or treat (delay or prevent the onset of, prevent the progression of, inhibit, decrease or reverse) a disease or condition described or contemplated herein, including alleviating symptoms of such disease or condition.

As used herein, the term "effective amount" or "therapeutically effective amount" of a compound is that amount of compound that is sufficient to provide a beneficial effect to the subject to which the compound is administered.

As used herein, the term "effective amount" of a delivery vehicle refers to an amount sufficient of the delivery vehicle to effectively entrap, bind or deliver a compound.

As used herein, the term "DS" refers to dextran sulfate.

As used herein, the term "MH" refers to minocycline hydrochloride.

As used herein, the term "GA" refers to gelatin type A.

As used herein, the term "alg" refers to alginate.

As used herein, the term "LbL" film refers to layer-by-layer film.

As used herein, the terms "layer-by-layer assembly" or "LbL" interchangeably refer a layer-by-layer film, which is formed by a sequential adsorption of materials with complementary functional groups employing electrostatic interactions, hydrogen bonding and/or covalent interactions. In certain embodiments, the LbL assembly is incorporated within a hydrogel scaffold.

The term "nanoparticle" refers to a particle having one or more dimensions on the order of about 3,000 nm or less. In certain embodiments, the particle has one or more dimensions on the order of about 1,000 nm or less, about 100 nm or less, or about 10 nm or less, or about 1 nm or less.

The term "scaffold" refers to a structure comprising a biocompatible material that provides a surface suitable for adherence and proliferation of cells. A scaffold may further provide mechanical stability and support to the cells. A scaffold may be in a particular shape or form so as to influence or delimit a three-dimensional shape or form assumed by a population of proliferating cells. Such shapes or forms include, but are not limited to, films (e.g., a form with two-dimensions substantially greater than the third dimension), ribbons, cords, sheets, flat discs, cylinders, spheres, three-dimensional amorphous shapes, and the like.

As used herein, the term "hydrogel" or "aquagel" refers to a network of oligomers or polymer chains that are water-insoluble, sometimes found as a colloidal gel in which water is the dispersion medium.

As used herein, the term "complex coacervation" refers to the interaction of two or more macromolecules of opposite charge. In certain embodiments, in a liquid phase colloidal system, the phase that is more concentrated in macromolecular component is called the coacervate.

As used herein, the term "polyelectrolyte" refers to polymers whose repeat units bear a charged group. These groups can dissociate in aqueous solutions (e.g., water), making some or all of the polymer repeat units charged. After such electrolytic dissociation, the polymeric species is called a polycation or a polyanion if its repeat units are all positively charged or all negatively charged, respectively. A polyelectrolyte bearing both positive and negative charges is called an amphoteric polyelectrolyte, or a polyampholyte. The polyampholyte may be predominantly polycationic (if it bears more positive charges than negative charges), predominantly polyanionic (if it bears more negative charges than positive charges), or essentially neutral in nature (if it bears essentially the same number of positive and negative charges), respectively. In certain embodiments, the polyelectrolyte comprises a polyanion or a predominantly polyanionic polyampholyte. The generic term "polyion" or "polyionic" refers to electrolytically dissociated polymers of unspecified charge. The ions that dissociate from the polymer are known as counterions.

The term "biodegradable" includes polymers, compositions and formulations, such as those described herein, that are intended to degrade during use. Biodegradable polymers typically differ from non-biodegradable polymers in that the former may be degraded during use. In certain embodiments, such use involves in vivo use, such as in vivo therapy. In other embodiments, such use involves in vitro use. In general, biodegradation involves the degradation of a biodegradable polymer into its component subunits, or digestion, e.g., by a biochemical process, of the polymer into smaller, non-polymeric subunits. Two types of biodegradation may generally be identified. For example, biodegradation may involve cleavage of bonds (whether covalent or otherwise) in the polymer backbone. In such biodegradation, monomers and oligomers typically result, and even more typically, such biodegradation occurs by cleavage of a bond connecting one or more of subunits of a polymer. Further, biodegradation may involve cleavage of a bond (whether covalent or otherwise) internal to side chain or that connects a side chain to the polymer backbone. For example, a therapeutic agent or other chemical moiety attached as a side chain to the polymer backbone may be released by biodegradation. In certain embodiments, at least one type of biodegradation may occur during use of a polymer. As used herein, the term "biodegradation" encompasses all known types of biodegradation.

As used herein, the terms "entrapped," "incorporated" and "encapsulated" are interchangeably used to refer to a therapeutic agent incorporated in a polymeric composition, such as a composition disclosed herein. In certain embodiments, these terms include incorporating, formulating or otherwise including such agent into a composition which allows for fast or sustained release of such agent in the desired application. The terms may contemplate any manner by which a therapeutic agent or other material is incorporated into a polymer matrix, including for example: attached to a monomer of such polymer (by covalent or other binding interaction) and having such monomer be polymerized to give a polymeric formulation; distributed throughout the polymeric matrix; appended to the surface of the polymeric matrix (by covalent, ionic or any other binding interactions); encapsulated inside the polymeric matrix, and the like. The term "co-incorporation" or "co-encapsulation" refers to the incorporation of a therapeutic agent or equivalent and at least one other therapeutic agent or equivalent in a subject composition.

As used herein, the terms "biocompatible polymer" and "biocompatibility" when used in relation to polymers are recognized in the art. For example, biocompatible polymers include polymers that are generally neither toxic to the host, nor degrade (if the polymer degrades) at a rate that produces monomeric or oligomeric subunits or other byproducts at toxic concentrations in the host. In certain embodiments, biodegradation generally involves degradation of the polymer in a host, e.g., into its monomeric subunits, which may be known to be effectively non-toxic. Intermediate oligomeric products resulting from such degradation may have different toxicological properties, however, or biodegradation may involve oxidation or other biochemical reactions that generate molecules other than monomeric subunits of the polymer. Consequently, in certain embodiments, toxicology of a biodegradable polymer intended for in vivo use, such as implantation or injection into a patient, may be determined after one or more toxicity analyses. It is not necessary that any subject composition have a purity of 100% to be deemed biocompatible; indeed, it is only necessary that the subject compositions be biocompatible as set forth above. Hence, a subject composition may comprise polymers comprising 99%, 98%, 97%, 96%, 95%, 90%, 85%, 80%, 75% or even less of biocompatible polymers, e.g., including polymers and other materials and excipients described herein, and still be biocompatible.

As used herein, the terms "rapid release" and "released rapidly" are used interchangeably herein to refer to the release of the majority of the therapeutic agent, e.g., greater than about 50%, about 60%, about 70%, about 80%, or about 90% within a relatively short length of time, e.g., within about 2 hours, about 1 hour, about 40 minutes, about 30 minutes or about 10 minutes after administration to a subject.

The terms "sustained release," "slow release" and "released slowly" are used interchangeably herein to refer to the gradual release over an extended period of time of a therapeutic agent administered to a subject, and that may, although not necessarily, result in substantially constant blood or tissue levels of a therapeutic agent over an extended time period. The period of time may be greater than about 2 hours, about 6 hours, about 12 hours, about 1 day, about a week, about a month or more, and should be a release that is longer that the same amount of agent administered in bolus form or by rapid release.

The term "essentially free" of a decomposition or denaturation product as applied to a material indicates that the material contains less than about 5%, or less than about 1%, or less than about 0.5%, or less than about 0.1%, or less than about 0.05%, or less than about 0.01%, of any decomposition or denaturation product as compared to a control sample of the material, such as but not limited to the material before being formulated within the compositions of the invention.

As used herein, an "instructional material" includes a publication, a recording, a diagram, or any other medium of expression that can be used to communicate the usefulness of a composition or method of the invention in the kit for treating, preventing or alleviating various diseases or disorders recited herein. Optionally, or alternately, the instructional material can describe one or more methods of treating, preventing or alleviating diseases or disorders in a cell or a tissue of a mammal. The instructional material of the kit of the invention can, for example, be affixed to a container that contains the identified composition or delivery system of the invention or be shipped together with a container that contains the identified composition or delivery system. Alternatively, the instructional material can be shipped separately from the container with the intention that the instructional material and the composition be used cooperatively by the recipient.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 and the like, as well as individual numbers within that range, for example, 1, 2, 2.7, 3, 4, 5, 5.3, and 6. This applies regardless of the breadth of the range.

Description

The present invention relates to the unexpected discovery of novel compositions comprising a therapeutic agent, a polyelectrolyte, and a polyvalent metal ion, wherein the compositions are useful for localized drug delivery. The present invention further provides particles comprising the compositions of the invention. The present invention further provides ultrathin layer-by-layer (LbL) drug-containing films that are useful for localized drug delivery, including coating of surgical and medical equipment. The present invention further provides methods of preparing the compositions described herein. The present invention further provides methods of treating, ameliorating, or preventing a disease or disorder in a subject in need thereof, using the compositions of the invention.

In certain embodiments, the polyelectrolyte comprises a polyanion, a predominantly polyanionic polyampholyte, or any combinations thereof. In other embodiments, the composition is essentially free of a polycation. In yet other embodiments, the composition further comprises a polycation.

Therapeutic Agent/Polyelectrolyte/Metal Ion Complexes

The present invention provides a composition comprising at least one of each of a therapeutic agent, polyelectrolyte, and polyvalent metal ion. Without wishing to be limited by any theory, the formation of the therapeutic agent/polyelectrolyte/polyvalent metal ion complex is based on a novel mechanism of metal ion-mediated binding interaction. In this mechanism, the therapeutic agent can bind to a polyvalent metal ion to form a chelate, wherein the polyvalent metal ion acts as the linker to bind the therapeutic agent to a polyelectrolyte, which also has a high affinity for the polyvalent metal ion. The metal ion thus crosslinks the polyelectrolyte to the therapeutic agent, thus inducing formation of therapeutic agent/polyelectrolyte/polyvalent metal ion complexes.

In certain embodiments, the polyelectrolyte comprises a polyanion or a predominantly polyanionic polyampholyte. The therapeutic agent is loaded onto the composition and released at an unexpectedly slow rate because of the strong binding affinity to the polyvalent metal ion, which is itself bound to the polyelectrolyte, thus resulting in the sustained long-term release of the therapeutic agent.

Therapeutic Agents

In certain embodiments, the drug delivery system of the present invention comprises at least one therapeutic agent. The therapeutic agent may be incorporated into the compositions of the present invention to form a therapeutic agent/polyelectrolyte/metal ion complex, as described elsewhere herein. In certain embodiments, the therapeutic agent chelates at least a fraction of the polyvalent metal ion. In other embodiments, the polyelectrolyte chelates at least a fraction of the polyvalent metal ion. In yet other embodiments, the therapeutic agent chelates at least a fraction of the polyvalent metal ion, and the polyelectrolyte chelates at least a fraction of the polyvalent metal ion. In yet other embodiments, at least one polyvalent metal ion is chelated by the polyelectrolyte and the therapeutic agent. In yet other embodiments, at least one polyvalent metal ion is chelated by the polyelectrolyte but not by the therapeutic agent, or is chelated by the therapeutic agent but not by the polyelectrolyte.

A therapeutic agent that may used in the drug delivery system of the present invention includes, but is not limited to, an analgesic, anesthetic, antifungal, antibiotic, anti-inflammatory, anthelmintic, antidote, antiemetic, antihistamine, antihypertensive, antimalarial, antimicrobial, antipsychotic, antipyretic, antiseptic, antiarthritic, antituberculotic, antitussive, antiviral, cardioactive drug, cathartic, chemotherapeutic agent, colored or fluorescent imaging agent, corticoid, antidepressant, depressant, diagnostic aid, diuretic, enzyme, expectorant, hormone, hypnotic, mineral, nutritional supplement, parasympathomimetic, potassium supplement, radiation sensitizer, radioisotope, sedative, sulfonamide, stimulant, sympathomimetic, tranquilizer, urinary anti-infective, vasoconstrictor, vasodilator, vitamin, xanthine derivative, small organic molecule, naturally isolated entity or its analogs, organometallic agent, chelated metal or metal salt, peptide-based drug, peptidic or non-peptidic receptor targeting or binding agent, and any combinations thereof.

In certain embodiments, the therapeutic agent is anti-inflammatory and neuroprotective. In other embodiments, the therapeutic agent comprises minocycline. In yet other embodiments, the therapeutic agent comprises a minocycline salt, such as but not limited to minocycline hydrochloride (MH). Minocycline and all its non-toxic salts or derivatives are contemplated within the invention.

In certain embodiments, the therapeutic agent comprises a tetracycline antibiotic. In other embodiments, the tetracycline antibiotic comprises tetracycline. In yet other embodiments, the tetracycline antibiotic comprises minocycline hydrochloride. In yet other embodiments, the therapeutic agent comprises a quinolone. In yet other embodiments, the quinolone comprises ciprofloxacin. In yet other embodiments, the therapeutic agent comprises an anthracenedione. In yet other embodiments, the therapeutic agent comprises an anthracycline. In yet other embodiments, the therapeutic agent comprises a statin. In yet other embodiments, the therapeutic agent comprises a chemotherapeutic agent. In yet other embodiments, the chemotherapeutic agent comprises doxorubicin. In yet other embodiments, the therapeutic agent is further covalently attached to hydrogels of the present invention. In yet other embodiments, the therapeutic agent is not covalently attached to hydrogels of the present invention.

In certain embodiments, the therapeutic agents are used in amounts that are therapeutically effective, which varies widely depending largely on the particular agent being used. The amount of agent incorporated into the composition also depends upon the desired release profile, the concentration of the agent required for a biological effect, and the length of time that the biologically active substance has to be released for treatment. In certain embodiments, the biologically active substance may be blended with a polymer matrix at different loading levels, in one embodiment at room temperature and without the need for an organic solvent. In other embodiment, the compositions may be formulated as microspheres.

There is no critical upper limit on the amount of therapeutic agent incorporated except for that of an acceptable solution or dispersion viscosity to maintain the physical characteristics desired for the composition. The lower limit of the agent incorporated into the polymer system is dependent upon the activity of the therapeutic agent and the length of time needed for treatment. Thus, the amount of the agent should not be so small that it fails to produce the desired physiological effect, nor so large that the agent is released in an uncontrollable manner. Typically, within these limits, amounts of the therapeutic agents from about 1% up to about 80% may be incorporated into the present delivery systems. However, lesser amounts may be used to achieve efficacious levels of treatment for agent that are particularly potent.

Polyelectrolytes

In certain embodiments, the drug delivery system of the present invention comprises at least one polyelectrolyte. The polyelectrolyte may be incorporated into the drug delivery system to form a therapeutic agent/polyelectrolyte/metal ion complex, as described elsewhere herein. Any polyelectrolyte is contemplated for use in the present invention, as would be understood by one skilled in the art.

In certain embodiments, the polyelectrolyte comprises a polyanion or a predominantly polyanionic polyampholyte. In other embodiments, the polyelectrolyte comprises a polyanion. Examples of polyanions include, but are not limited to, dextran sulfate, heparin, chondroitin sulfate, hyaluronic acid, alginate, alginate sulfate, polyacrylic acid, poly(methyl methacrylate) (PMMA), poly(vinylsulfonic acid) (PVSA), poly(L-aspartic acid), poly(L-glutamic acid), poly(L-aspartic acid)-grafted-poly(ethylene glycol) (PAA-g-PEG), poly(L-glutamic acid)-grafted-poly(ethylene glycol) (PGA-g-PEG), poly(sodium 4-styrenesulfonate) (PSS), dermatan sulfate, carboxymethyl cellulose (CMC), or any combinations thereof. Such a polyanion optionally can be used in the form of a salt, e.g., sodium salt, lithium salt, or other similar salt. The polyanion used can be a sole polyanion, or can be a mixture of different types of polyanions (e.g., a so-called "plurality" wherein the plurality optionally comprises between two and five, added either simultaneously or sequentially). In certain embodiments, the polyanion is selected from the group consisting of dextran sulfate, heparin, chondroitin sulfate, hyaluronic acid, alginate, alginate sulfate, and any combinations thereof. In other embodiments, the polyanion comprises dextran sulfate.

Metal Ions

In certain embodiments, the drug delivery system of the present invention comprises at least one polyvalent metal ion. The metal ion may be incorporated into the drug delivery system to form a therapeutic agent/polyelectrolyte/metal ion complex, as described elsewhere herein. Any metal ion is contemplated for use in the present invention, as would be understood by one skilled in the art.

In some embodiments, the metal ion comprises a divalent metal ion, such as but not limited to beryllium, magnesium, zinc, cadmium, mercury, lead, calcium, copper (II), barium, iron (II), nickel, and tin. In certain embodiments, the divalent metal ion is selected from the group consisting of calcium, magnesium, zinc, iron (II), nickel, copper (II), and any combinations thereof. In other embodiments, the divalent metal ion comprises calcium. In yet other embodiments, the divalent metal ion comprises magnesium. In yet other embodiments, the metal is a trivalent metal ion, such as but not limited to chromium (III), aluminum, gallium, indium, iron (III), and any combinations thereof. In other embodiments, the metal is a tetravalent metal ion, such as but not limited to titanium (IV) and tin (IV).

The present invention also contemplates the use of two or more different metal ions. In certain embodiments, the metal ions comprise magnesium and calcium.

Layer by Layer (LbL) Assemblies

The present invention includes a drug delivery system comprising therapeutic agent/polyelectrolyte/polyvalent metal ion complexes embedded within an assembly of LbL assemblies. The LbL assemblies are capable of encapsulating and releasing multiple therapeutic agents. The LbL assemblies can be used as coatings for medical implants or devices, or as drug delivery patches. Examples of medical implants or devices include, but are not limited to, neural electrodes, sensors, stents, and scaffolds. The LbL assemblies can be loaded with therapeutic agent/polyelectrolyte/polyvalent metal ion complexes and used as a coating for medical implants or devices. In certain embodiments, the at least one therapeutic agent comprises minocycline hydrochloride. In certain embodiments, the medical implant or device is a neural electrode. In other embodiments, the medical implant or device is a urinary catheter.

The LbL assemblies of the present invention may comprise two or more overlaid layer units, wherein a layer unit is at least partially overlaid on another layer unit. In certain embodiments, an LbL assembly comprises two or more layers (i.e., multilayer unit), wherein the two or more layers may be prepared by alternate adsorption of oppositely charged components. In certain embodiments, an LbL assembly comprises two layers (i.e., bilayer unit). In certain embodiments, a trilayer unit comprises three layers (i.e., trilayer unit). For example, an LbL assembly may comprise a layer with materials that carry a net negative charge, wherein this layer is overlaid by another layer with materials that carry a net positive charge. This method permits the development of overlaid LbL assemblies, wherein two or more consecutive layers optionally comprise the same or different materials. In some embodiments, the material that carries a positive charge comprises a polymer. In some embodiments, the material that carries a negative charge comprises a polymer. Examples of polymers include, but are not limited to, dextran sulfate, chondroitin sulfate, hyaluronic acid, alginate and alginate sulfate. In certain embodiments, the LbL assembly comprises dextran sulfate, which carries a negative charge, overlaid with a layer of gelatin type A (GA), which carries a positive charge.

The present invention also contemplates LbL assemblies comprising a therapeutic agent/polyelectrolyte/metal ion complex and a positively charged polymer. Examples of positively charged polymers include, but are not limited to, chitosan, poly(L-lysine), polyethyleneimine (PEI), gelatin type A (GA), protamine, multiple bilayers of PEI/polystyrene sulfonate (PSS), or any combinations thereof. In certain embodiments, the therapeutic agent/polyelectrolyte/polyvalent metal ion complex comprises a MH/DS/$Ca^{2+}$ complex, and the positively charged polymer comprises GA. In other embodiments, the therapeutic agent/polyelectrolyte/metal ion complex comprises a MH/DS/$Mg^{2+}$ complex.

In certain embodiments, the loading of the therapeutic agent within the therapeutic agent/polyelectrolyte/polyvalent metal ion complex within the LbL assembly increases as the number of multilayers increases, allowing for the delivery of a higher local concentration of the therapeutic agent when the LbL assembly is applied in vivo. The LbL assemblies of the present invention may be synthesized with a positively charged polymer as the starting layer for electrostatic LbL assembly, as understood by one skilled in the art. In a preferred embodiment, the positively charged polymer comprises chitosan, poly(L-lysine), polyethyleneimine (PEI), gelatin type A (GA), protamine, multiple bilayers of PEI/polystyrene sulfonate (PSS), or any combinations thereof.

In certain embodiments, the LbL assembly comprises at least one bilayer unit. In other embodiments, the LbL assembly comprises at least one trilayer unit. In yet other embodiments, the LbL assembly comprises at least one (DS+$Ca^{2+}$/MH+$Ca^{2+}$/GA+$Ca^{2+}$) trilayer unit. In yet other embodiments, the LbL assembly comprises at least one (alginate sulfate/DS/MH) trilayer unit.

In certain embodiments, two or more multilayer units are layered upon each other in the LbL assembly to yield an LbL assembly comprising multiple overlaid multilayer units. In other embodiments, the LbL assembly comprises between about 2 and about 24 overlaid multilayer units. In yet other embodiments, the LbL assembly comprises about 8 overlaid multilayer units. In yet other embodiments, the LbL assembly comprises about 8 overlaid trilayer units. In yet other embodiments, the LbL assembly comprises about 8 overlaid (DS/MH+$Ca^{2+}$/GA) trilayer units. In yet other embodiments, the LbL assembly comprises about 8 overlaid (DS+$Ca^{2+}$/MH/GA) trilayer units. In yet other embodiments, the LbL assembly comprises about 8 overlaid (DS+$Mg^{2+}$/MH+$Mg^{2+}$/GA) trilayer units. In yet other embodiments, the LbL assembly comprises about 12 overlaid trilayer units.

Hydrogels

The present invention includes compositions comprising a hydrogel scaffold comprising a therapeutic agent/polyelectrolyte/metal ion complex, and methods of making the hydrogel scaffold. The hydrogel scaffolds are used to encapsulate particles comprised of therapeutic agent/polyelectrolyte/metal ion complexes of the present invention in order to immobilize the particles at the target site and to prevent the nanoparticles from being washed away by body fluid. In a specific embodiment, the particles comprise nanoparticles. In certain embodiments, the compositions of the invention are useful in the treatment and/or prevention of inflammation or cancer in a subject.

Hydrogels can generally absorb much fluid and, at equilibrium, typically are composed of 60-90% fluid and only 10-30% polymer. In certain embodiments, the water content of hydrogel is about 70-80%. Hydrogels may be prepared by crosslinking hydrophilic biopolymers or synthetic polymers. Examples of the hydrogels formed from physical or chemical crosslinking of hydrophilic biopolymers include but are not limited to, hyaluronans, chitosans, alginates (including alginate sulfate), collagen, dextran, pectin, carrageenan, polylysine, gelatins or agarose. Examples of hydrogels based on chemical or physical crosslinking synthetic polymers include but are not limited to (meth)acrylate-oligolactide-PEO-oligolactide-(meth)acrylate, poly(ethylene glycol) (PEO), poly(propylene glycol) (PPO), PEO-PPO-PEO copolymers (Pluronics), poly(phosphazene), poly(methacrylates), poly(N-vinylpyrrolidone), PL(G)A-PEO-PL(G)A copolymers, or poly(ethylene imine). In certain embodiments, the hydrogel scaffold comprises dextran sulfate. In other embodiments, the hydrogel scaffold comprises gelatin type A (GA). In yet other embodiments, the hydrogel scaffold comprises alginate. In yet other embodiments, the hydrogel scaffold comprises alginate sulfate. In yet other embodiments, the hydrogel scaffold comprises agarose. In yet other embodiments, the hydrogel scaffold comprises dextran sulfate and gelatin type A. In yet other embodiments, the hydrogel scaffold comprises dextran sulfate and alginate.

The stabilized cross-linked hydrogel scaffold of the present invention may be further stabilized and enhanced through the addition of one or more enhancing agents. The term "enhancing agent" or "stabilizing agent" refers to any compound added to the hydrogel scaffold, in addition to the high molecular weight components, that enhances the hydrogel scaffold by providing further stability or functional advantages. The enhancing agent may include any compound, such as polar compounds, that enhance the hydrogel scaffold by providing further stability or functional advantages when incorporated in the cross-linked hydrogel scaffold. Contemplated enhancing agents for use with the stabilized cross-linked hydrogel scaffold include polar amino acids, amino acid analogues, amino acid derivatives, intact collagen, and divalent cation chelators, such as ethylenediaminetetraacetic acid (EDTA) or salts thereof. Polar amino acids include tyrosine, cysteine, serine, threonine, asparagine, glutamine, aspartic acid, glutamic acid, arginine, lysine, or histidine. In certain embodiments, the contemplated polar amino acids are L-cysteine, L-glutamic acid, L-lysine, and L-arginine. Polar amino acids, EDTA, and mixtures thereof, are also contemplated enhancing agents. The enhancing agents may be added to the scaffold composition before or during the crosslinking of the high molecular weight components. The hydrogel scaffold may exhibit an intrinsic bioactivity, which may be a function of the unique stereochemistry of the cross-linked macromolecules in the presence of the enhancing and strengthening polar amino acids, as well as other enhancing agents.

Association of the therapeutic agent with the scaffold may be accomplished via a protease sensitive linker or other biodegradable linker. Molecules that can be incorporated into the hydrogel scaffold include, but are not limited to, vitamins and other nutritional supplements; glycoproteins (e.g., collagen); fibronectin; peptides and proteins; carbohydrates (both simple and/or complex); proteoglycans; antigens; oligonucleotides (sense and/or antisense DNA and/or RNA); antibodies (for example, to infectious agents, tumors, drugs or hormones); and gene therapy reagents.

Particles

In one aspect of the present invention, the drug delivery system comprises a particle that encapsulates the therapeutic agent/polyelectrolyte/polyvalent metal ion complexes. The use of particles for drug delivery is desirable because encapsulation of the therapeutic agent/polyelectrolyte/metal ion complex in a solid nanoparticle ensures that the therapeutic agent remains as a solid (i.e., undissolved), enhancing the long-term activity of therapeutic agents that are not stable in an aqueous environment for extended periods of time. In a specific embodiment, the particle comprises a nanoparticle.

The particle may comprise an additional biocompatible material. Examples of additional biocompatible materials include, but are not limited to, cellulose, natural polymers, such as proteins, including zein, modified zein, casein, gelatin, gluten, serum albumin, or collagen, and polysaccharides such as dextrans, polyhyaluronic acid and alginic acid, synthetic polymers such as polyphosphazenes, polyamides, polycarbonates, polyacrylamides, polysiloxanes, polyurethanes and copolymers thereof. In certain embodiments, the additional biocompatible material is non-toxic and does not elicit additional inflammatory responses in the subject. In other embodiments, the biocompatible material is dextran sulfate.

As contemplated within the present invention, a drug delivery system comprising a particle comprising a therapeutic agent/polyelectrolyte/metal ion is useful for extended sustained release of a therapeutic agent encapsulated in the particle. The particle of the present invention can be embedded within larger matrices for localized drug delivery to keep the particles immobilized at the target site. Examples of matrices include, but are not limited to, coatings, scaffolds, LbL assemblies, and hydrogels. In certain embodiments, the matrix is a hydrogel. In certain embodiments, the particle provides controlled release of the encapsulated therapeutic agent for at least 55 days. Increasing the concentration of the metal ions in the particle may extend the duration of controlled release. In certain non-limiting embodiments, increasing the calcium cation concentration from about 1.8 mM to about 3.6 mM increased the duration of controlled release of the therapeutic agent from about 40 days to about 54 days. In certain embodiments, controlled release of a therapeutic agent for at least 71 days can be achieved using a concentration of about 7.2 mM of magnesium ions. In other embodiments, long-term stable release of the therapeutic agent in a particle is obtained using a hydrogel comprising agarose. In yet other embodiments, short-term local release of the therapeutic agent in a particle, providing a high local dose, is obtained using a hydrogel scaffold comprising alginate, optionally further comprising dextran sulfate. In yet other embodiments, the therapeutic agent comprises MH. In yet other embodiments, the therapeutic agent comprises MH and a divalent cation.

Injectable Hydrogel

The present invention also includes an injectable hydrogel comprising particles loaded with therapeutic agents to immobilize the particles at the injection site. In certain embodiments, the injectable hydrogel of the invention is fluid enough to be injected into a subject and occupy whichever body compartment into which it is being injected, but eventually gels within the body.

Biodegradable Hydrogel Scaffold

The present invention also includes a hydrogel scaffold comprising a particle, wherein the therapeutic agent may become trapped within the hydrogel scaffold. As the therapeutic agent is released from the particle, it may become trapped in the hydrogel scaffold because the therapeutic agent forms a chelate with a metal ion of the hydrogel, thereby diminishing the local concentration of the therapeutic agent.

In certain embodiments, the hydrogel scaffold biodegrades rapidly following administration, such that the therapeutic agent is not trapped in the hydrogel scaffold and is instead immediately released at the site of administration, thereby providing the desired local concentration of the therapeutic agent. The degradation rate of a biodegradable polymer may often depend on a variety of factors, including the chemical identity of the linkage responsible for any degradation; the molecular weight, crystallinity, biostability, and degree of cross-linking of the polymer; the physical characteristics of the implanted polymer (such as its shape and size); and the mode and location of administration. For example, the greater the molecular weight, the higher the degree of crystallinity, or the greater the biostability of the biodegradable polymer, then the slower its biodegradation will be.

In certain embodiments, if the biodegradable polymer also has a therapeutic agent or other material associated with it, the biodegradation rate of such polymer may be characterized by a release rate of such materials. In such circumstances, the biodegradation rate may depend not only on the chemical identity and physical characteristics of the polymer, but also on the identity of any such material incorporated therein. In certain embodiments, the polymeric formulations biodegrade within a period that is acceptable for the desired application. In other embodiments, such as in in vivo therapy, such degradation preferably occurs during a period usually less than about five years, one year, six months, three months, one month, fifteen days, five days, three days, or even one day, upon exposure to a physiological solution with a pH between 6 and 8 having a temperature of between 25 and 37° C. In yet other embodiments, the polymer degrades within a period of between about one hour and several weeks, depending on the desired application. In yet other embodiments, rapid biodegradation of the hydrogel scaffold is promoted by the addition of magnesium cations. In yet other embodiments, sustained release of the therapeutic agent is promoted by loading the therapeutic agent/polyelectrolyte/metal complex in a hydrogel scaffold comprising agarose. In yet other embodiments, an increase in the amount of therapeutic agent released by the therapeutic agent/polyelectrolyte/metal complex is promoted by the increasing the amount of complexes loaded in a hydrogel scaffold comprising alginate. In yet other embodiments, an increase in the duration of release of the therapeutic agent by the therapeutic agent/polyelectrolyte/metal complex is promoted by loading the therapeutic agent/polyelectrolyte/metal complex in a hydrogel scaffold comprising agarose.

In some embodiments, the hydrogel may comprise a plurality of compositions of the invention. In certain embodiments, the hydrogel comprises a first composition and a second composition, where the first composition affords sustained release of the therapeutic agent or salt thereof, and the second composition affords rapid release of the therapeutic agent or salt thereof. The combination of two or more distinct compositions provides control over the dose and rate of release of the therapeutic agent.

In certain embodiments, the hydrogel scaffold does not comprise a metal ion, such that the therapeutic agent is not trapped by chelation and is instead immediately released into the site of administration, thereby providing the desired local concentration of the therapeutic agent. In other embodiments, the therapeutic agent is resuspended in a hydrogel scaffold comprising agarose, wherein the agarose hydrogel scaffold does not comprise metal ions.

Ultrathin Coatings

The LbL and hydrogel scaffolds of the present invention may be used as a ultrathin coating. These ultrathin coatings may reduce infections and inflammation associated with technological implants, for example implanted neural prostheses. The ultrathin coatings of the present invention are of a thickness that does not cause damage to the tissues surrounding the implant. In certain embodiments, the thickness of the ultrathin coating is equal to or less than about 10 µm. In other embodiments, the thickness of the ultrathin coating is equal to or less than about 1 µm. In yet other embodiments, the thickness of the ultrathin coating ranges from about 10 nm to 10 µm. In yet other embodiments, the thickness of the ultrathin coating ranges from about 100 nm to 10 µm.

The coatings of the present invention provide sustained release of a therapeutic agent, and may be assembled by LbL assembly. In certain embodiments, the LbL assembly comprises negatively-charged gelatin type B and DS, and a therapeutic agent that carries a positive charge. In other embodiments, the therapeutic agent that carries a positive charge comprises a neurotrophin. In certain embodiments, the neurotrophin comprises neurotrophin NGF (Nerve Growth Factor).

Combinations of therapeutic agents are also contemplated as a component of the coatings. In certain embodiments, the combination of therapeutic agents comprises MH and neurotrophin NGF, which synergistically provide neuroprotection by reducing inflammation and infection, and improving neuronal survival around implanted neural prostheses. In one aspect, the coating affords sustained release of MH and neurotrophins, making stable long term recording possible and facilitating clinical translations of recording electrodes for paralyzed patients, as well as a next generation of closed-loop deep brain simulation.

Methods of Drug Delivery

The drug delivery system of the present invention facilitates the sustained and controlled release of a therapeutic agent from a therapeutic agent/polyelectrolyte/metal ion complex. In certain embodiments, the sustained release of the therapeutic agent takes place over a period of at least 24 days. In other embodiments, the sustained release of the therapeutic agent takes place over a period of at least 35 days. In yet other embodiments, the sustained release of the therapeutic agent takes place over a period of at least 46 days. In yet other embodiments, the sustained release of the therapeutic agent takes place over a period of at least 55 days. In yet other embodiments, the sustained release of the therapeutic agent takes place over a period of at least 71 days.

The drug delivery system of the present invention also facilitates the rapid release of a therapeutic agent from a therapeutic agent/polyelectrolyte/polyvalent metal ion complex. In one embodiment, the rapid release of the therapeutic agent takes place over a period of about 20 minutes. In another embodiment, the rapid release of the therapeutic agent takes place over a period of about 30 minutes. In yet another embodiment, the rapid release of the therapeutic agent takes place over a period of about 40 minutes. In yet another embodiment, the rapid of the therapeutic agent takes place over a period of about 50 minutes. In yet another embodiment, the rapid release of the therapeutic agent takes place over a period of about 1 hour. In yet another embodiment, the rapid release of the therapeutic agent takes place over a period of about 2 hours.

The kinetics of the controlled release may be modulated, for example, by altering the presence, concentration, or type of metal ions within an LbL assembly or a hydrogel. In certain embodiments, a weak initial burst release is obtained when calcium ions are present in all layers of a (DS/MH/GA) trilayer unit. In other embodiments, a strong initial burst release is obtained when calcium ions are not present in the GA layer of the (DS/MH/GA) trilayer unit. In yet other embodiments, an initial burst release and a subsequent burst release are obtained when calcium ions are not present in either the MH or GA layer of the (DS/MH/GA) trilayer unit.

When the LbL assembly or hydrogel is flexible, moldable or flowable, it may be placed anywhere within the body. It may be inserted into an anatomic area, either through an open surgical wound, under direct or indirect vision, or through any of the access devices routinely used in the art to enter such areas, for example, in-dwelling or acutely-inserted catheters, needles, drains, superselective angiography means and the like. A flowable or fluid LbL assembly or hydrogel may be adapted for mixing with the transudate or exudate found within or expected to gather within the anatomic area. A flowable or fluid LbL assembly or hydrogel may be instilled in an anatomic area during surgery on organs or structures therein to decrease the likelihood of recurrent disease when there is a high risk for its development. In certain embodiments, a polymer composition may also be incorporated in access devices, so that a therapeutic agent is released into the anatomic area within which the access device resides. The polymer composition may also be used to produce coatings for other solid implantable devices.

In certain embodiments, LbL assemblies or hydrogels comprising particles may be administered to a subject via surgery. In other embodiments, LbL assemblies or hydrogels comprising particles may be administered to a subject without the use of surgery. In yet other embodiments, the LbL assembly or hydrogel is injected into the subject. In other embodiments, the LbL assembly or hydrogel is injected topically onto an injured spinal cord to avoid the use of surgery. In yet other embodiments, the LbL assembly or hydrogel is injected into the subdural space between dura and spinal cord tissue to cover the injured spinal cord. This treatment does not cause additional tissue damage because the hydrogel scaffold remains outside of the spinal cord tissue. The LbL assembly or hydrogel may comprise materials known to those skilled in the art. In certain embodiments, the hydrogel scaffold comprises alginate and/or alginate sulfate. In other embodiments, the LbL assembly or hydrogel comprises an alginate-dextran sulfate blend.

Methods

The invention includes a method of treating, ameliorating or preventing a disease or disorder in a subject in need thereof, wherein the disease or disorder comprises inflammation. The method comprises administering to the subject an effective amount of a therapeutic agent using the drug delivery systems of the invention.

In certain embodiments, the disease or disorder is elected from the group consisting of chronic inflammation, autoimmune disease, spinal cord injury (SCI), stroke, myocardial infarction, chronic heart failure, diabetes, circulatory shock, a chronic inflammatory disease, cancer, a neurodegenerative disorder, traumatic brain injury, severing of a peripheral nerve, nerve root impingement, a traumatic injury, and any combinations thereof. In other embodiments, the inflammation results from an infection related to the implantation of a technological device in a subject. Non-limiting examples of a technological device include, but are not limited to, a medical implant, cosmetic implant, vascular implant, auditory implant, cochlear implants, orthopedic implant, bone plate, screw, joint prosthetic, breast implant, artificial larynx implant, maxillofacial prosthetic, dental implant, pacemaker, cardiac defibrillator, penile implant, drug pump, drug delivery device, sensors, monitor, neurostimulator, incontinence alleviating device, intraocular lens, water transporting sack, electrolyte transporting sack, glucose transporting sack, oxygen transporting sack, cells replacing a lost or damaged function of the human body, tissues replacing a lost or damaged function of the human body, neural prosthetic, recording electrode, cochlear implant, and any combinations thereof. In certain embodiments, the subject is a mammal. In other embodiments, the mammal is a human.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

Example 1: Controlled and Sustained Release of MH

Described herein is a complex coacervation composed of MH, divalent metal ions ($Ca^{2+}$ and $Mg^{2+}$) and dextran sulfate (DS), a biocompatible natural polysaccharide. The entrapment efficiency is defined as the ratio of the weight of MH encapsulated in metal ion concentration.

Figure 2:
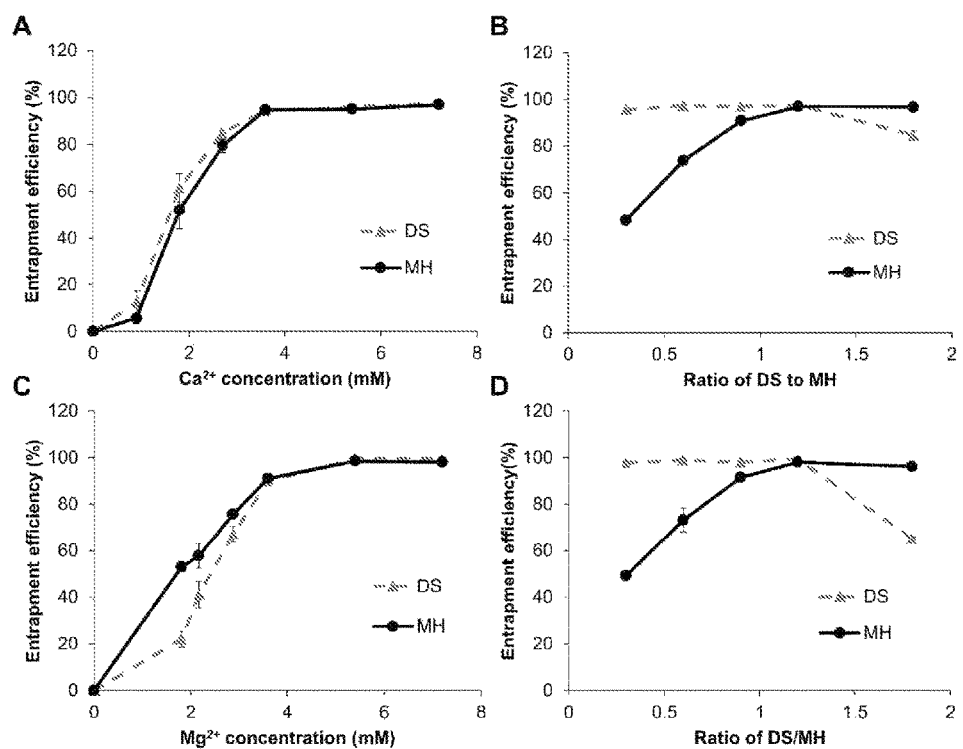
FIG. 2, comprising

As illustrated in FIG. 2, for $Ca^{2+}$-based composition the encapsulation efficiencies for both MH and DS increased rapidly with increasing $Ca^{2+}$ concentration up to 3.6 mM (94.7±0.7% and 94.4±0.6%), after which further increasing $Ca^{2+}$ concentration to 7.2 mM only slightly increased the encapsulation efficiencies of MH and DS to 96.9±0.2% and 97.8±0.1%, respectively. FIG. 2C illustrates that for $Mg^{2+}$-based complex the encapsulation efficiencies of MH and DS versus $Mg^{2+}$ concentration showed similar pattern, except that they reached plateau (98.5±0.2% and 99.4±0.3%) at 5.4 mM. Further increasing $Mg^{2+}$ concentration to 7.2 mM had little effect on the encapsulation efficiencies of MH and DS (98.0±0.4% and 99.4±0.1%). This result suggests that divalent metal ions play an important role in DS and MH encapsulation into the composition.

In addition, when the encapsulation efficiencies of MH and DS versus metal ion concentration reached plateau, the entrapment efficiency of MH reached plateau as well. When the concentration of metal ions was 7.2 mM, $Ca^{2+}$-based composition and $Mg^{2+}$-based composition had similar entrapment efficiency of MH (45.3% and 45.2%).

Dynamic light scattering (DLS) measurement showed that the hydrodynamic diameters of $Ca^{2+}$- and $Mg^{2+}$-based composition were 723 and 1,100 nm respectively (FIG. 3A). Scanning electron microscopy (SEM) images (FIGS. 3B-3C) illustrate that the compositions were composed of nanoparticles with sizes ranging from 50 to 100 nm, and the nanoparticles can form aggregates. This may explain the larger particle size obtained from DLS measurement.

The release of MH from the MH/DS/metal ion complex was observed to last more than 71 days. The biocompatibility and anti-inflammatory activity of MH released from the MH/DS/metal ion complex was also assayed. The initial release of MH from the MH/DS/metal ion complex was not found to be cytotoxic to endothelial cells. MH released from MH/DS/metal ion complexes late in the study maintained the same anti-inflammatory properties as freshly-added MH. These results described herein support the use of a MH/divalent metal ions/DS complex coacervation system as an effective delivery system for MH.

Materials

All chemicals were obtained from Sigma-Aldrich and used without further purification. Particle size was measured by zeta-potential. Scanning electron microscopy (SEM) was performed by Zeiss Supra 50VP SEM. UV-vis spectroscopy was assessed by Tecan M200 plate reader.

Polyelectrolyte Complex Formation

DS (at a concentration ranging from 3 µg/mL to 100 mg/mL), MH (at a concentration ranging from 0.05 mg/mL to 50 mg/mL), and a polyvalent metal ion (either $Ca^{2+}$ or $Mg^{2+}$ at a concentration ranging from 0.1 mM to 3.7 M) were mixed together. The MH/DS/metal ion complexes were formed in the system, which was subsequently centrifuged. The loading of the MH/DS/metal ion complex was assessed by measuring the concentration of MH and DS in supernatant. The concentration of MH was measured by UV-vis spectroscopy at 245 nm. The concentration of dextran sulfate was determined by the titration of sulfate functions, performed with the cationic dye toluidine blue (Drogoz et al., 2007, Langmuir 23:10950-10958). 50 µl Toluidine blue solution (1 mM) were added to the solution and mixed for 15 mM After centrifugation (10,000 rpm for 10 min) to remove the DS/toluidine blue complex, the absorbance was measured at 484 nm, corresponding to the unbound dye.

In Vitro MH Release Assay

The centrifuged MH/DS/metal ion complex was incubated in Hank's Balanced Salt Solution (HBSS) at 37° C. for quantification of MH release. Every 24 h, the HBSS present was removed and replaced with fresh HBSS. The amount of MH released every 24 h was determined by UV absorbance at 245 nm.

Bioactivity

3T3 fibroblast cells were cultured in Dulbecco's modified Eagle's medium (DMEM) supplemented with 10% fetal bovine serum and 1% penicillin/streptomycin. The cells were seeded in 96-well tissue culture plates at a density of 30,000 cells per well. 24 h after seeding, a polyelectrolyte complex incorporating 4 µg MH was added to 100 µl of cell culture medium. 40 µg/mL of fresh MH were used as a control. After 24 h, cell viability was determined using a cell counting assay (Roche) according to the manufacturer's instruction, and cell morphology was imaged by staining the cells with cresyl violet (0.5 mg/mL) for 30 min after the cells were fixed.

RAW264.7 murine macrophages were cultured in Dulbecco's modified Eagle's medium (DMEM) supplemented with 10% fetal bovine serum and 1% penicillin/streptomycin. The cells were seeded in 96-well tissue culture plates at a density of 60,000 cells per well. 48 h after seeding, MH released during a 24 h period was diluted to 1 µg/mL with cell culture medium, and added to the macrophage culture together with LPS. 1 µg/mL fresh MH was used as a control to compare the bioactivity of the fresh MH with the bioactivity of the MH released from the MH/DS/metal ion complex. After 48 h, the accumulated levels of nitrite in the cell culture medium was measured with Griess reagent (Promega). The level of nitrite was used as an indicator of the amount of nitric oxide (NO) produced by the macrophage.

Formation of MH/DS/Metal Ion Complex

For the preparation of the MH/DS metal ion complex, DS was dissolved in either a $CaCl_2$ or $MgCl_2$ solution, to form a DS+$Ca^{2+}$ or DS+$Mg^{2+}$ solution, respectively. MH was dissolved in DI water to form a MH solution. The MH/DS/metal ion formed a precipitate immediately upon mixing an equal volume of clear DS+$Ca^{2+}$ or DS+$Mg^{2+}$ solution, and MH solution (FIG. 1). When $Ca^{2+}$ was used, the color of the MH/DS/$Ca^{2+}$ composition was yellow. When $Mg^{2+}$ was used, the color of the MH/DS/Mg$^{2+}$ complex was white or light yellow. The complexes formed a suspension and could be pelleted after centrifugation. Incubating the MH/DS/Mg$^{2+}$ complex with CaCl$_2$ solution (7.2 mM) for 24 h caused the MH/DS/Mg$^{2+}$ complex to turn yellow, while the MH/DS/Mg$^{2+}$ complex incubated with MgCl$_2$ solution (7.2 mM) for 24 h maintained its original color (FIG. 1).

The entrapment efficiency was investigated using various metal ion concentrations and different mass ratios of DS to MH. No MH/DS/metal ion complexes were formed without Ca$^{2+}$ or Mg$^{2+}$ present in the mixture. The entrapment efficiency of MH and DS increased as the concentration of Ca$^{2+}$ or Mg$^{2+}$ added to the complex increased (FIGS. 2A & 2C). At a DS/MH ratio of 1.2, the entrapment efficiency of MH and DS was observed to increase as the concentration of Mg$^{2+}$ ions increased. When the concentration of Ca$^{2+}$ or Mg$^{2+}$ was above 7.2 mM, the entrapment efficiency of MH and DS was found to be above 95%. Increasing addition of one component increased the entrapment efficiency of the other component, indicating DS and MH form a complex by interacting with each other, as opposed to interacting only with metal ions.

When comparing the mass ration of DS/MH, the entrapment efficiency of MH increased as the DS/MH mass ratio increased (7.2 mM Mg$^{2+}$, 1 mg/mL MH) (FIGS. 2B & 2D). Conversely, the entrapment efficiency of DS decreased as the mass ratio of DS to MH increased (FIGS. 2B & 2D). Additional polyvalent metal ions, such as Zn$^{2+}$ and Fe$^{2+}$, were examined, and these ions also induced the formation of MH/DS/metal ion complexes. With sufficient Ca$^{2+}$ or Mg$^{2+}$ and a preferred ratio of DS to MH, over 98% of both MH and DS could be loaded into the MH/DS/metal ion complex.

After the complexes were rinsed by DI water and resuspended, DLS measurement showed the size of the DS/MH/Ca$^{2+}$ complexes was about 723 nm and the size of DS/MH/Mg$^{2+}$ complexes was about 1,100 nm (FIG. 3A). The SEM images (FIGS. 3B-3C) showed that the complexes were composed of particles with a size of about 50-100 nm. These particles may also be forming aggregates, where the aggregates range in size from about 0.5-1 μm. The DLS measurements obtained in these experiments support this hypothesis.

Effect of Metal Ion Concentration on Release of MH Polyelectrolyte Complex

Figure 4:
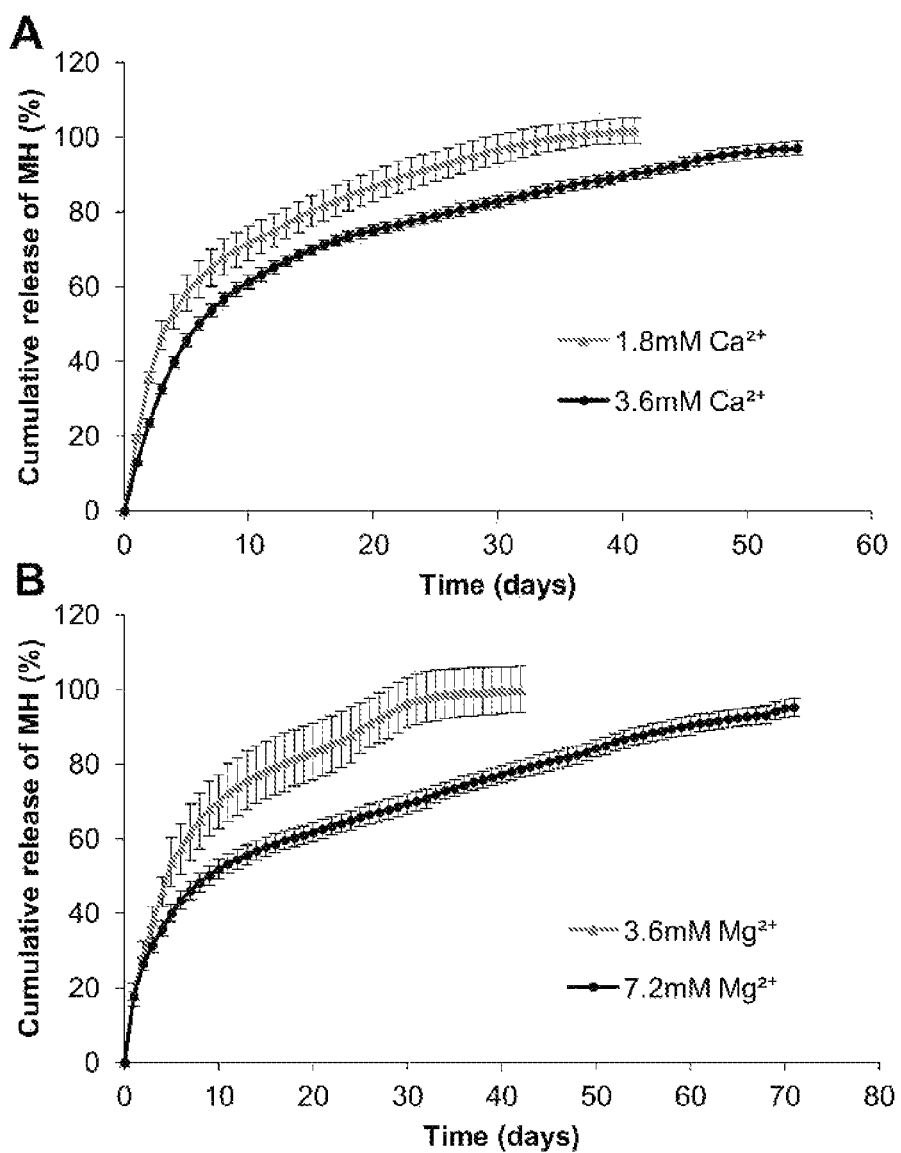
FIG. 4, comprising
Figure 5:
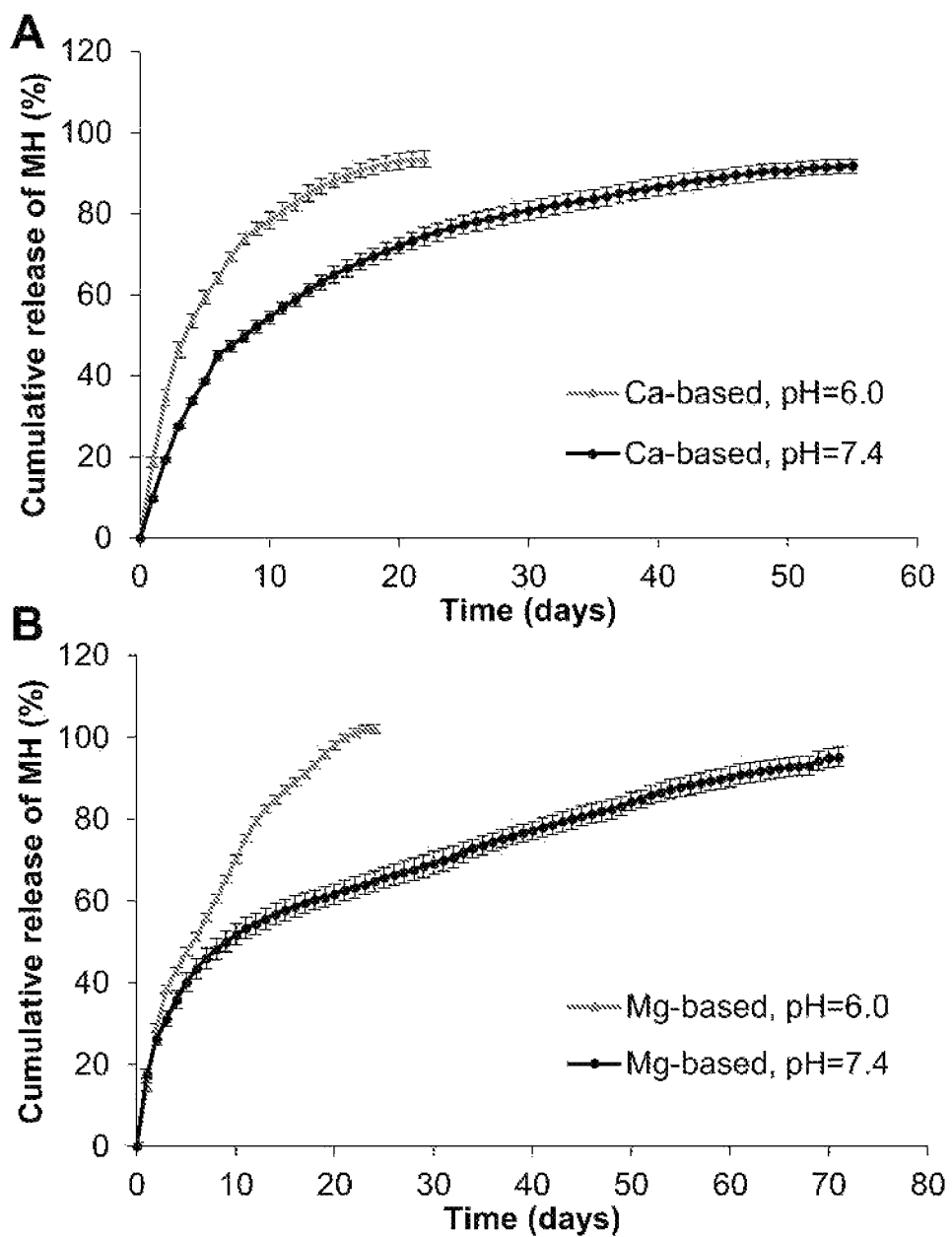
FIG. 5, comprising

The release of MH from the MH/DS/metal ion complex was monitored by the absorbance of MH. Various concentrations of metal ions (1.8 mM or 3.6 mM Ca$^{2+}$; 3.6 mM or 7.2 mM Mg$^{2+}$) were used in the complex formation to investigate the role of metal ion binding in MH/DS/metal ion complex. A fixed loading of 340 μg of MH with a fixed DS/MH ratio of 1.2:1 was used in these MH/DS/metal ion complexes. The release profile showed long term release of MH when either Ca$^{2+}$ or Mg$^{2+}$ was used in the MH/DS/metal ion complexes (FIG. 4). The release profile for Ca$^{2+}$ showed long-term release of MH up to 53 days with a 3.6 mM concentration of Ca$^{2+}$ (FIG. 4A). The release profile for Mg$^{2+}$ showed long-term release of MH up to 71 days with a 7.2 mM concentration of Mg$^{2+}$ (FIG. 4B). Furthermore, after an initial burst, the release of MH followed the zero-order release kinetics in both concentrations of Mg$^{2+}$ (3.6 mM and 7.2 mM) used to form the MH/DS/Mg$^{2+}$ complexes (FIG. 4B). A higher concentration of metal ions was observed to decrease the initial burst release of MH and prolonged the slow release of MH from the MH/DS/metal ion complex.

Due to its critical role in the binding affinity, the concentration of Ca$^{2+}$ or Mg$^{2+}$ was observed to not only affect the loading of MH in the MH/DS/metal ion complex, but also affected the release of MH from the MH/DS/metal ion complex. Higher concentration of Ca$^{2+}$ or Mg$^{2+}$ promoted the binding affinity between MH and DS, thus decreasing the initial burst and prolonging the release. After initial burst, the rate that MH was released from the MH/DS/metal ion complex remained constant over an extended period of time, supporting zero-order release kinetics.

Effect of pH of Release Medium

Figure 6:
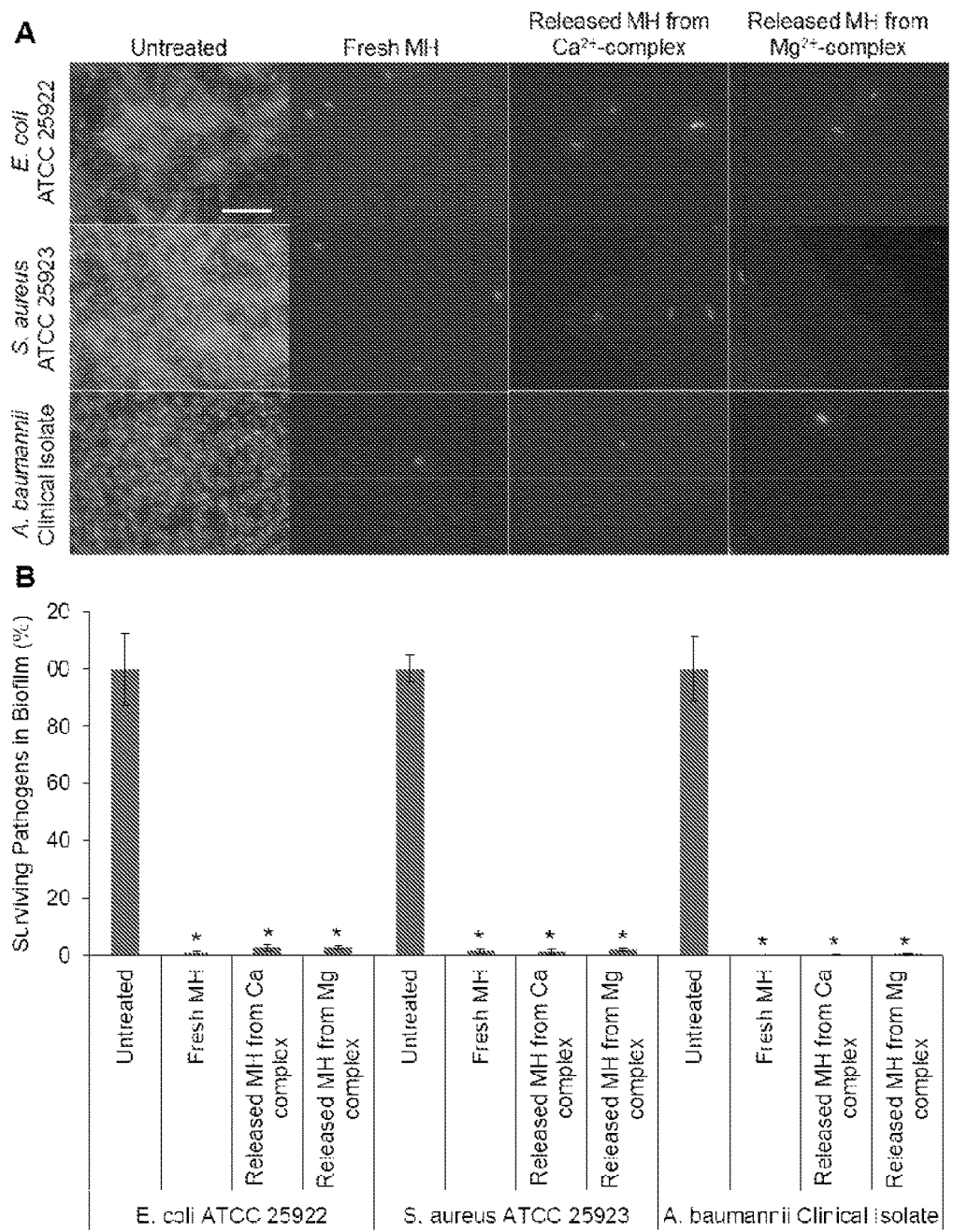
FIG. 6, comprising

To simulate pathological and physiological conditions of a reduced extracellular pH at an area of tissue injury or inflammation, HBSS with pH of 6.0 and 7.4 was used as the release medium. The final concentration of MH, DS, and Ca$^{2+}$ within the MH/DS/Ca$^{2+}$ complex was 1 mg/mL, 1.2 mg/mL, and 7.2 mM, respectively. As illustrated in FIG. 6A, the long-term release of MH from MH/DS/Ca$^{2+}$ complexes lasted up to 55 days at a pH of 7.4 (and 22 days at pH 6.0, being accompanied by a high initial burst release). The release of MH from MH/DS/Mg$^{2+}$ complexes lasted for 24 days at pH 6.0 and was accompanied by a high initial burst release. Conversely, the release of MH from MH/DS/Mg$^{2+}$ complexes at pH 7.4 lasted for 71 days and was accompanied by a small initial burst release (FIG. 6B).

In low pH, which is usually found in pathological conditions, the interaction between MH and DS within the MH/DS/metal ion complex was weakened, resulting in an increase in the release rate of MH from the MH/DS/metal ion complex. Thus, the sensitivity of the MH/DS/metal ion complex toward pH provides a drug delivery system in which the rate at which MH is released from the MH/DS/metal ion complex may be manipulated based on the changing physiology of the system.

Bioactivity

Figures 7A, 7B:
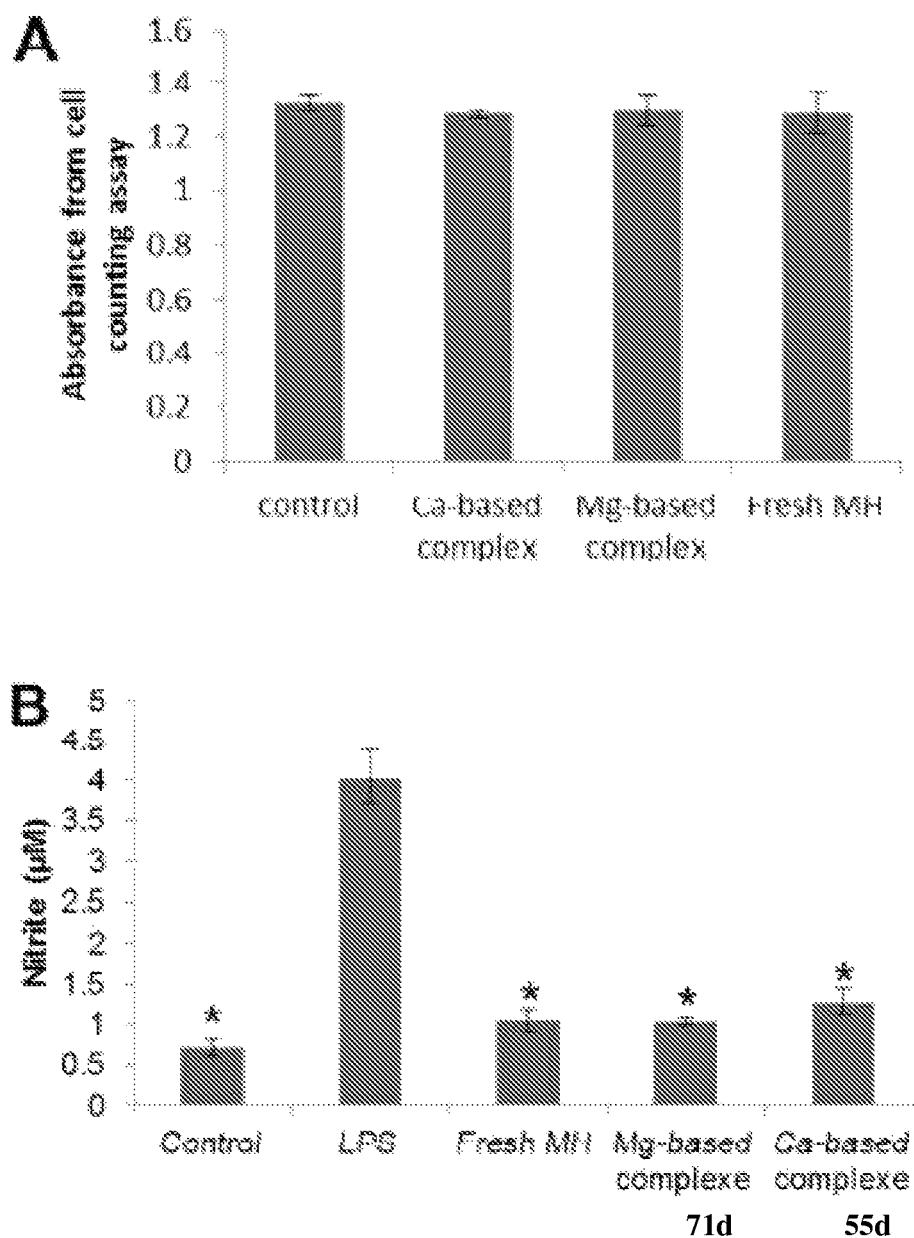
FIGS. 7A-7G, illustrates the cytotoxicity of MH/DS/metal ion complex.
Figures 7C, 7D, 7E, 7F:
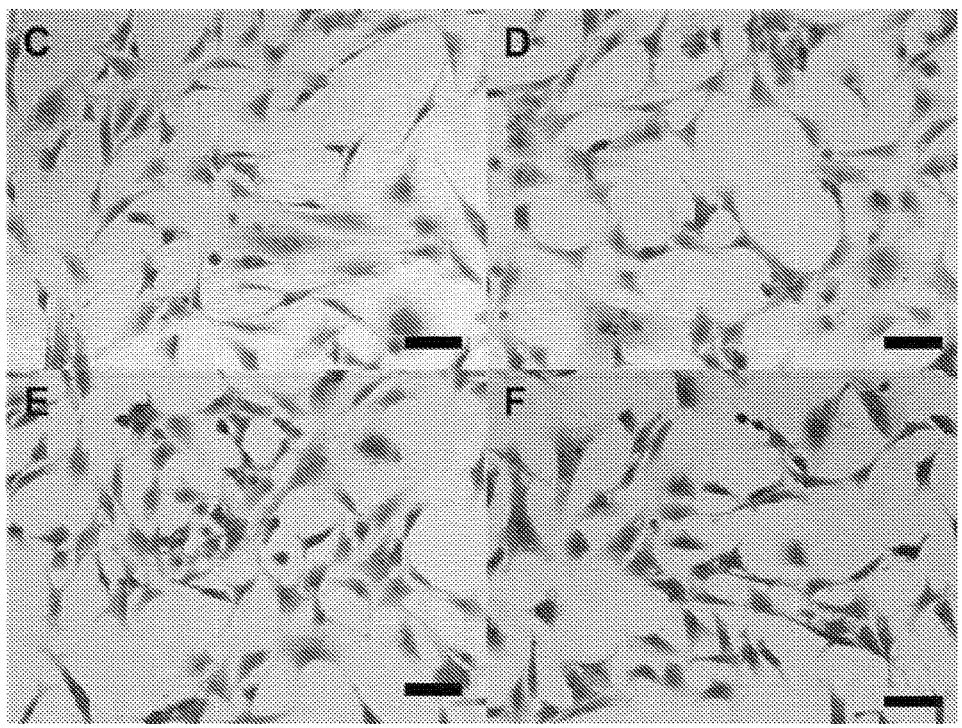

In vitro cytotoxicity of the polyelectrolyte MH/DS/metal ion complexes were studied by using 3T3 fibroblast cells. Cell counting assay results showed that there was no significant difference between cells treated with MH/DS/metal ion complexes versus cells treated with fresh MH or control cells which were untreated (FIG. 7A). Cell morphology was examined after treatment with MH/DS/metal ion complexes (FIGS. 7C-7F). Fibroblast cells maintained their health after treatment with MH/DS/metal ion complexes, suggesting that the MH/DS/metal ion complexes were not cytotoxic toward the fibroblasts.

The anti-inflammatory activity of MH released from MH/DS/metal ion complexes was studied using RAW264.7 macrophages. The cells were stimulated with lipopolysaccharide (LPS) to induce the upregulation of nitric oxide (NO), a potent inflammatory mediator and neurotoxic molecule. The level of NO produced can be determined by measuring the amount of nitrite released from the macrophages. Nitrite is an indicator of NO production, as nitrite is one of two primary, stable, and nonvolatile products of NO degradation. MH released from the MH/DS/metal ion complexes during a 24 h period on each of the first and last days of the study was diluted to 0.5 μg/mL and added to LPS-treated macrophage cultures. 0.5 μg/mL fresh MH were used as a control. LPS treatment was found to significantly increase NO production in macrophages in instances when MH was released from MH/DS/metal ion complexes and when fresh MH was added (FIG. 7B). Both fresh MH and MH released from MH/DS/metal ion complexes on the last day of the study significantly reduced NO production. No significant difference was observed between the NO levels of cells treated with fresh MH versus cells treated with MH released from MH/DS/metal ion complexes, supporting the hypothesis that MH released from the complexes maintains similar bioactivity to freshly-added MH.

Figure 7G:
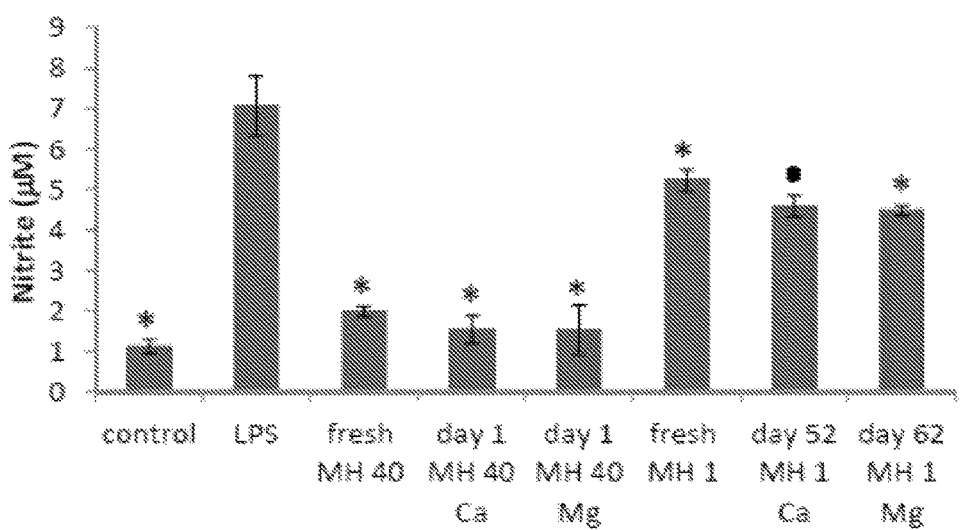

In another set of experiments, LPS treatment was found to significantly increase NO production in macrophages. Both fresh MH and MH released on day 1, day 52 and day 62 significantly reduced NO production, and there was no significant difference between the NO level in fresh MH and released MH-treated cultures at the same MH concentrations (FIG. 7G).

Example 2: Therapeutic Agent/Polyelectrolyte/Metal Ion Complexes Mediated by Ion-Binding Interaction Materials Gelatin type A (GA), poly(ethylene imine) (PEI), chitosan, protamine, poly-L-lysine, DS, heparin, chondroitin sulfate (CS), hyaluronic acid (HA), alginate, MH, tetracycline, and ciprofloxacin were obtained from Sigma-Aldrich.

The reagents have been classified into four categories for the following experiments: polyanions, therapeutic agents, metal ions, and polycations. Experiments were conducted where one compound was selected from each of the categories of polyanions, therapeutic agents, and metal ions, or one compound was selected from each of the categories of polyanions, therapeutic agents, metal ions, and polycations.

The categories and their corresponding reagents are as follows. Polyanions: DS, heparin, CS, HA and alginate; Therapeutic agents: minocycline, tetracycline, and ciprofloxacin; Metal ions: $Ca^{2+}$, $Mg^{2+}$, $Zn^{2+}$, $Fe^{2+}$, $Ni^{2+}$; and $Cu^{2+}$; and Polycations: GA, PEI, protamine, and poly-L-lysine.

Formation of Therapeutic Agent/Polyelectrolyte/Metal Ion Complexes

One compound from each of the categories of polyanions/therapeutic agents/metal ions, or one compound from each of the categories of polyanions/therapeutic agents/metal ions/polycations, was selected and the compounds were mixed together. The concentration of polyanions ranged from 1 μg/mL to 100 mg/mL. The concentration of therapeutic agents ranged from 0.01 mg/mL to 50 mg/mL. The concentration of metal ions ranged from 0.1 mM to 4 M. The concentration of polycations ranged from 0 to 100 mg/mL. Therapeutic agent/polyanion complexes were formed during mixing.

Effects of Metal Ions on Therapeutic Agent/Polyanion/Metal Ion Complex Formation Therapeutic agent/polyanion complexes were not observed to form under conditions where polyvalent metal ions were absent. The addition of polyvalent metal ions to the mixtures led to the formation of therapeutic agent/polyanion/metal ion complexes under most conditions (Table 1).

TABLE 1

Conditions resulting in therapeutic agent/polyanion/metal ion complex formation (N/A* = Gel formation)

| Polyanions | Metal ions | | | | | | |
|---|---|---|---|---|---|---|---|
| | $Ca^{2+}$ | $Mg^{2+}$ | $Zn^{2+}$ | $Fe^{2+}$ | $Ni^{2+}$ | $Cu^{2+}$ | None |
| Minocycline/Polyanion/Metal Ion Complex Formation | | | | | | | |
| Dextran sulfate | Yes | Yes | Yes | Yes | Yes | Yes | No |
| Heparin | Yes | Yes | Yes | Yes | Yes | Yes | No |
| Chondroitin sulfate | Yes | Yes | Yes | No | Yes | Yes | No |
| Hyaluronic acid | No | No | No | No | Yes | Yes | No |
| Alginate | N/A* | No | N/A* | No | Yes | N/A* | No |
| Alginate sulfate | Yes | Yes | Not tested | Not tested | Not tested | Not tested | Not tested |
| Tetracycline/Polyanion/Metal Ion Complex Formation | | | | | | | |
| Dextran sulfate | Yes | Yes | Yes | Yes | Yes | Yes | No |
| Heparin | No | No | Yes | No | Yes | Yes | No |
| Chondroitin sulfate | No | No | No | No | Yes | Yes | No |
| Hyaluronic acid | No | No | No | No | No | No | No |
| Alginate | N/A* | No | N/A* | Yes | Yes | N/A* | No |
| Ciprofloxacin/Polyanion/Metal Ion Complex Formation | | | | | | | |
| Dextran sulfate | Yes | Yes | Yes | Yes | Yes | Yes | No |
| Heparin | Yes | Yes | Yes | Yes | Yes | Yes | No |
| Chondroitin sulfate | Yes | Yes | Yes | No | Yes | Yes | No |
| Hyaluronic acid | No | No | No | No | No | No | No |
| Alginate | No | No | N/A* | Yes | Yes | N/A* | No |

Effects of Positively Charged Polymers on Therapeutic Agent/Polyanion/Metal Ion Complex Formation The presence of positively charged polymers was not critical for therapeutic agent/polyanion/metal ion complex formation. The addition of polycations including chitosan, PEI, GA, protamine and polylysine improved the stability and size polydispersity of particles. Although not wishing to be bound by any particular theory, these results suggest that any positively charged polymer could be used in the formation of the particles, as long as the presence of the polycation does not interfere with the formation of the therapeutic agent/polyanion/metal ion complex.

Example 3: Injectable Hydrogel Comprised of Therapeutic Agent/Polyelectrolyte/Metal Ion Complexes Release MH for Spinal Cord Repair Described herein is a drug delivery system that can locally deliver MH with sufficient dose and duration. This drug delivery system may be used to reduce secondary injury and improve functional recovery in a rat contusion SCI model. This drug delivery system may be used in the clinical treatment of SCI. The potential of MH to target many secondary injury mechanisms, and protect neural tissue from multiple neurotoxic insults after SCI, has been well documented. However, the inability to translate the high MH doses used in experimental animals to tolerable doses in human patients has limited the clinical application of MH treatment for SCI. The novel drug delivery system described herein allows for local delivery of MH with sufficient concentration and duration to treat SCI, and is more effective in reducing secondary injury and promote functional recovery than systemic administration.

As described herein, particles comprised of MH/DS/metal ion complexes were embedded in agarose and alginate hydrogels in order to immobilize the particles at the site of injection and further control drug release. These hydrogel systems may be injected topically on an injured spinal cord, or intrathecally to avoiding invasive surgical operations. An injectable hydrogel system comprising agarose, and particles comprised of DS/$Mg^{2+}$/MH complexes, or DS/$Mg^{2+}$/MH/chitosan complexes, or DS/$Mg^{2+}$/MH/gelatin type A complexes, is herein described.

Materials

DS, chitosan, gelatin type A, and MH were obtained from Sigma-Aldrich. Agarose was obtained from FMC.

Formation of Particles

DS, MH, $CaCl_2$ and $MgCl_2$ were mixed together and vortexed for 10 sec to provide a solution containing particles comprising MH/DS/metal ion complexes. The concentration of DS ranged from 1 µg/mL to 100 mg/mL. The concentration of MH ranged from 0.01 mg/mL to 50 mg/mL. The concentration of $MgCl_2$ ranged from 2 mM to 40 mM. The concentration of $MgCl_2$ ranged from 0 to 2 mM.

Figure 8:
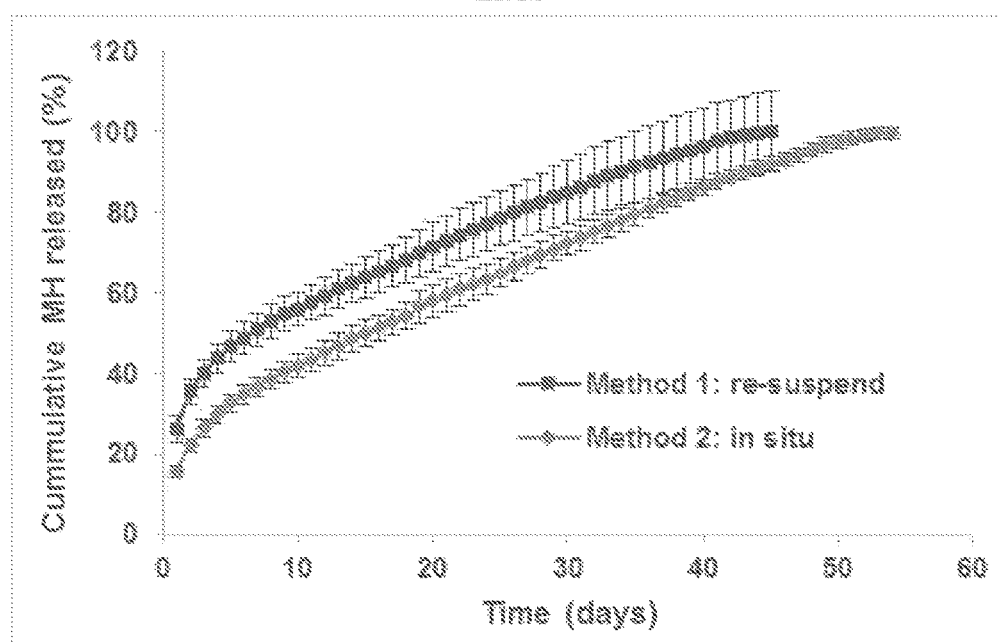
FIG. 8 is a graph illustrating the percent of MH released daily from Mg-based particles embedded in agarose hydrogel. Method 1 involved first fabricating the particles, then redispersing the particles in 1.5% agarose solution. The mixture was kept at low temperature (4° C.) for 20 minutes to allow gel formation. Method 2 involved first dissolving agarose in the solution of DS and $MgCl_2$, and then mixing with MH solution to form the particles in gel solution, followed by cooling at 4° C. for 20 minutes to promote gel formation.

The method of particle preparation includes but is not limited to the following method, which was used in the release study illustrated in FIG. 8. DS was dissolved in $MgCl_2$ solution (14.4 mM) at the concentration of 2.4 mg/mL. MH was dissolved in DI water at the concentration of 2 mg/mL. Equal volumes of DS solution and MH solution were mixed; particles were formed immediately when the solutions were mixed. The final concentrations of DS, MH and $Mg^{2+}$ were 1.2 mg/mL, 1 mg/mL, 7.2 mM, respectively.

Particle Encapsulation in Agarose Hydrogel

The particles were embedded within agarose hydrogels by way of one of two methods.

Method 1:

The particles were centrifuged and then redispersed in an agarose solution in water or HBSS (the concentration of agarose ranged from 0.5% to 5%), and then the mixture was kept at low temperature (4° C.) for over 5 minutes to allow gel formation. For the release study illustrated in FIG. 8 (method 1), the particles were centrifuged at 6,000 rpm for 10 min, followed by removal of the supernatant. Agarose was dissolved in HBSS or water by heating to 80° C., followed by cooling to 37° C. (final agarose concentration was 1.5%). The particles were resuspended in agarose solution, and cooled to 4° C. for 20 min to allow gel formation. For the quantification of MH release, particles containing 2 mg MH were resuspended in 1 ml agarose solution (i.e., MH concentration in agarose hydrogel was 2 mg/ml). 100 µl of this hydrogel was washed three times with HBSS and incubated with 500 µl HBSS. Every 24 h, the HBSS was removed and replaced with fresh HBSS. UV absorbance (245 nm) was used to quantify MH released during each 24 hour period.

Method 2:

The particle was formed inside agarose solution. Components for particle fabrication, for example, single component among DS, MH and divalent metal ions (Ca/Mg), or multiple components among DS, MH and divalent metal ions, were dissolved in agarose solution (agarose concentration ranged from 0.5% to 5%), and then mixed with other components. For the release study illustrated in FIG. 8 (method 2), MH was dissolved in DI water at the concentration of 4 mg/mL. DS was dissolved in $MgCl_2$ solution (28.8 mM) at the concentration of 4.8 mg/mL, and then agarose solid powder was added at the concentration of 3% w/v. This DS solution (containing $MgCl_2$ and agarose) was heated to 70-80° C. to dissolved agarose powder, followed by cooling to 37° C. Equal volumes of DS solution (containing $MgCl_2$ and agarose) and MH solution were mixed; particles were formed immediately. This mixture was cooled to 4° C. for 20 min to allow gel formation. The final concentration of agarose, DS, MH and $Mg^{2+}$ was 1.5% w/v, 2.4 mg/mL, 2 mg/mL, and 14.4 mM, respectively. 100 µl of this hydrogel was washed three times with HBSS and incubated with 500 µl HBSS. Every 24 h, the HBSS was removed and replaced with fresh HBSS. UV absorbance at 245 nm was used to determine the amount of MH released during each 24 hour period.

Figure 9:
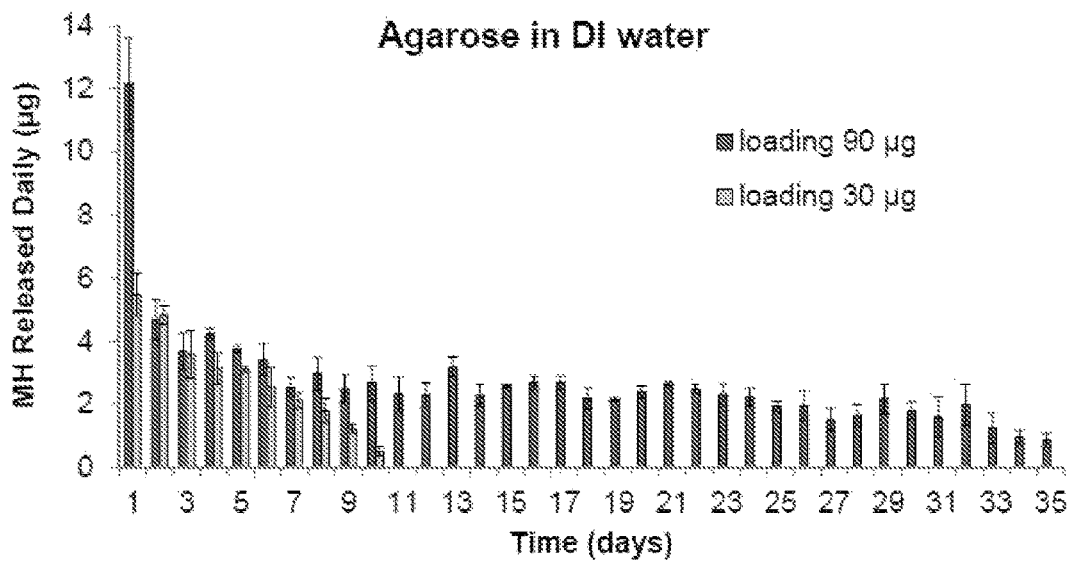
FIG. 9 is a graph illustrating the MH mass released daily from Mg-based particles embedded in agarose hydrogel. Agarose was dissolved in DI water with different initial loadings.

For the release study illustrated in FIG. 9, MH was dissolved in DI water at the concentration of 2 and 0.67 mg/ml. DS was dissolved in $MgCl_2$ solution (14.4 and 4.8 mM) at the concentration of 2.4 or 0.8 mg/ml, and then agarose solid powder was added at the concentration of 3% w/v. This DS solution (containing $MgCl_2$ and agarose) was heated to 70-80° C. to dissolved agarose powder, followed by cooling to 37° C. Equal volumes of DS solution (containing $MgCl_2$ and agarose) and MH solution were mixed. Particles were formed immediately when the solutions were mixed. And then this mixture was cooled to 4° C. for 20 min to allow gel formation. The final concentrations of agarose, DS, MH and $Mg^{2+}$ for 90 µg loading were 1.5% w/v, 1.2 mg/ml, 1 mg/ml and 7.2 mM, respectively. The final concentrations of agarose, DS, MH and $Mg^{2+}$ for 30 µg loading were 1.5% w/v, 0.4 mg/ml, 0.33 mg/ml and 2.4 mM, respectively. 100 µl hydrogel were washed three times with HBSS and incubated with 500 µl HBSS. Every 24 h, the HBSS was removed and replaced with fresh HBSS. UV absorbance at 245 nm was used to determine the amount of MH released during each 24 hour period.

Figure 10A:
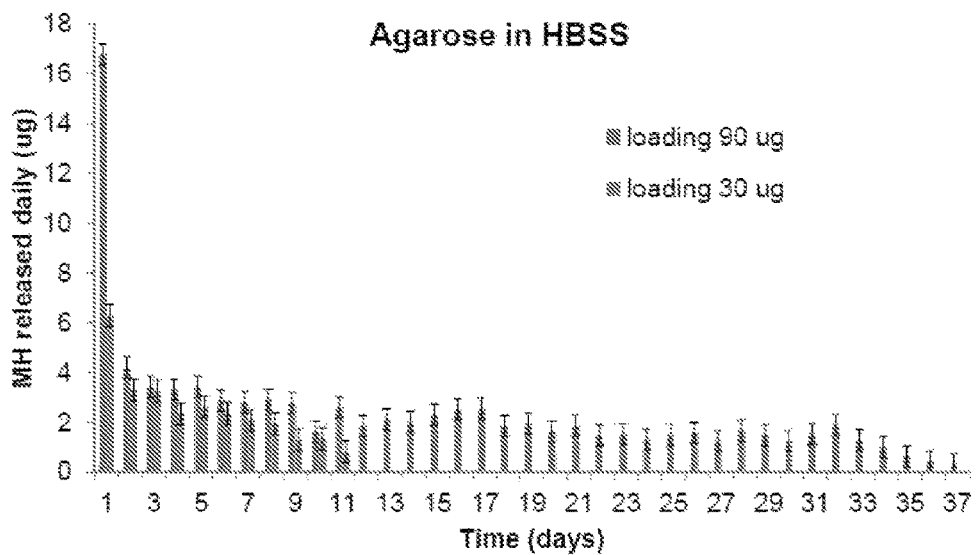
FIGS. 10A-10B, is a graph illustrating the daily released MH mass (FIG. 10A) and the cumulative MH release (FIG. 10B) from $Mg^{2+}$-based particles embedded in agarose hydrogel. Agarose was dissolved in HBSS with various initial loadings.
Figure 10B:
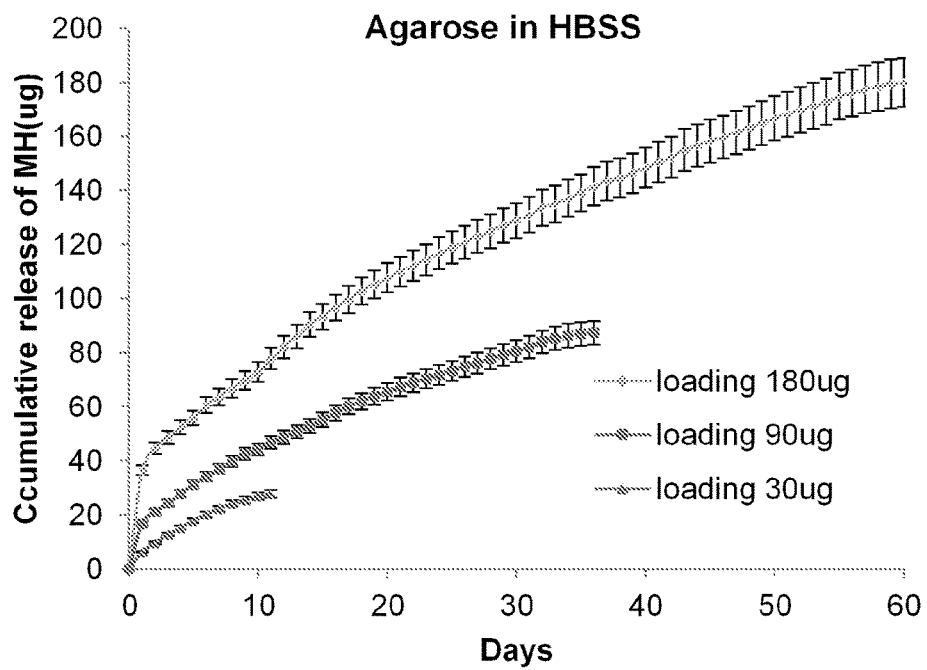
Figure 11A:
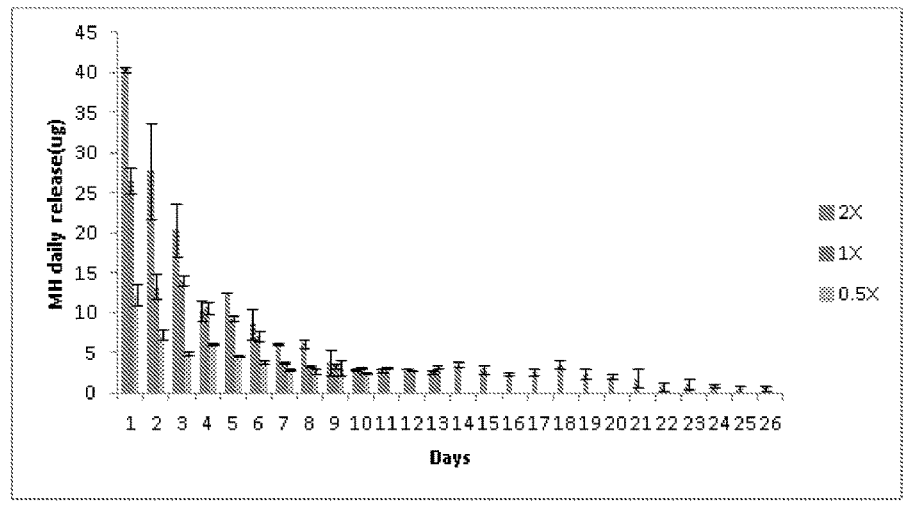
FIGS. 11A-11B, is a graph illustrating the MH daily release (FIG. 11A) and the MH cumulative release (FIG. 11B) from $Mg^{2+}$-based particles doped with chitosan and embedded in agarose hydrogel to achieve fast, high-dose release. Agarose was dissolved in HBSS with various initial loadings.
Figure 11B:
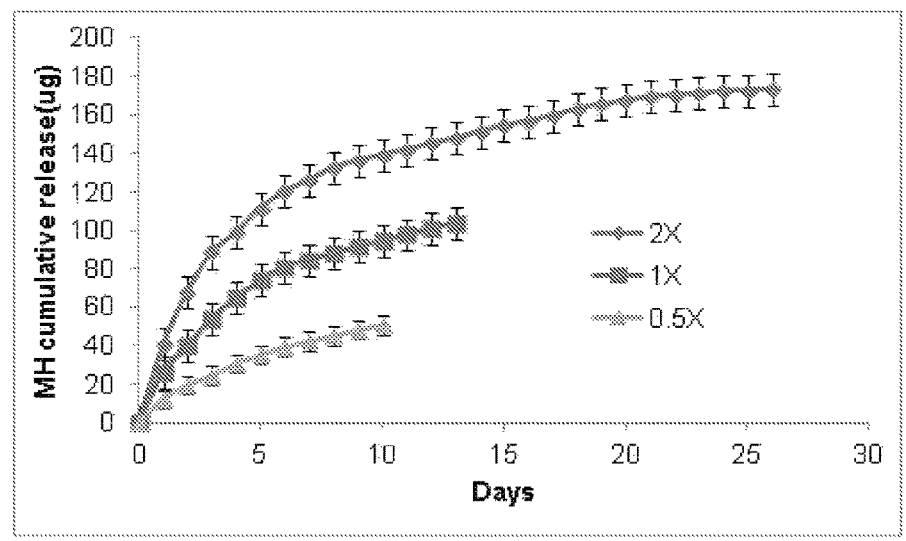
Figure 12:
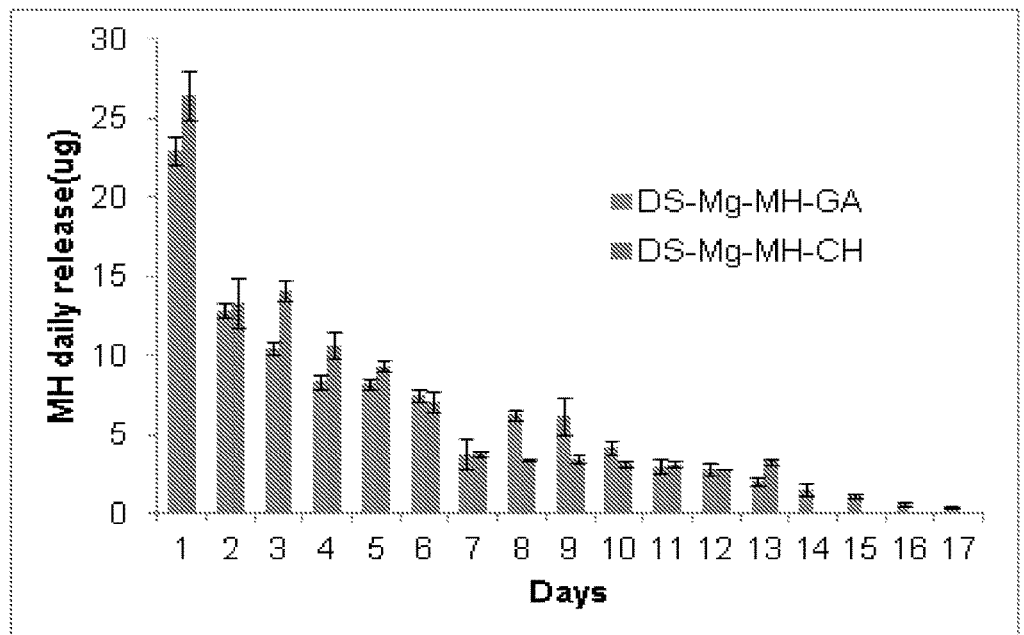
FIG. 12 is a graph illustrating the MH mass released daily from Mg-based particles doped with either chitosan or gelatin type A and embedded in agarose hydrogel to achieve fast, high-dose release. Agarose was dissolved in HBSS with various initial loadings.

For the release study illustrated in FIG. 10, DS was dissolved in HBSS at 8 mg/ml. MH was dissolved in HBSS at the concentration of 4 and 1.33 mg/ml. Agarose was dissolved in HBSS at 3% w/v at 70° C. and subsequently cooled down to 37° C. DS was mixed with $MgCl_2$ in HBSS solution and then diluted in HBSS to obtain a solution with 4.8 and 1.6 mg/ml DS, and 28.8 and 9.6 mM $MgCl_2$, labeled as "DS+$MgCl_2$" solution. 500 µl of MH solution were slowly added into 500 µl of "DS+$MgCl_2$" solution to allow particle formation. This mixture was added into 1 ml of agarose solution as soon as agarose solution was cooled to 37° C. After mixing with agarose, the entire mixture was cooled in 4° C. fridge for 20 min to allow gelation of agarose. The final concentration of agarose, DS, MH and $Mg^{2+}$ for 90 µg loading was 1.5% w/v, 1.2 mg/ml, 1 mg/ml, 7.2 mM, respectively. The final concentrations of agarose, DS, MH and $Mg^{2+}$ for 30 µg loading were 1.5% w/v, 0.4 mg/ml, 0.33 mg/ml and 2.4 mM, respectively. 100 µl hydrogel were washed three times with HBSS and incubated with 500 µl HBSS. Every 24 h, the HBSS was removed and replaced with fresh HBSS. UV absorbance at 245 nm was used to determine the amount of MH released during each 24 hour period.

Particle Doped with Chitosan or Gelatin Type A (GA) for Fast Release of MH

Dextran sulfate (DS), minocycline (MH), GA, and magnesium chloride ($MgCl_2$) were dissolved in Hank's Balanced Salt Solution (HBSS). Chitosan was dissolved in acetic acid (0.6% v/v). DS and $MgCl_2$ solutions were mixed, labeled as "DS+$MgCl_2$" solution. Chitosan (or GA) and MH solutions were mixed, labeled as "Chitosan (or GA)+MH" solution. Particles were formed after adding "Chitosan (or GA)+MH" solution slowly in the "DS+$MgCl_2$" solution. After centrifuging particle suspension in 6,000 rpm for 10 minutes, supernatant was removed. MH concentration in supernatant was measured with UV absorbance at 245 nm and used to calculate entrapment efficiency of MH in particle. The final concentrations of DS, MH, and chitosan (or GA) were 1.2, 1, and 1 mg/ml, respectively. The final concentration of $MgCl_2$ was 7.2 mM.

Particle Encapsulation in Agarose Hydrogel

Method 1:

Agarose was dissolved in HBSS at the concentration of 1.5% w/v at 70° C., followed by cooling to 37° C. The particles were resuspended in agarose solution by pipetting several times, until no large particles were observed and whole mix solution was uniform, then the system was cooled down to 4° C. for 20 min to allow gel formation.

Method 2:

Particles created in situ in agarose hydrogel. Chitosan was dissolved in acetic acid (0.6% v/v). GA, DS and MH was dissolved in HBSS. Agarose was dissolved in HBSS at 3% w/v at 70-80° C. and subsequently cooled down to 37° C. Chitosan (or GA) and MH were mixed and diluted in HBSS (labeled as "chitosan+MH" solution). DS was mixed with $MgCl_2$ solution and then diluted in HBSS (labeled as "DS+$MgCl_2$" solution). 500 µl of "chitosan+MH" solution were slowly added into 500 µl of "DS+$MgCl_2$" solution to allow particle formation. This mixture was added into 1 ml 37° C. agarose solution, and the entire mixture was cooled in a 4° C. fridge for 20 min to allow gelation of agarose.

For the release study illustrated in FIG. 10, chitosan was dissolved in acetic acid (0.6% v/v) at concentration of 16 mg/ml. GA was dissolved in HBSS at concentration of 8 mg/ml. DS was dissolved in HBSS at 16 mg/ml. MH was dissolved in HBSS at 16 mg/ml or 8 mg/ml, with heat as needed. Agarose was dissolved in HBSS at 3% w/v at 70-80° C. and subsequently cooled down to 37° C. Chitosan and MH were mixed and diluted in HBSS to obtain a solution with 4 mg/ml chitosan (or GA) and 4 mg/ml MH, labeled as "chitosan (or GA)+MH" solution. DS was mixed with $MgCl_2$ solution and then diluted in HBSS to get a solution with 4.8 mg/ml DS and 28.8 mM $MgCl_2$, labeled as "DS+$MgCl_2$" solution. 500 µl of "chitosan (or GA)+MH" solution were slowly added into 500 µl of "DS+$MgCl_2$" solution to allow particle formation. This mixture was added into 1 ml of agarose solution as soon as agarose solution was cooled to 37° C. After mixing with agarose, the entire mixture was cooled in 4° C. fridge for 20 min to allow gelation of agarose. MH concentration in the gel was 1 mg/ml (1×). For the other loading density, concentration of "chitosan (or GA)+MH" solution and "DS+$MgCl_2$" solutions were changed accordingly (2× means double concentrations in both "chitosan+MH" and "DS+$MgCl_2$" solutions. 0.5× means half concentrations in both "chitosan+MH" and "DS+$MgCl_2$" solutions).

For the quantification of MH release, various amounts of MH were loaded in 100 µl agarose hydrogel and injected in a 48 well plates, then incubated with 500 µl HBSS. In certain embodiments, 1× represented particles containing 100 µg MH loaded in 100 µl agarose hydrogel, 0.3× represented particles containing 30 µg MH loaded in 100 µl agarose hydrogel, 2× represented particles containing 200 µg MH loaded in 100 µl agarose hydrogel. In order to remove free MH in hydrogel, HBSS was used to wash hydrogel 3 times. Every 10 minutes, HBSS was removed and replaced with fresh HBSS. UV absorbance at 245 nm was used to determine the amount of free MH released during each 10 minutes. After washing free MH, the HBSS was removed and replaced with fresh HBSS every 24 h for daily release. UV absorbance at 245 nm was used to determine the amount of MH released during each 24 hour period.

MH Release from DS/$Mg^{2+}$/MH Particles Embedded in Agarose Gel

Method 1 of particle encapsulation within the hydrogel led to the release of 25% MH on day 1, followed by slow sustained release up to 45 days (FIG. 8). Method 2 of particle encapsulation within the hydrogel led to the release of 16% MH on day 1, followed by slow sustained release up to 55 days. Method 2 resulted in a longer and more stable release of MH than method 1. In this study, DI water was used as the solvent for agarose gel. For quantification of MH release, 500 μl agarose hydrogel was transferred to microcentrifuge tubes and incubated with 500 μl of HBSS. Every 24 h, the HBSS was removed and replaced with fresh HBSS. The amount of MH released every 24 h was determined by UV absorbance at 245 nm.

FIG. 9 illustrates that MH was released from particle within the agarose hydrogel in DI water. In this study, 100 μl agarose hydrogel was used, and MH was released in 500 μl HBSS. Tripling the initial loading of MH only mildly increased the amount of MH released daily (although first an initial burst release of MH was observed) but greatly increased the duration of MH release from 12 days to 35 days. Similar result was obtained from agarose in HBSS (FIG. 10). In this study, MH release lasted for 11, 36 and 60 days when the initial loading was around 30, 90 and 180 μg respectively.

MH Release from Particles Doped with Chitosan or Gelatin Embedded in Agarose Gel FIG. 11 illustrates the result that, when particles were doped with positively charged polymer chitosan, MH release was much faster than from DS/$Mg^{2+}$/MH particles (FIG. 10). For example, MH release from DS/$Mg^{2+}$/MH particles lasted for 60 and 36 days at the loading of 180 and 90 μg, while the release from DS/$Mg^{2+}$/MH/chitosan particles only lasted 26 and 13 days at the loading of 200 and 100 μg. Thus, by adding chitosan high dose, fast release was achieved. For spinal cord injury, loss of grey matter is completed within 24 hours, and majority loss of white matter extends up to 7 days at the lesion center (Liu et al., 1997, J. Neurosci. 17(14):5395-5406; Ek et al., 2010, Plos One. 5 (8):e12021). MH is protective at high dose levels (15-75 μg/mL) (Garcia-Martinez et al., 2010, Biochem. Pharmacol. 79:239-50; Kraus et al., 2005, J. Neurochem. 94:819-27; Pi et al., 2004, J. Neurochem. 91:1219-30). Thus, a high dose release in the first six days from 2× loading can provide effective neuroprotection. The subsequence low dose release can target chronic inflammation.

FIG. 12 illustrates the finding that using gelatin type A to replace chitosan has similar effect on MH release. Collectively, FIGS. 10-12 illustrate the finding that the dose and duration of MH release can be adjusted by initial loading and doping positively charged polymers such as chitosan or gelatin type A.

Example 4: Controlled and Sustained Release of Minocycline from Nanoscale Coatings Mediated by Ion-Binding Interactions Materials DS (MW 500 kDa), MH and Gel A (GA) were obtained from Sigma-Aldrich. DS, MH, and GA was dissolved either in $CaCl_2$ solution, $MgCl_2$ solution, or deionized (DI) water. Concentrations of DS ranged from 1 µg/mL to 100 mg/mL. Concentrations of MH ranged from 0.01 mg/mL to 50 mg/mL. Concentrations of GA ranged from 0 to 100 mg/mL. Concentrations of $CaCl_2$ and $MgCl_2$ ranged from 0.1 mM to 4M. Polyethyleneimine (PEI) solution (50% w/v in water, Sigma-Aldrich) was diluted further with DI water up to 50% w/v.

Multilayer Growth

A substrate (either a 96-well UV plate or a silicon substrate) was first immersed in PEI solution for 10 min, and was subsequently rinsed in water for 1 min. The PEI-coated substrates were first immersed into a $DS/CaCl_2$ solution, followed by immersion into a $MH/CaCl_2$ solution, and then immersion into a $GA/CaCl_2$ solution. This process was continuously repeated over a 10 minute time period. Between immersions, the non-adsorbed polyelectrolyte was removed by rinsing the substrates with DI water for 1 min. This procedure was repeated to create multiple trilayer units of $DS+Ca^{2+}/MH(+Ca^{2+})/GA(+Ca^{2+})$. The same procedure was used to prepare $Mg^{2+}$-based LbL assemblies, with the DS, MH, and GA in solution with $MgCl_2$ instead of $CaCl_2$.

For characterization of the DS/GA LbL assembly, fluorescein isothiocyanate (FITC)-labeled GA was prepared as previously described (The et al., 1970, Immunology 18:865-873). Briefly, 100 mg GA were dissolved in 0.1 M sodium bicarbonate buffer (pH=9) at the concentration of 5 mg/mL, and 350 µl of a FITC solution (10 mg/mL in DMSO) were added dropwise while stirring. Unreacted FITC was removed by dialysis against DI, using a dialysis tubing with molecular weight cut off of 3,500.

MH loading was characterized by measuring absorbance at 245 nm using a plate reader (Tecan M200). To characterize the amount of GA incorporated in bilayer LbL assemblies of $DS(+Ca^{2+})/GA(+Ca^{2+})$, FITC-labeled GA was used. The fluorescent intensity of the labeled GA was measured using the same plate reader at an emission wavelength of 535 nm and excitation wavelength of 485 nm. The thickness of the LbL coatings was measured by optical profilometer (Zygo NewView 6000).

In Vitro MH Release Assay

To determine the release profile of MH in physiologically relevant conditions, samples were incubated at 37° C. in 100 µl Hanker's Balanced Salt Solution (HBSS, pH=7.4). Every 24 h, the HBSS was removed and replaced with fresh HBSS. The amount of MH released every 24 h was determined by UV absorbance at 245 nm.

Nitric Oxide Production

Bioactivity of released MH was studied using RAW264.7 macrophages and LPS stimulation assay. Macrophage cells were plated in individual wells of a 96-well culture plate and cultured for 48 h in 5% $CO_2$ atmosphere at 37° C. The culture was then subjected to 300 pg/mL LPS stimulation. Accumulation of nitrite ($NO_2^-$), as an indication of nitric oxide (NO) production by the macrophage cultures, was measured with Griess reagent (Promega, Madison, Wis.).

LbL Multilayer Film Growth: $Ca^{2+}$ LbL

Figure 14:
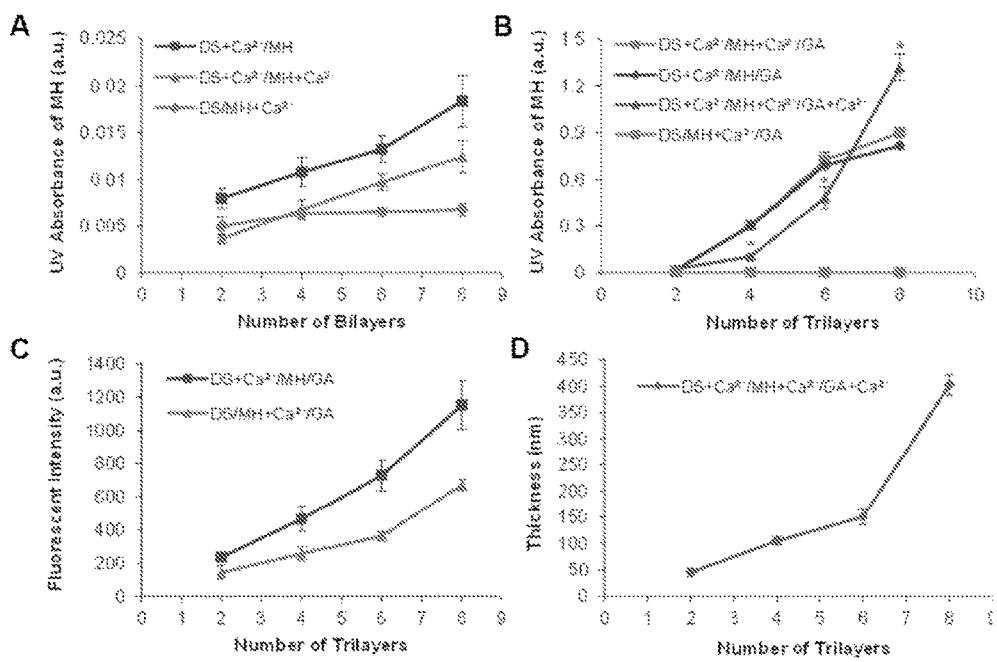
FIG. 14, comprising

FIG. 14A illustrates that UV absorbance at 245 nm corresponding to MH loading increased with the number of trilayer units when the concentration of $CaCl_2$ was 7.2 mM. FIG. 14B illustrates that for $(DS+Ca^{2+}/MH+Ca^{2+}/GA+Ca^{2+})_8$, the thickness of film increased linearly with the number of trilayer units deposited when $CaCl_2$ concentration was 3.6 mM, with an average trilayer unit thickness of 42 nm. When $CaCl_2$ concentration was 7.2 mM, the film had a slow linear growth in the first 6 trilayer units followed by a large increase of thickness at 8 trilayer units.

Loading of MH in $Ca^{2+}$ films

A study of the release of MH from the bilayer showed that only 1 µg/cm² MH was loaded in 8 bilayers of $(DS+Ca^{2+}/MH)$ films, indicating an inefficient LbL assembly. To solve this issue, a calcium binding-mediated MH loading mechanism was combined with an efficient LbL assembly design. DS could form electrostatic layer by layer (LBL) assembly with gelatin type A (GA), a positively charged biocompatible, biodegradable natural polymer derived from collagen. Multilayers of $DS/Ca^{2+}/MH$ conjugate/GA were successfully constructed to form hydrophilic nanoscale thin coatings. As illustrated in FIGS. 14A-14B, the UV absorbance of MH in multilayers of either $DS+Ca^{2+}/MH/GA$ (FIG. 14B, red line) or $DS+Ca^{2+}/MH+Ca^{2+}/GA$ (FIG. 14B, blue line) was greatly increased compared to that of the $DS+Ca^{2+}/MH$ (FIG. 14A, red line) or $DS+Ca^{2+}/MH+Ca^{2+}$ (FIG. 14A, blue line) multilayer films. It is noteworthy that the $(DS/MH+Ca^{2+}/GA)_8$ film failed to incorporate MH (FIG. 14B, green line) despite successful LbL film growth. The successful LbL film growth was indicated by increased fluorescence intensity from FITC-conjugated GA (FIG. 14C, green line). Although not wishing to be bound by any particular theory, this result suggests that the mechanism of MH loading resulted from a $Ca^{2+}$ binding interaction, rather than an electrostatic interaction.

The effect of adding $Ca^{2+}$ in GA layers on LBL film growth was examined FIG. 14C revealed that adding $Ca^{2+}$ in GA layer resulted in significantly lower UV absorbance at 4 and 6 trilayers, but significantly higher MH loading at 8 trilayers. Profilometry measurements (FIG. 14D) further demonstrated film growth with increased number of trilayers, with an average trilayer thickness of 50 nm for $DS+Ca^{2+}/MH+Ca^{2+}/GA+Ca^{2+}$ multilayers.

Effect of $Ca^{2+}$ in GA and MH Layers on MH Release

Figure 15:
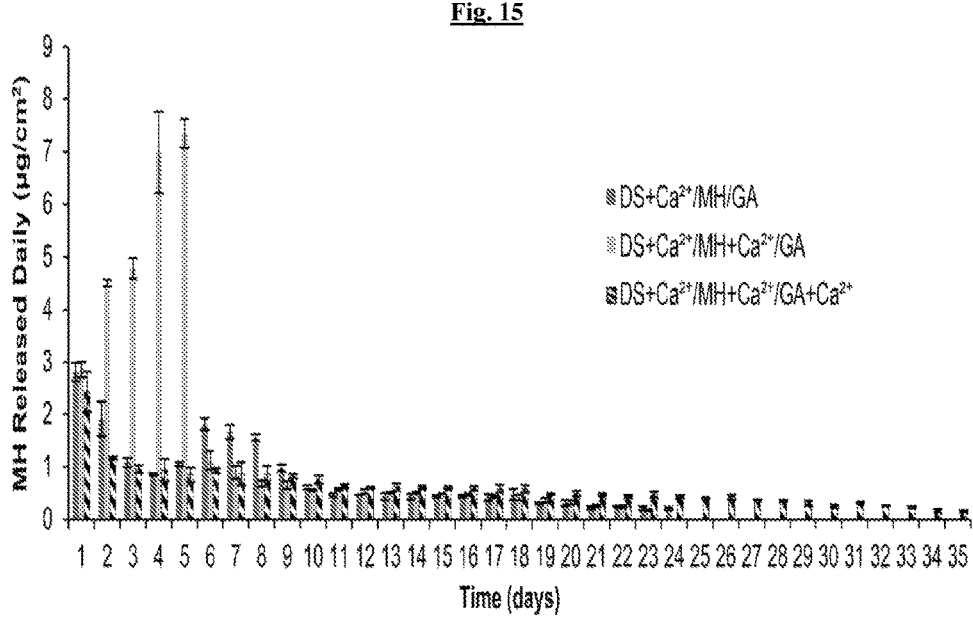
FIG. 15 is a graph illustrating the effect of $Ca^{2+}$ addition into different layers on MH mass released daily from eight trilayer units of LbL films.
Figure 16:
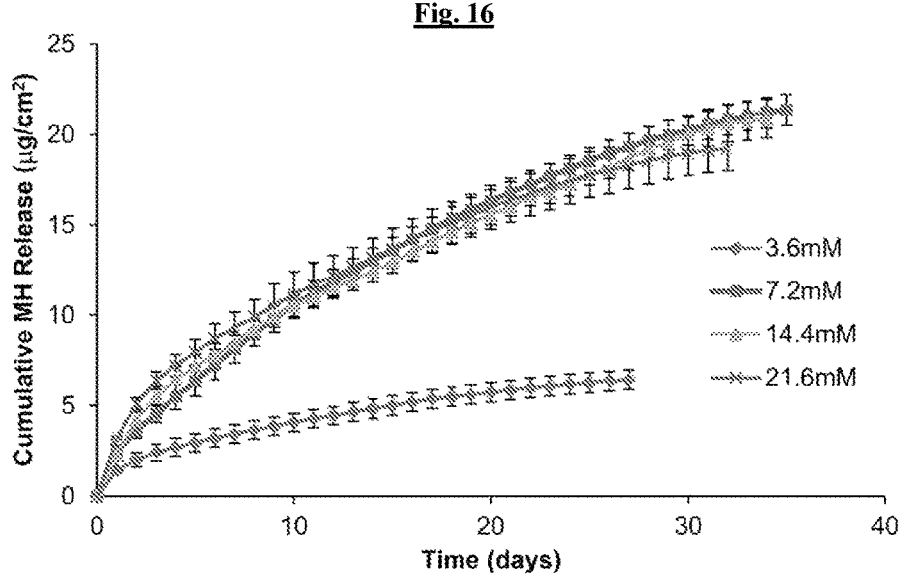
FIG. 16 is a graph illustrating the effect of $Ca^{2+}$ concentration on MH mass released daily from eight trilayer units of LbL assembly of $(DS+Ca^{2+}/MH+Ca^{2+}/GA+Ca^{2+})_8$.

MH released every 24 hours was collected, and the amount was determined by measuring UV absorbance at 245 nm FIG. 15 illustrates burst release for both conditions without $Ca^{2+}$ ions in the gel layers. Specifically, for $(DS+Ca^{2+}/MH/GA)_8$ there was an initial burst release during the first two days, and a second burst release between 6-8 days, followed by slow, stable release for over 24 days. Adding $Ca^{2+}$ in MH layers, but not GA layers, resulted in high initial burst during the first 5 days, followed by slow, stable release for over 21 days. MH release from $(DS+Ca^{2+}/MH+Ca^{2+}/GA+Ca^{2+}/)_8$ films showed low initial burst, and slow, stable release for over 35 days without second burst release (FIG. 16). Although not wishing to be bound by any particular theory, this result suggests that the binding of MH is more stable in these LbL assemblies, possibly because adding $Ca^{2+}$ in GA layers can increase the amount of $Ca^{2+}$ ions in the LBL films and thereby increases the capability of the film to attract MH. The versatile release behavior mediated by $Ca^{2+}$ binding can potentially be used in various pathological situations.

Effect of $Ca^{2+}$ Concentration on Film Growth and MH Release 3.6 mM, 7.2 mM, and 14.4 mM $Ca^{2+}$ in polyelectrolyte and MH solutions were added for LbL assembly, and adding 3.6 mM $Ca^{2+}$ in the solutions of all three layers resulted in highest MH loading and the longest release. In addition, the burst release of MH on the first day was much higher for 3.6 mM than 7.2 mM $Ca^{2+}$ (FIG. 15).

Effect of Initial Loading (Number of Trilayer Units) on MH Release

Figure 17:
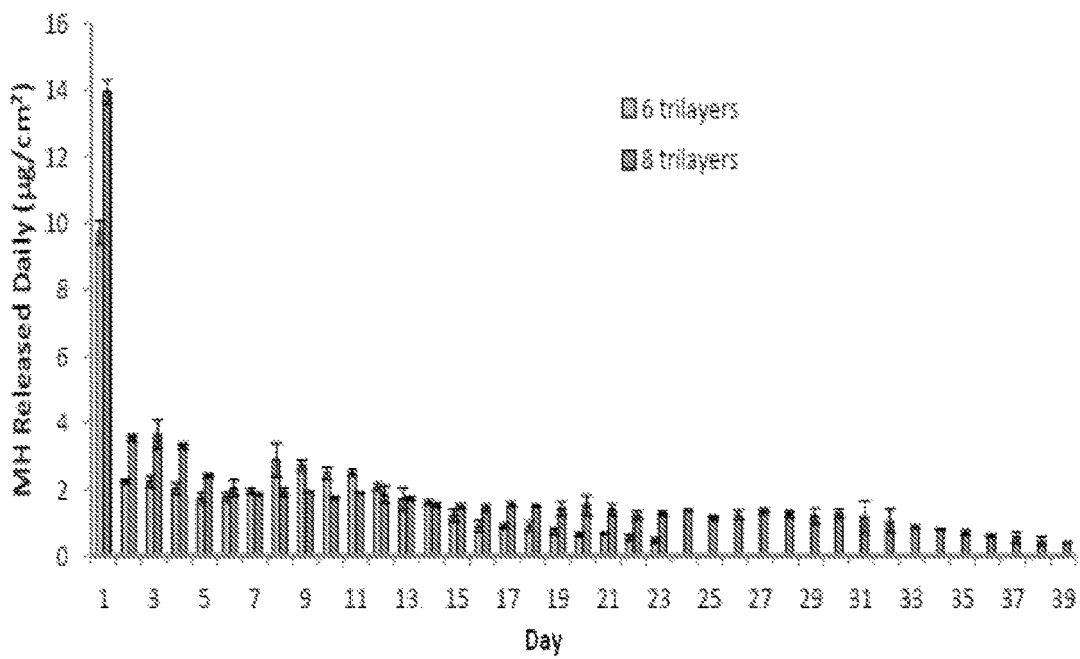
FIG. 17 is a graph illustrating the effect of initial loading on MH mass released daily from six and eight trilayer units of LbL assembly of $(DS+Ca^{2+}/MH+Ca^{2+}/GA+Ca^{2+})$ respectively, when $Ca^{2+}$ concentration was 3.6 mM.

FIG. 17 illustrates that increasing the number of trilayer units from six to eight increased mass of MH released every day, and prolonged drug release from 23 days to 39 days when $Ca^{2+}$ concentration was 3.6 mM.

Effect of pH on MH Release

Figure 18:
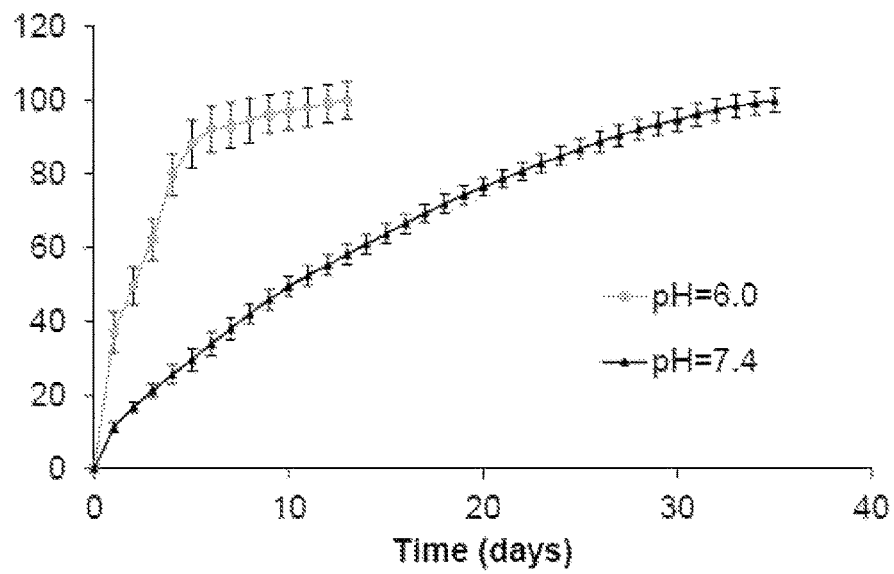
FIG. 18 is a graph illustrating pH-responsive release of MH from $Ca^{2+}$-based LbL film.

Reduced extracellular pH (tissue acidosis) is commonly found under pathophysiological conditions such as tissue injury, infection, or inflammation. To simulate pathological and physiological conditions, HBSS with pH of 6.0 and 7.4 was used as the release media. MH release only lasted 13 days at pH 6.0, with a high initial burst release, versus 35 days of sustained release and a small burst release at physiological pH (FIG. 18). These results suggest that $Ca^{2+}$ binding-mediated MH release is pH-sensitive, possibly because reduced pH can weaken the chelation between MH and DS-bound $Ca^{2+}$ and facilitate MH release.

Bioactivity of Released MH

Figure 19:
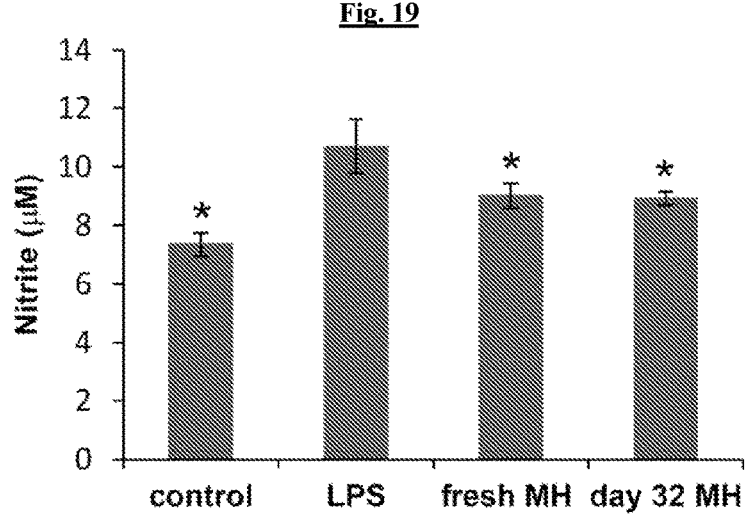
FIG. 19 is a graph illustrating nitrite production by macrophage treated with LPS, LPS and fresh MH (1 µg/mL), or LPS and MH released on day 32 (diluted to 1 µg/mL). Cells without any treatment were used as control. *$P<0.05$ compared with LPS-treated culture.

Bioactivity of released MH was studied using RAW264.7 macrophages. The cells were stimulated with lipopolysaccharide (LPS) for upregulation of nitric oxide (NO), a potent inflammatory mediator and neurotoxic molecule. MH released during a 24 hour period on day 32 was diluted to 1 µg/mL respectively, and added to macrophage cultures together with LPS. LPS and 1 µg/mL fresh MH were used as controls to compare the bioactivity with released MH. FIG. 19 illustrates that LPS treatment significantly increased NO production in macrophages, both fresh MH and MH released on day 32 significantly reduced NO production, and there was no significant difference between the NO level in fresh MH and released MH treated cultures at the same MH concentrations. This suggests that released MH has same bioactivity as fresh MH.

Antibacterial and Antibiofilm Property of the LbL Coating

Figure 20:
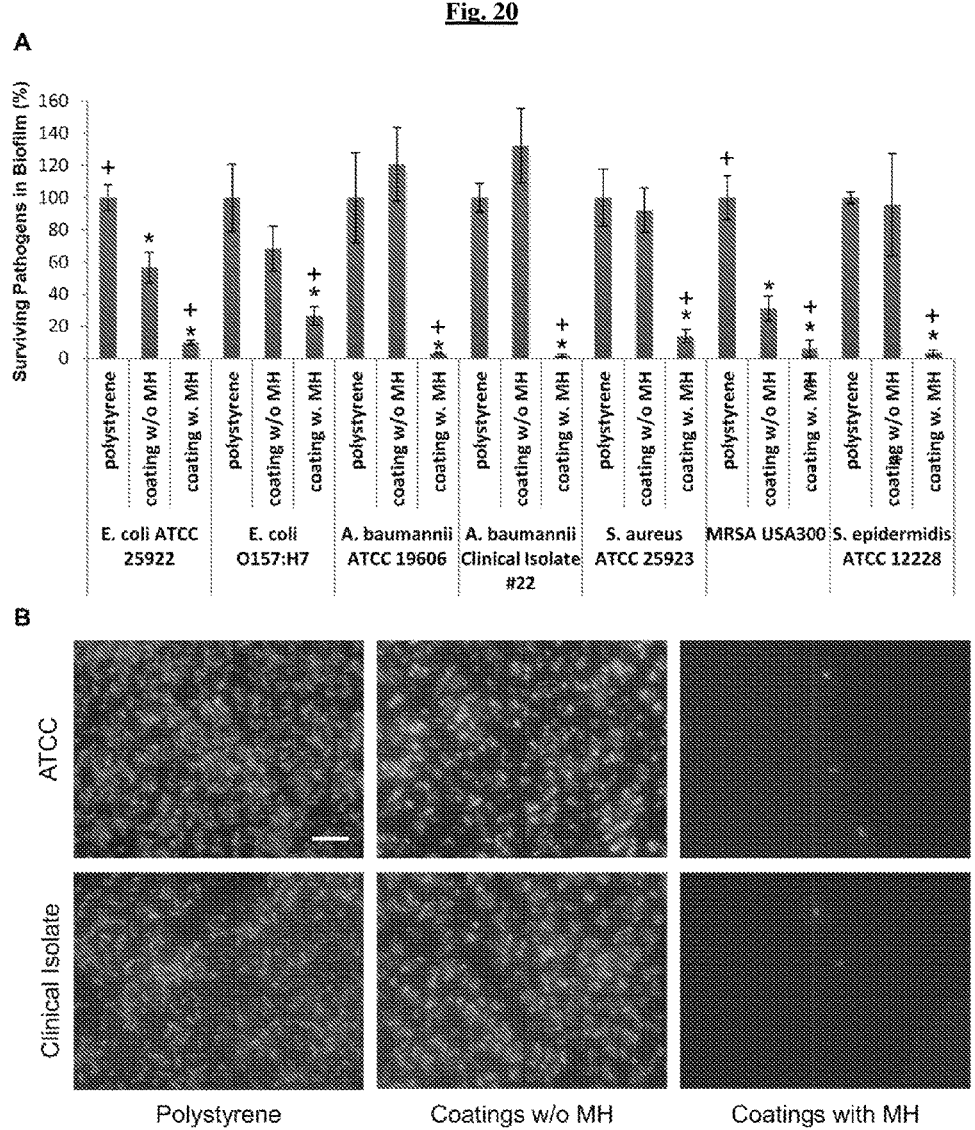
FIG. 20, comprising

To evaluate the antibacterial and antibiofilm efficacies of this novel coating, we selected seven bacterial species that are known to be involved in implant-associated infection, including a multi-drug resistance *Acinetobacter baumannii* clinical isolate that was locally isolated from our hospitalized patient having invasive device-associated infection. The biofilm assays were carried out using 1 day biofilms which are normally recommended for early matured biofilms. FIG. 20 demonstrates that coatings incorporating MH significantly inhibited biofilm formation of all seven virulent pathogens, leaving negligible pathogens in biofilm. Often, such non-significant numbers are cleared by body's defense system.

$Mg^{2+}$-Mediated MH Release $Ca^{2+}$ binding-mediated MH release from nanoscale LbL films can last at least 39 days. In addition, $Mg^{2+}$ ions may be used to replace $Ca^{2+}$ ions as both DS and MH have high binding affinity to $Mg^{2+}$ as well. In certain embodiments, $Mg^{2+}$ is a good choice for neural implant coatings, because $Mg^{2+}$ is neuroprotective. In other embodiments, $Ca^{2+}$ is a good choice for orthopedic applications.

LbL Multilayer Film Growth: $Mg^{2+}$

Figure 21:
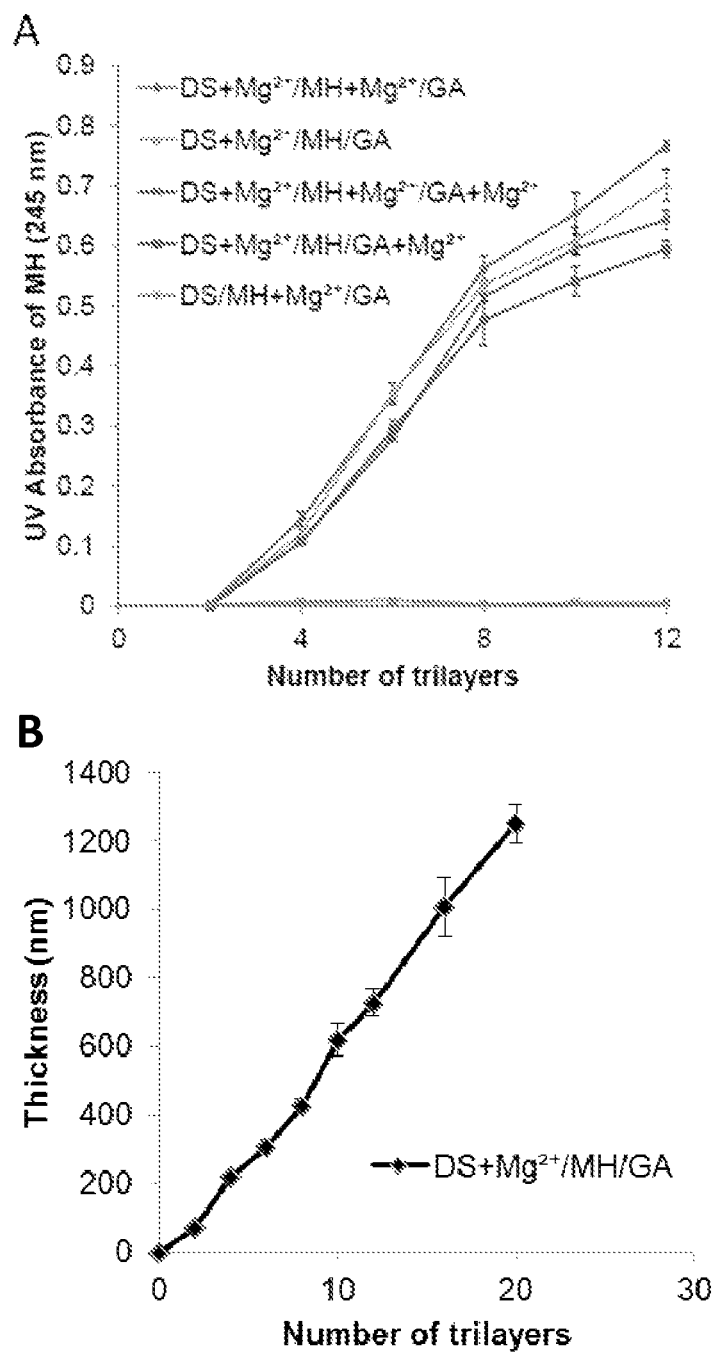
FIG. 21, comprising

FIG. 21A illustrates that MH loading increased with the number of trilayer units when the concentration of $MgCl_2$ is 7.2 mM, suggesting that $Mg^{2+}$ binding can mediate MH loading and release from LbL films as well. FIG. 21B illustrates that for $(DS+Mg^{2+}/MH+Mg^{2+}/GA)_8$ the thickness of film increased linearly with the number of trilayer units deposited, with an average trilayer unit thickness of 64 nm.

Effect of $Mg^{2+}$ in GA and MH Layers on MH Release

Figure 22:
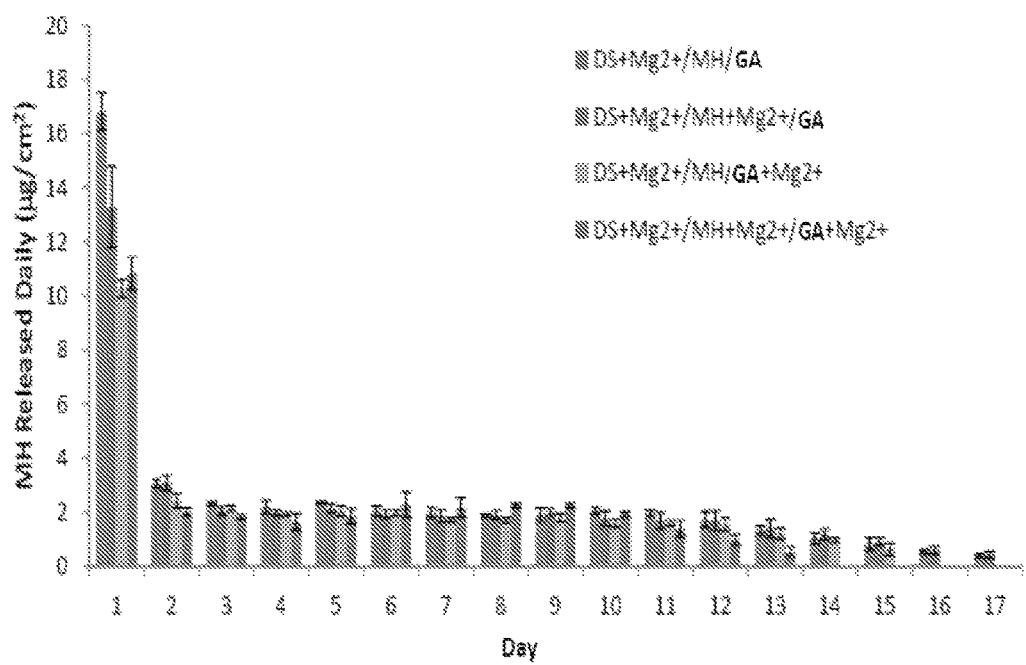
FIG. 22 is a graph illustrating the effect of adding $Mg^{2+}$ (7.2 mM) on MH mass released daily from 8 trilayer units of LbL films. In each data set, the data points refer to, respectively, $DS+Mg^{2+}$/MH/GA; $DS/Mg^{2+}$/MH+$Mg^{2+}$/GA; $DS+Mg^{2+}$/MH/GA+$Mg^{2+}$; and $DS+Mg^{2+}$/MH+$Mg^{2+}$/GA+$Mg^{2+}$.

MH released every 24 hours was collected and the amount was determined by measuring UV absorbance at 245 nm FIG. 22 illustrates that adding $Mg^{2+}$ in the GA layer resulted in less mass release every day and shorter release period. As GA does not have binding affinity to $Mg^{2+}$ ion, adding $Mg^{2+}$ in GA solution during LbL assembly does not increase the amount of $Mg^{2+}$ ions in the coatings. When there was no $Mg^{2+}$ in GA layers, adding $Mg^{2+}$ in MH layers showed similar release profile as no $Mg^{2+}$ in MH layers, except that the first day release was significantly higher.

Effect of $Mg^{2+}$ Concentration on MH Loading and Release

Figure 23:
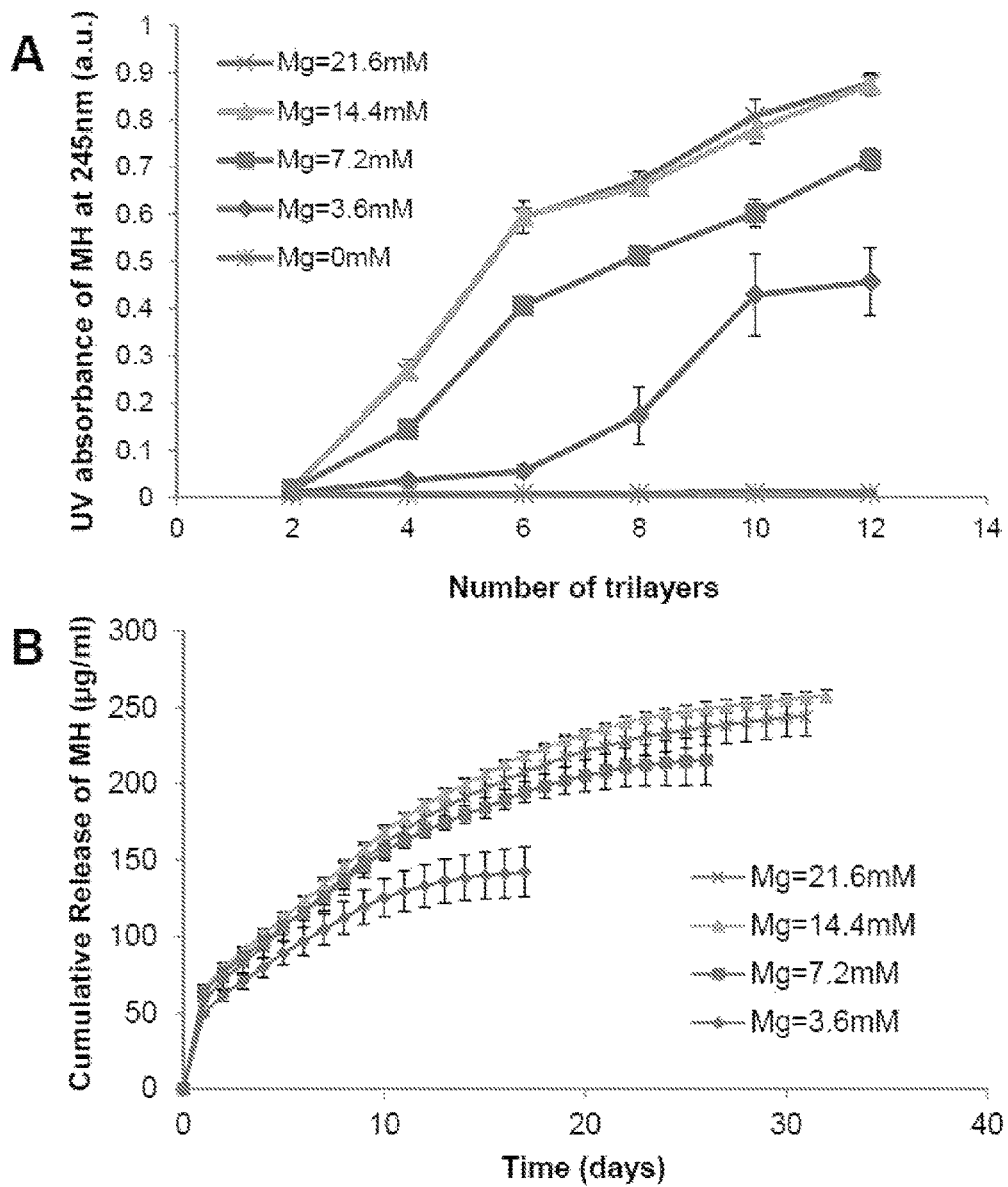
FIG. 23, comprising

As MH loading is mediated by $Mg^{2+}$, the concentration of $Mg^{2+}$ in various layers is critical for MH loading. For example, the addition of $Mg^{2+}$ in the DS layers is critical for LBL formation. FIG. 23A illustrates the absorbance of MH in LBL assembly increased greatly when $Mg^{2+}$ concentration in DS layers increased from 0 to 14.4 mM. Additionally, MH absorbance reached a maximum when $Mg^{2+}$ concentration reached 14.4 mM, indicating that $Mg^{2+}$ concentrations above 14.4 mM were excessive. However, unlike the DS layer, $Mg^{2+}$ added in the MH layer had an insignificant effect on the loading of MH in LBL assembly. $Mg^{2+}$ in the gelA layer actually had a negative effect, as free $Mg^{2+}$ in the gelA solutions may interact with the bound MH, causing it to release from the DS and diffuse away. The release of MH from the LBL was also dependent on the $Mg^{2+}$ in DS layers. As illustrated in FIG. 23B, 257.6 µg/cm² of MH was released in 32 days from the LBL with 14.4 mM $Mg^{2+}$ added in DS layers. Higher $Mg^{2+}$ concentration in DS layers increased the amount of $Mg^{2+}$ incorporated in LBL, thus increased the amount of released MH and prolonged the release duration.

Effect of Initial Loading (Number of Trilayer Units) on MH Release

Figure 24:
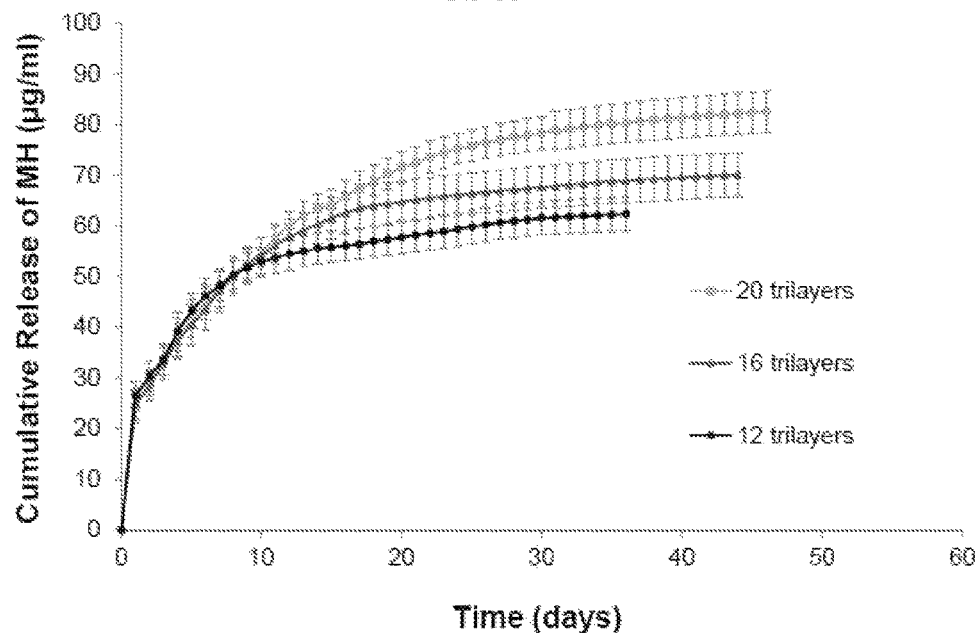
FIG. 24 is a graph illustrating the effect of initial loading on MH mass released daily from 12, 16, and 20 trilayers of LbL assembly of ($DS+Mg^{2+}$/MH+$Mg^{2+}$/GA+$Mg^{2+}$) respectively when $Ca^{2+}$ concentration was 7.2 mM.

FIG. 24 illustrates that increasing the number of trilayer units from 12 to 20 increased mass of MH released every day, and prolonged therapeutic agent release from 36 days to 46 days for $(DS+Mg^{2+}/MH+Mg^{2+}/GA+Mg^{2+})$ when $Mg^{2+}$ concentration was 7.2 mM. The initial loading of MH could be controlled by varying the number of trilayers. The total release of MH increased from 55 to 99 µg/cm² when the number of trilayers increased from 12 to 24.

Effect of pH on MH Release

Figure 25:
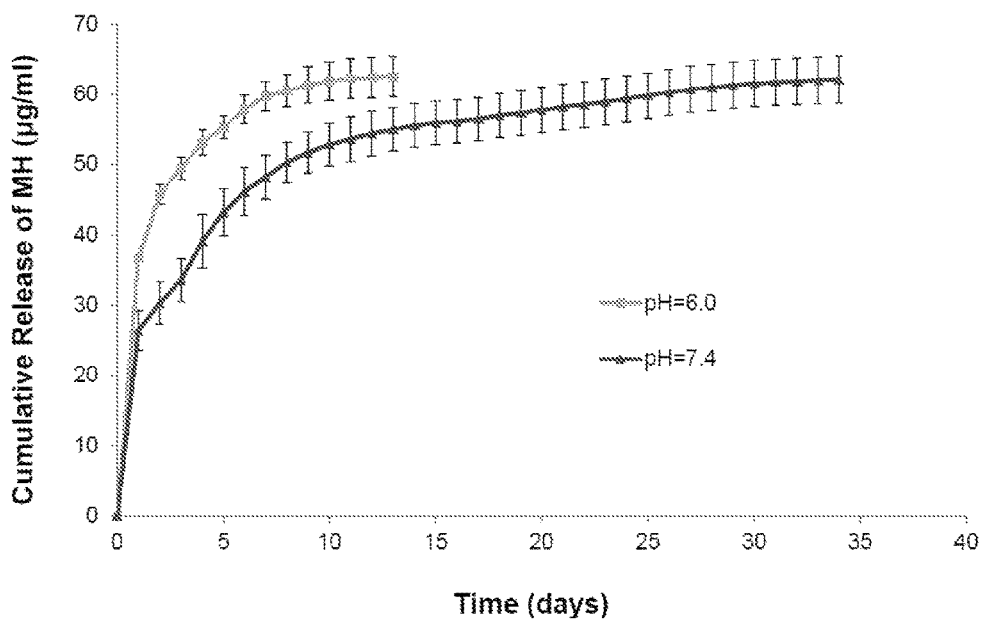
FIG. 25 is a graph illustrating pH-responsive release of MH from $Mg^{2+}$-based LbL film.

FIG. 25 illustrates that MH release from Mg based LbL films is pH-responsive as well. To simulate pathological and physiological conditions, Hank's Balanced Salt Solution (HBSS) with pH of 6.0 and 7.4 were used as the release medium. As illustrated in FIG. 25, MH release lasted only 13 days at pH 6.0, with a higher initial burst release, versus 33 days of sustained release and a smaller burst release at pH 7.4. This result illustrates that $Mg^{2+}$-mediated MH release is pH-sensitive; MH exhibits an accelerated release rate at pathological pH.

Anti-Inflammatory Activity of Released MH

Anti-inflammatory of released MH was studied using RAW264.7 macrophages (FIG. 26). The cells were stimulated with lipopolysaccharide (LPS) for upregulation of nitric oxide (NO), a potent inflammatory mediator and neurotoxic molecule. MH released during a 24 h period on day 45 from a 16-trilayer unit LbL assembly with the layers $(DS+Mg^{2+}/MH+Mg^{2+}/GA+Mg^{2+})$ was diluted to 0.5 µg/mL and added to macrophage cultures together with LPS. LPS and 0.5 µg/mL fresh MH were used as controls to compare the bioactivity between the fresh MH and the MH released from the MH/DS/$Mg^{2+}$ complex. FIG. 26 illustrates that, while macrophages treated with LPA exhibited significantly increased NO production, both fresh MH and MH released on day 45 exhibited significantly reduced NO production. No significant difference was observed between the NO level in cultures treated with fresh MH and the NO level in cultures treated with MH released from the MH/DS/Mg$^{2+}$ complex when the same concentration of MH was used. This result supports the hypothesis that MH released from the MH/DS/Mg$^{2+}$ complex has same bioactivity as fresh MH.

Neuroprotective Activity of Released MH in Mg LbL Assembly

Neuroprotective activity of released MH was studied using primary rat neurons. The cells were stimulated with non-heat inactivated fetal bovine serum, which was toxic to neurons. MH released during the first 24 hr period was diluted to 80 and 40 µg/mL and added to serum-treated neuron cultures. 40 mg/mL fresh MH was used as a control. The number (FIG. 27A) and images (FIG. 27B) of survival cells showed that non-heat inactivated serum induced loss of neurons, while both fresh and released MH inhibited serum-induced neuron loss. There was no significant difference between fresh and released MH, indicating that released MH and fresh MH are equally neuroprotective.

Mechanism of MH Loading in LbL Assembly

Figure 13:
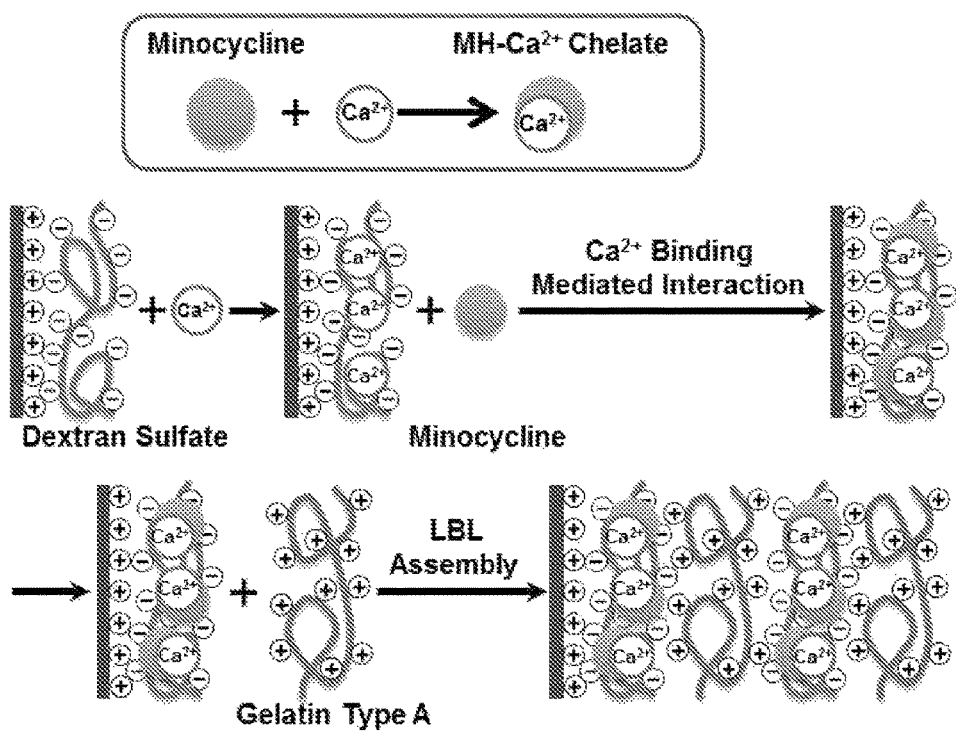
FIG. 13 illustrates the mechanism of $Ca^{2+}$-mediated or $Mg^{2+}$-mediated MH attachment to DS and LbL assembly.

A novel mechanism for MH loading and release was herein discovered: metal ion binding-mediated interaction as illustrated in FIG. 13 with Ca$^{2+}$. Metal ions can be used as linkers to attach MH to DS or other polymers (CS, heparin, HA, alginate, alginate sulfate, and the like) that have high binding affinity to metal ions. Then, a cationic polymer such as gelatin type A can be used to form LbL assemblies with DS or other polymers. The metal ion-mediated interaction appears to be stronger than electrostatic adsorption, as evidenced by (i) the increase of loading potential when Ca$^{2+}$ was first adsorbed to the DS layer, and (ii) the prolonged release profile of MH as compared with small molecule release from previous LbL assemblies; release of small molecules based solely on electrostatic interaction is generally very fast (on the scale of hours), as opposed to the 35+ day release presented herein. The presently described mechanism for loading and release of small molecular therapeutic agent may be potentially applied to the therapeutic agents that have high binding affinity with metal ions.

The LbL assembly method depicted may also be easily modified to control the release kinetics leveraging the calcium mediated interaction. In the early stage of release process, initial and second burst releases were observed from different formulation of LbL assembly (FIG. 15). A weak initial burst release was obtained in LbL film of DS+Ca$^{2+}$/MH+Ca$^{2+}$/GA+Ca$^{2+}$, a strong initial burst release was obtained in LbL film of DS+Ca$^{2+}$/MH+Ca$^{2+}$/GA, and both of initial and second burst were obtained in LbL film of DS+Ca$^{2+}$/MH/GA. This result suggested that addition of Ca$^{2+}$ into different layers can efficiently influence the release kinetics of MH.

After the initial burst, the release kinetics was close to zero-order, and stable release continued for over 3 weeks. Therefore, this Ca$^{2+}$-mediated LbL coating may be used where either stable sustained release or pulsed release is required. In addition, release profile with additional profiles of burst release and long-term stable release may be obtained by coating different formulation of LbL films together, enabling *facile* development of a versatile coating with required release kinetics.

In addition, the initial loading of MH may be simply controlled by the number of multilayer units. The initial loading influenced the mass release rate of MH, but did not influence the near zero-order release kinetics after the initial burst release in the first day. This suggests mass release rate may be tuned by the number of trilayer units without changing the release kinetics.

The hypothesis that the release rate is influenced by the competitive binding of DS by Ca$^{2+}$ and Na$^+$ was supported by experiments where pH was found to influence the release kinetics: the release rate was increased in lower pH. This may be because the binding affinity of MH for Ca$^{2+}$ decreases at low pH. The tissue pH may be as low as 5.0 during severely inflammatory conditions. Under such condition, the release rate of MH is increased to redress the inflammation. Thus, this pH-sensitive coating characteristic of LbL assembly of the invention may be applied as a smart coating responsive to inflammation.

An issue for the delivery of MH is its stability, and the decomposed MH can be harmful to cells. In the present study, it was found that MH loaded in LbL assembly retained its bioactivity even after 35 days, when MH was terminally released, without release of toxic degradation products.

In summary, MH was loaded in the LbL assembly leveraging metal ion-mediated interaction. Ca$^{2+}$ had significant effects on the loading and release kinetics of MH and enabled easy customization of coordinated MH release. The burst release may be tuned by adding Ca$^{2+}$ into distinct layers, and the mass release rate of MH may be controlled by changing the number of trilayer units, both without changing the steady state release kinetics. This kind of LbL film was also pH sensitive, promoting the release of MH in low pH environments that are usually found in inflamed tissue, thus establishing a novel mechanism for drug delivery. A similar effect was observed for Mg ions, and other metal ions (Zn,Fe,Cu) may be used to attach therapeutic agents to polymers as well as long as both therapeutic agents and polymers have high binding affinity to metal ions.

Example 5: Formation of LbL Assemblies Comprising Therapeutic Agent/Polyanion/Metal Ion Complexes Described herein is the development of novel LbL assemblies comprised of therapeutic agent/polyanion/metal ion complexes. One molecule of MH can chelate two Mg$^{2+}$ ions, which are in turn chelated to DS, to induce intra- and intermolecular crosslinking of DS molecules which leads to the formation of MH/DS/Mg$^{2+}$ complexes. The addition of polyvalent metal ions to DS in the absence of MH did not induce any crosslinking, either intramolecularly or intermolecularly. Also described herein is the successful formation of LbL assemblies comprising a variety of metal ions, polymers, and therapeutic agents. Although not wishing to be bound by any particular theory, these results suggest that any metal ion, polymer, or therapeutic agent may be useful to form therapeutic agent/polyanion/metal ion complexes, provided that both the polymer and the therapeutic agent has a high binding affinity to the metal ions.

Materials

Gelatin type A (GA), poly(ethylene imine) (PEI), DS, heparin, chondroitin sulfate (CS), hyaluronic acid (HA), alginate, MH, tetracycline, and ciprofloxacin were obtained from Sigma-Aldrich. Polyvalent metal ions (Ca$^{2+}$, Mg$^{2+}$, Zn$^{2+}$, Fe$^{2+}$, Ni$^{2+}$, and Cu$^{2+}$) were dissolved in DI water, providing solutions of metal ions at concentrations ranging between 0.1 mM to 4 mM of metal ions. Polyanions (DS, heparin, CS, HA and alginate) were dissolved in DI water to provide solutions of polyanions at concentrations ranging between 0.01 mg/mL to 100 mg/mL. Polyanions were also dissolved in the solutions of metal ions to provide solutions comprised of both a polyanion and a metal ion. Therapeutic agents (MH, tetracycline, and ciprofloxacin) were dissolved in DI water to provide solutions of drugs at concentrations ranging from 0.01 mg/mL to 50 mg/mL. Therapeutic agents were also dissolved in the solutions of metal ions to provide solutions comprised of both a therapeutic agent and a metal ion. One equivalent of hydrochloric acid was added to the ciprofloxacin solution to assist the dissolution of the ciprofloxacin. Solution of GA was prepared by dissolving GA into DI water to provide solutions of GA at concentrations ranging from 0 mg/mL to 100 mg/mL. GA was also dissolved in the solutions of metal ions to provide solutions comprised of both a gelatin and metal ion.

Multilayer Growth

A substrate (either a 96-well UV plate or a silicon substrate) was first immersed in PEI solution, and was subsequently rinsed in water. The PEI-coated substrates were first immersed into a polyanion/metal ion solution, then immersed into either of a therapeutic agent solution or a drug/metal ion solution, and then immersed into either a gelatin solution or a gelatin/metal ion solution. This process was continuously repeated over a 10 minute time period. Between immersions, the non-adsorbed polyanion was removed by rinsing the substrates comprised of the LbL assembly with DI water for 1 min. This procedure was repeated to create multiple bilayer or trilayer units of polyanion+metal ion/therapeutic agent (with or without metal ion)/gelatin or equivalent polymer (with or without metal ion) DS+metal ion/MH(+Metal ion)/gelatin or equivalent polymer (+metal ion). In certain embodiments, metal ions are added to the DS solution to successfully produce LbL assemblies. Metal ions do not have to be added to the MH solution or the GA solution in order for the layers of the LbL assembly to form, but whether or not a metal ion is present in the MH solution or the GA solution affects the rate at which a therapeutic agent is released from the LbL assembly.

The absorbance of the therapeutic agents were characterized by Tecan plate reader.

Effects of Polyanions, Metal Ions and Therapeutic Agents on the Formation of LbL Assemblies LbL assemblies were not formed in the absence of metal ions. The absorbance of drug within the LbL assembly increased as the number of trilayers increased. A number of combinations of metal ions, therapeutic agents, and polyelectrolytes were found to provide LbL assemblies (Table 2).

TABLE 2

Conditions for the formation of LbL assemblies (N/A* indicates the alginate was crosslinked by $Ca^{2+}$, $Zn^{2+}$, or $Cu^{2+}$ to form a hydrogel)

| Polyanions | Metal ions | | | | | |
|---|---|---|---|---|---|---|
| | $Ca^{2+}$ | $Mg^{2+}$ | $Zn^{2+}$ | $Fe^{2+}$ | $Ni^{2+}$ | $Cu^{2+}$ |
| Formation of LbL Assembly with Minocycline/Polyanion/Metal Ion Complex | | | | | | |
| Dextran sulfate | Yes | Yes | Yes | Yes | Yes | Yes |
| Heparin | No | No | No | No | No | No |
| Chondroitin sulfate | Yes | Yes | Yes | No | Yes | Yes |
| Hyaluronic acid | No | No | No | No | Yes | Yes |
| Alginate | N/A* | No | N/A* | No | Yes | N/A* |
| Alginate sulfate | Yes | Not tested | Not tested | Not tested | Not tested | Not tested |
| Formation of LbL Assembly with Tetracycline/Polyanion/Metal Ion Complex | | | | | | |
| Dextran sulfate | Yes | Yes | Yes | Yes | Yes | Yes |
| Heparin | No | No | No | No | No | No |
| Chondroitin sulfate | No | No | No | No | Yes | Yes |
| Hyaluronic acid | No | No | No | No | No | No |
| Alginate | N/A* | No | N/A* | No | Yes | No* |
| Formation of LbL Assembly with Ciprofloxacin/Polyanion/Metal Ion Complex | | | | | | |
| Dextran sulfate | Yes | Yes | Yes | Yes | Yes | Yes |
| Heparin | No | No | No | No | No | No |
| Chondroitin sulfate | Yes | Yes | Yes | No | Yes | Yes |
| Hyaluronic acid | No | No | No | No | No | No |
| Alginate | N/A* | No | N/A* | Yes | No | N/A* |

Effects of Therapeutic Agents on Therapeutic Agent/Polyanion/Metal Ion Complex Formation In the absence of a therapeutic agent, the polyanion and the metal ion failed to form a complex. The families of therapeutic agents that can be used to form particles include, but are not limited to, chemotherapeutic agents, tetracycline antibiotics, and quinolones. Chemotherapeutic agents include doxorubicin, derivatives and analogs thereof, including any other anthracycline antibiotic that is used in treating or preventing cancer. Tetracycline antibiotics are a group of broad-spectrum antibiotics that are generally used in the treatment of infections. Quinolones are a family of synthetic broad-spectrum antibacterial drugs that can be used in the treatment of various serious bacterial infections. Besides these families of drugs, anthracenediones, anthracyclines, and statins are potentially useful in the formation of particles. Anthracenedione can be used in antimalarial medication or chemotherapy. Anthracyclines are a family of chemotherapy drug that can be used to treat cancer. Statins are a family of drug used for reducing cholesterol levels for the prevention of cardiovascular diseases.

Example 6: Combined MH-Releasing, Anti-Adhesion LbL Coating for Medical Implants, Including Urinary Catheters Patients with permanent injury or severe illness may need a long term use of urinary catheters. Catheter insertion and long-term catheterization carries a significant risk of catheter-associated urinary tract infection (CAUTI) and inflammatory reaction around inner urethra. Novel antibacterial, anti-inflammatory, and anti-adhesive coatings based on layer-by-layer (LbL) assembly are herein disclosed for effective prevention of infection and inflammation associated with urinary catheters.

In certain embodiments, a novel anti-bacterial, anti-inflammatory LbL coating impregnated with minocycline hydrochloride (MH), an antibiotic and anti-inflammatory drug, on this base layer is provided. MH may be incorporated in the LbL assembly based on a novel calcium binding-mediated interactions, which in combination with protective LbL layers, allows sustained release of MH in urine for over 33 days. In particular, initial colonization of three CAUTI related bacterial biofilm, Escherichia coli (E. coli), Acinetobacter baumannii (A. baumannii) and Staphylococcus aureus (S. aureus), was significantly inhibited on catheters coated by MH-releasing LbL coating.

Additionally, anti-adhesive LbL coating was developed by alternate adsorption of anti-adhesive poly(l-glutamic acid)-grafted-poly(ethylene glycol) (PGA-g-PEG) and gelatin. Even though PGA-g-PEG/PLL (poly-L-lysine) may have anti-adhesive properties, PLL is not biocompatible, and thus in the present study PGA-g-PEG/gelatin type A (GA) was used. As demonstrated herein, the adhesion of bovine serum albumin, bacteria, and macrophages on eight bilayers of PGA-g-PEG/GA was greatly reduced. By combining the two coatings together, no bacteria were observed on the combined antimicrobial, anti-adhesive coating.

Materials

Poly(ethyleneimine) solution (PEI, 50% w/v), poly(sodium 4-styrenesulfonate) (PSS), dextran sulfate (DS), minocycline hydrochloride (MH), gelatin type A (GA), alginate, glycol chitosan (GC), 1,1'-carbonyldiimidazole (CDI), ethylenediamine (EDA), poly(ethylene glycol)methyl ether (Me-PEG-$NH_2$), N-hydroxysuccinimide (NHS) and sodium tetraborate were purchased from Sigma-Aldrich. Formamide and chlorosulfuric acid were purchased from Alfa Aesar. 1-Ethyl-3-[3-dimethylaminopropyl]carbodiimide hydrochloride (EDC) was purchased from Pierce. Calcium chloride was purchased from Fisher. Acetone was purchased from BDH chemicals. PVC catheters were obtained from C.R. Bard, Inc (Covington, Ga.).

Preparation of PGA-g-PEG

PEG-$NH_2$ Conjugate:

200 mg PEG were dissolved in 10 mL dimethylformamide (DMF), and 323 mg 1,1'-carbonyldiimidazole were mixed in the solution. The reaction was stirred for 2 h at room temperature. Subsequently, 5 mL of ehylenediamine were added and the reaction was allowed to proceed with stirring for 24 h at room temperature. 10 mL deionized (DI) water were added to stop the reaction and the reaction mixture was dialyzed against DI water for at least 18 h with at least 3 buffer changes. The product was lyophilized and stored at −20° C.

Graft PEG onto PGA:

40 mg of PGA, 95.2 mg of PEG-$NH_2$ and 2 mg of NHS were dissolved in 2 mL of buffer, 100 mM sodium tetraborate (pH=8.5). EDC (14.6 mg) was dissolved in the mixture with stirring. The reaction was allowed to proceed at room temperature for 6 h. After filtration, the reaction mixture was dialyzed for 24 h, first against phosphate buffer (0.1 M, pH=7.4, $Na_2HPO_4/NaH_2PO_4$) and subsequently against DI water. PEG-PGA was lyophilized and stored at −20° C.

Fabrication of Alginate Sulfate

Alginate sulfate (AS) was prepared as reported (Ronghua et al., 2003, Carbohydrate Pol. 52:19-24). Briefly, 2 g alginate were mixed with 16 mL formamide with stirring. 4 mL Chlorosulfuric acid were added to the mixture, which was kept at 60° C. for 4 hours. This solution was diluted by 100 mL acetone, and the precipitate was re-dissolved in DI water. The pH of redissolved solution was adjusted to pH 10-11 by 0.1N NaOH, and the solution was dialyzed against DI water for 72 hours. DI water was changed twice during dialysis. After dialysis, solution was lyophilized to get AS powder.

LbL Assembly of Initiating Base Layer

PEI solution was diluted in deionized (DI) water to the concentration of 1 mg/mL. PSS was dissolved in DI water at the concentration of 1 mg/mL. Substrates (or catheters) were immersed in PEI and PSS solution or 10 min alternatively. The excess molecules were removed by rinsing the catheters with DI water for 1 min between each step. LbL of $(PEI/PSS)_{10}$+PEI was used as the positively charged initiating layers for subsequent LbL assembly.

LbL Assembly of MH-Releasing Multilayer Film 1 mg/mL solutions of DS, MH, GA, AS and GC were prepared in 0.8 mg/mL $CaCl_2$ in deionized (DI) water solution. The substrates (UV plate or PVC urinary catheter) were first coated with 10 bilayers of PEI/PSS as an initiating positively charged base layer, followed by alternating immersion in solutions of DS, MH, GA, AS and GC for 10 min. The excess molecules were removed by rinsing the substrates with DI water for 1 min between each step.

LbL Assembly of Anti-Adhesive Multilayer Film

Anti-adhesive multilayer films were deposited on PVC catheters. 1 mg/mL solutions of PGA-g-PEG and GA were prepared in 0.8 mg/mL $CaCl_2$ in DI water solution. The substrates were first coated with 10 bilayers of PEI/PSS as an initiating positively charged base layer, followed by alternating immersion in solutions of PGA-g-PEG and GA for 10 min. The excess molecules were removed by rinsing the substrates with DI water for 1 min between each step.

LbL Assembly of MH-Releasing, Anti-Adhesive Multilayer Film

A combined coating consists of imitating layers, therapeutic agent-releasing coating and anti-adhesive coating. The formula of combined coating is $(PEI/PSS)_{10}$+PEI+$(DS/MH/GA/AS/GC)_{24}$+$(PGA-PEG/GA)_8$+PGA-g-PEG.

In Vitro MH Release in Urine

LbL films were incubated in sterile urine at 37° C. for quantification of MH release. Every 24 h, the release medium was removed and replaced with fresh urine. The amount of MH released at each time point was determined and integrated by Waters 1525 high-performance liquid chromatography (HPLC).

Biofilm Assay

The growth of E. coli, A. baumannii and S. aureus was observed on bare catheters and on anti-adhesion modified catheters coated by $(PEI/PSS)_{10}$+$(PGA-g-PEG/GA)_8$+PGA-g-PEG. 100 μL were transferred into 10 mL TSB medium with additional 100 μL 50% w/v glucose for seeding. Bacteria were seeded onto catheters in 48-well plate, 500 μL per well, and incubated overnight for 24 h at 37° C. The bare and anti-adhesion modified catheters were washed thoroughly with sterile PBS, then XTT assay was used for quantification of bacteria number.

Macrophage Adhesion

RAW 264.7 cells were cultured in Dulbecco's modified Eagle's medium (DMEM), supplemented with 10% fetal bovine serum (FBS), 1% penicillin/streptomycin, in a humidified atmosphere with 5% $CO_2$ at 37° C. To maintain the cells, they were normally passed at a ratio of 1:10 every three days.

Protein Absorption Study

Catheters were put into 48-well plate and immersed by FITC-labeled bovine serum albumin (BSA) at a concentration of 200 mg/L which is a risk level indicating a possible kidney damage, at 37° C. for 24 h. Subsequently, catheters were thoroughly rinsed with PBS for three times before fluorescent imaging. Blank controls were run simultaneously during each experiment. Data for each condition were pooled, and data were analyzed for statistical significance.

Thickness Measurement

The thickness of MH-releasing LbL films deposited on PVC catheters was measured at dry state using an optical profilometer (Zygo). The thickness of the combined MH-releasing, anti-adhesive LbL film deposited on Si wafers was measured using Atomic force microscopy (AFM).

Coating Thickness

The thickness of $(PEI/PSS)_{10}+PEI+(DS/MH/GA/AS/GC)_{20}$ LbL coating on PVC catheter is 1.14±0.19 μm. The thickness of $(PEI/PSS)_{10}+PEI+(DS/MH/GA/AS/GC)_{24}+(PGA-g-PEG/GA)_{8}+PGA-g-PEG$ is 4.38±1.27 μm.

MH-Releasing LbL Multilayer Film Growth and Characterization

Figure 28:
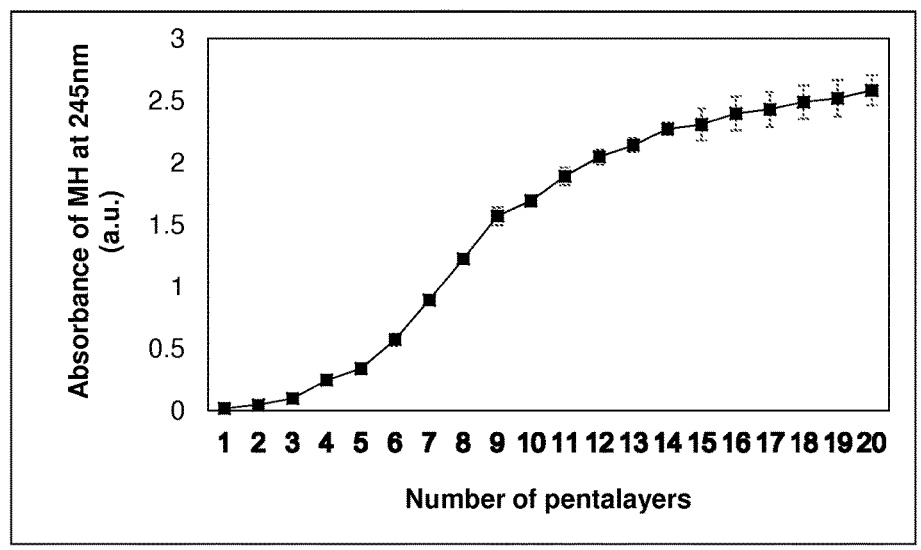
FIG. 28 is a graph illustrating the relationship between UV absorbance of MH as a function of number of pentalayers in the preparation of $(PEI/PSS)_{10}$+PEI+(DS/MH/GA/AS/GC)$_{20}$ LbL film.

FIG. 28 illustrates that the UV absorbance of MH increased with the number of penta-layers of $(PEI/PSS)_{10}+PEI+(DS/MH/GA/AS/GC)_{20}$ LbL film, indicating successful LbL assembly.

MH Release in Urine

Figure 29:
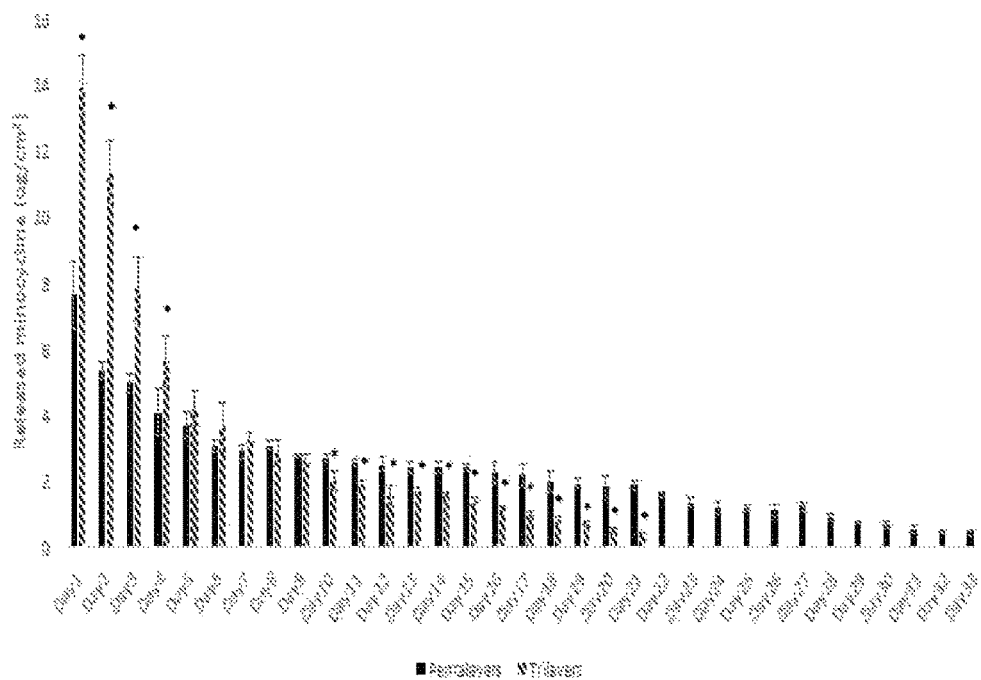
FIG. 29 is a graph illustrating the relationship of MH released in urine as a function of time for $(PEI/PSS)_{10}$+PEI+ $(DS/MH/GA)_{20}$ LbL coating or $(PEI/PSS)_{10}$+PEI+(DS/MH/GA/AS/GC)$_{20}$ on PVC catheter.

FIG. 29 illustrates that MH release in urine from $(PEI/PSS)_{10}+PEI+(DS/MH/GA)_{20}$ LbL coating on PVC catheter lasted for 21 days. After adding AS/GC as protective layer, MH release in urine from $(PEI/PSS)_{10}+PEI+(DS/MH/GA/AS/GC)_{20}$ LbL coating on PVC catheter lasted for 33 days.

Antibiofilm Potency of Released MH

Figure 30:
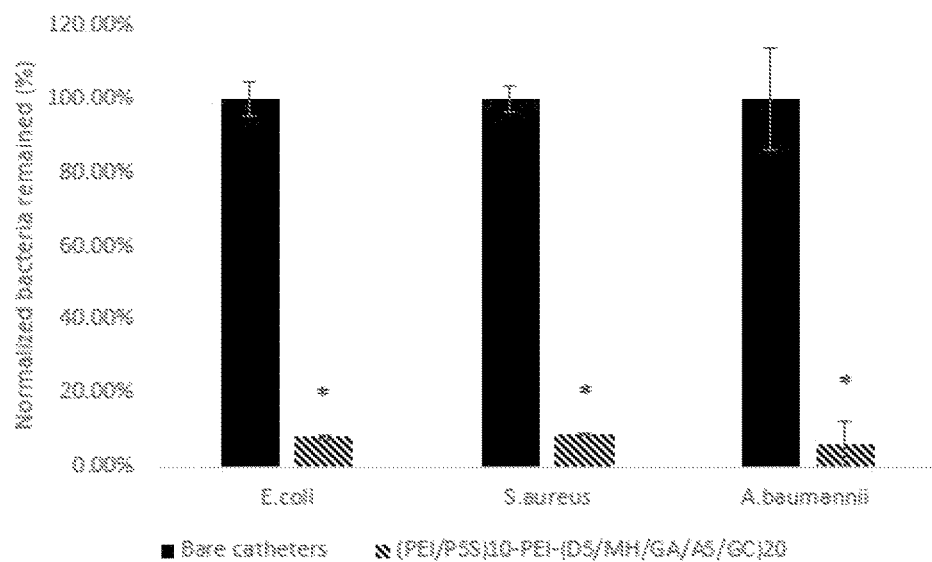
FIG. 30 is a bar graph illustrating the results of XTT assays for $(PEI/PSS)_{10}$+PEI+(DS/MH/GA/AS/GC)$_{20}$.

XTT assay shows that $(PEI/PSS)_{10}+PEI+(DS/MH/GA/AS/GC)_{20}$ significantly inhibited biofilm formation by all three bacteria species (FIG. 30). The percentage of reduction for E. coli, S. aureus and A. baumannii was 91.9±3.7%, 91.2±3.2% and 93.8±6.1%, respectively (FIG. 30).

Protein Adsorption Study on Anti-Adhesive Coating

Figure 31:
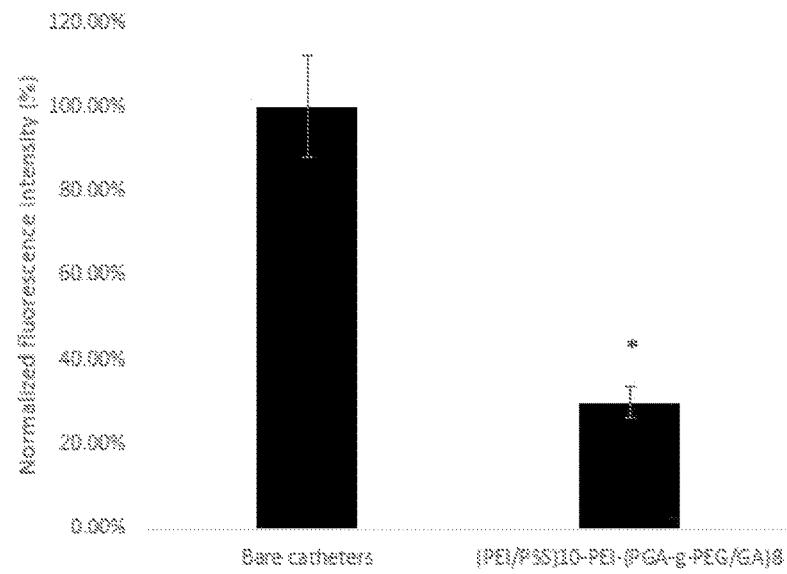
FIG. 31 is a bar graph illustrating the fluorescence intensity of FITC-BSA adsorption on bare and coated catheters.

FIG. 31 illustrates that the fluorescent intensity of FITC-BSA adsorption on the anti-adhesive coating $(PEI/PSS)_{10}+PEI+(PGA-g-PEG/GA)_{8}+PGA-g-PEG$ coated catheters were reduced by 70.1±29.8%. Compared with the bare catheters, coated catheters had significantly less BSA adsorption after 24 h exposure ($P<0.01$).

Bacteria Adhesion Study on Anti-Adhesive Coating

Figure 32:
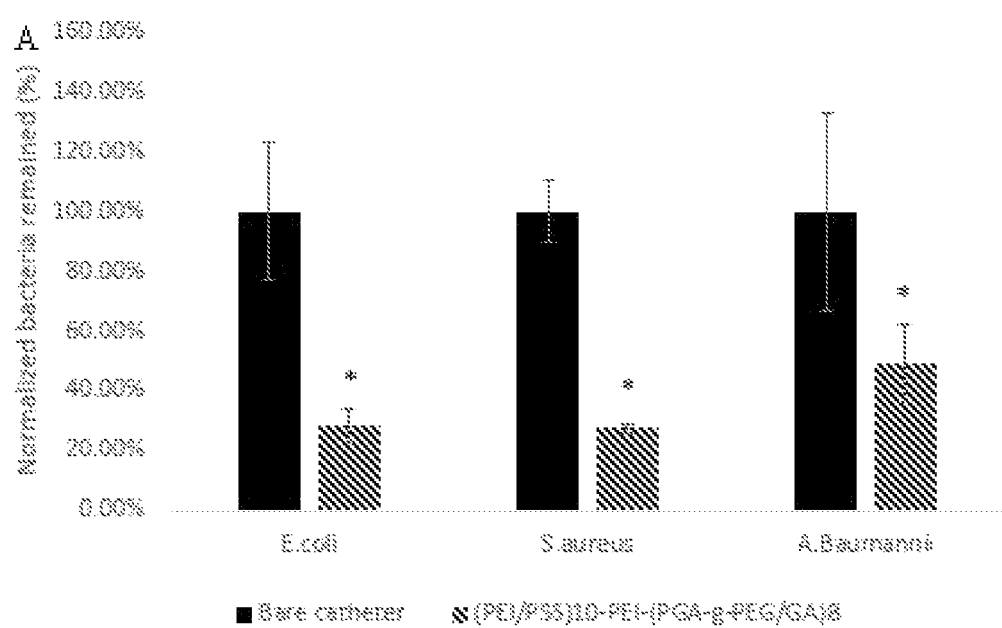
FIG. 32 is a bar graph illustrating bacteria adhesion studies on anti-adhesive coating.

XTT assay shows that the number surviving E. coli, a major pathogen causing catheter associated urinary tract infection, on $(PEI/PSS)_{10}+PEI+(PGA-g-PEG/GA)_{8}+PGA-g-PEG$ coated catheters was reduced by 71.5±5.3% compared to bare catheters. The numbers of A. baumannii and S. aureus on coated catheters were reduced by 50.5±33.0% and 72.5±10.4%, respectively (FIG. 32).

Macrophage Adhesion Study on Anti-Adhesive Coating

FIG. 33A illustrates DAPI fluorescent staining to quantify macrophage adhesion on bare catheters and $(PEI/PSS)_{10}+PEI+(PGA-g-PEG/GA)+PGA-g-PEG$ coated catheters. *, $P<0.05$ compared to $(PEI/PSS)_{10}+PEI+(PGA-g-PEG/GA)_{6}+PGA-g-PEG$. Data illustrated are average±SD (n=4). FIGS. 33B-33H illustrate remaining mouse macrophage adhesion on bare catheters, $(PEI/PSS)_{10}-PEI-(PGA-g-PEG/GA)_{1}+PGA-g-PEG$, $(PEI/PSS)_{10}-PEI-(PGA-g-PEG/GA)_{2}+PGA-g-PEG$, $(PEI/PSS)_{10}-PEI-(PGA-g-PEG/GA)_{4}+PGA-g-PEG$, $(PEI/PSS)_{10}-PEI-(PGA-g-PEG/GA)_{6}+PGA-g-PEG$, $(PEI/PSS)_{10}-PEI-(PGA-g-PEG/GA)_{8}+PGA-g-PEG$, $(PEI/PSS)_{10}-PEI-(PGA-g-PEG/GA)_{10}+PGA-g-PEG$ after 24 h, 37° C. culture. Collectively, FIG. 33 illustrates continuous reduction of macrophage adhesion when increasing the number of (PGA-g-PEG/GA) bilayers. With 1, 2, 4, 6, and 8 anti-adhesive bilayers, the number of macrophages was 79.1±8.1%, 76.7±7.6%, 36.8±8.5%, 27.2±8.5% and 9.2±4.5% of uncoated control. Further increasing the number of bilayers to 10 did not significantly charged the number of adhered macrophages. Thus, in certain embodiments, eight bilayers of PGA-g-PEG/GA is sufficient to effectively inhibit macrophage adhesion.

Antibiofilm Potency of Combined MH-Releasing and Anti-Adhesive LbL Film

Figure 34:
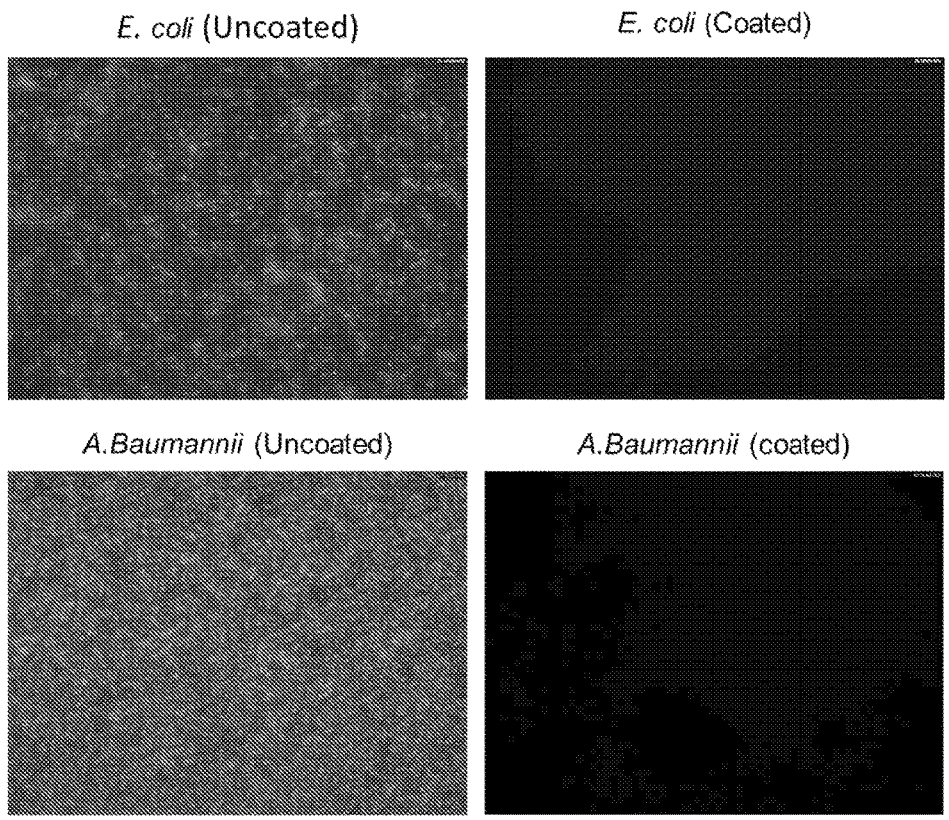
FIG. 34 is a series of images illustrating antibiofilm potency of combined MH-releasing and anti-adhesive LbL film.

FIG. 34 illustrates that while both E. coli and A. baumannii formed biofilm on uncoated tissue culture plate after 24 hr of culture, no bacteria was found in $(PEI/PSS)_{10}+PEI+(DS/MH/GA/AS/GC)_{24}+(PGA-PEG/GA)_{8}+PGA-g-PEG$ coated wells.

Example 7: Injectable Hydrogel Comprised of Therapeutic Agent/Polyelectrolyte/Metal Ion Complexes Releasing Doxorubicin for Cancer Therapy Standard clinical care for early stage breast cancer includes lumpectomy followed by localized radiotherapy to achieve long-term remission. However, radiation therapy can cause serious side effects including buildup of lymph fluid that limits operative healing, and long-term health complications. Alternatively, chemotherapeutic drugs can be administered following lumpectomy. However, the chemotherapeutic drugs can cause a loss of normal, healthy tissue in addition to tumor tissue, leading to undesirable side effects.

As demonstrated herein, low dose and prolonged treatment with anticancer drug doxorubicin (DOX) can effectively kill 100% MDA-MB-231 breast cancer cells while exhibited no significant cytotoxicity to NIH 3T3 fibroblasts. A novel drug delivery system for controlled and sustained release of low dose of DOX was developed based on self-assembled DOX-dextran sulfate (DS) complexes. As demonstrated herein, adding divalent metal ions in the complex can improve the entrapment efficiency of DOX and prolong DOX release. Biocompatible, biodegradable, and injectable hydrogels agarose and agarose/methylcellulose (MC) were used to encapsulate the DS-DOX complex. The hydrogels may be injected into the cavity after lumpectomy for sustained local delivery of low-dose DOX. Cell viability experiments confirmed that this drug delivery system completely eliminated MDA-MB-231 cells while maintained the viability of NIH 3T3 fibroblasts at the end of treatment. Thus, this novel drug delivery system represents a promising approach for localized chemotherapy to improve locoregional control of breast cancer.

This study investigated new self-assembled DS-DOX complexes with or without metal ions for controlled and sustained release of anticancer drug DOX. This study used high molecular weight DS (MW 500,000 Da), which prolonged DOX release from 28 to 33 days and decreased the initial burst.

Complexes collected by centrifugation were found to be difficult to separate and resuspend uniformly in hydrogel. Thus, the complex was prepared in situ in the hydrogel solution. To obtain sufficient amount complex in the hydrogel, DOX concentration was increased to 0.5 mg/mL during complex formation to obtain concentrated complexes. The DS/DOX ratio of 1 was selected because it demonstrated the highest entrapment efficiency. Further, adding metal ions including $Ca^{2+}$ and $Mg^{2+}$ during complex formation significantly improved the entrapment efficiency of DOX from around 65% to almost 100%. Without wishing to be limited by any theory, this may occur because both DOX and DS have high binding affinity for these divalent metal ions. The metal ion binding-mediated interaction also enabled stable long-term release for more than 78 days.

This is the first report in which divalent metal ion-assisted coacervation of DOX and DS was used to improve the DOX entrapment and prolong DOX release. Furthermore, DOX release from the complexes was found to be pH-sensitive. The extracellular pH in cancerous tissue is known to be substantially and consistently lower than that in normal tissue. Thus, the drug delivery system of the invention can potentially enhance DOX release in the cancerous tissue but reduce DOX release in normal tissue, enabling tissue-specific "smart" drug release. DOX release from the complex was also tunable by varying DOX loading, metal ion concentration, and molecular weight of DS.

SeaPlaque agarose hydrogel was used to encapsulate DS-DOX complex. The composition of the invention can be injected into the cavity where the tumor tissue is surgically removed. However, agarose hydrogel may lack sufficient fluidity to completely fill the cavity seamlessly. To improve the filing and conforming capability of the hydrogel, an improved hydrogel blend Seaplaque/MC was fabricated and tested in this study. In fact, both SeaPrep and SeaPlague hydrogels were evaluated, and Seaplaque/MC hydrogel was found to solidify faster at body temperature and demonstrate higher shear modulus, which is actually close to that of breast tissue.

In certain embodiments, the composition of the invention can be injected as a liquid then solidify in situ at body temperature. This novel blended hydrogel material could be injected into the body, filling and conforming to the body cavity, and then solidify in situ, gradually releasing anticancer drug. This study also demonstrated that low dose and prolonged DOX treatment can completely eliminate cancer cells while maintaining the viability of normal cells using MDA-MB-231 cell line and NIH 3T3 cell line as the model cells. Moreover, when hydrogel loaded with DS-DOX complex was incubated with cancer cells, sustained release of low dose DOX successfully killed all the cancer cells in 7-8 days while did not elicit significant cytotoxicity on NIH 3T3 fibroblasts. This result proved that this novel drug delivery system can be used to release DOX with appropriate dose and duration to kill all the cancer cells while exhibiting limited toxicity to normal tissue.

In certain embodiments, releasing DOX for 2 days before treatment eliminates the relatively high initial burst, which may be disadvantageous for clinical application. In other embodiments, the initial burst of therapeutic agent is reduced. Without wishing to be limited by any theory, the complex size may play a role in controlling initial burst. The surface area to volume ratio of the complexes decreases with the increase of complexes size, which may reduce the rate of DOX release from the complex. Further, a protective coating on the complex may be used to slow down the release rate in first few days.

As demonstrated herein, an injectable drug delivery system based on injectable hydrogel and DS-DOX complex was developed. This drug delivery system can be optimized to release appropriate dose and duration of DOX to provide effective local chemotherapy after lumpectomy, while minimizing cytotoxicity to normal breast tissue.

Materials

Dextran sulfate [Low Molecular Weight Dextran Sulfate (LMWDS), MW of 6,500-10,000, and High Molecular Weight Dextran Sulfate (HMWDS), MW>500,000], doxorubicin HCl was purchased from Sigma Chemical Co. Seaplaque® Agarose and Seaprep® Agarose were purchased from Lonza Group Ltd. Methyl cellulose (Methocel A15 Premium LV) was obtained from DOW chemical Co. $CaCl_2$ and $MgCl_2$ was purchased from Fisher Scientific Inc. Deionized water (DI) was used in the study.

Preparation of DS-DOX Complexes

For non-ion complexes without ion involvement in its self-assemble process, DS (1 mg/mL) was dissolved in deionized water. For complexes involving metal ions in the self-assemble process, DS (1 mg/mL) was dissolved in $CaCl_2$ or $MgCl_2$ solution. DOX (1 mg/mL) was dissolved in DI water. Equal volumes (150 μL) of DS solution and DOX solution were mixed with 10 s vortexing to induce complex formation. In certain embodiments, the ratio of DS and DOX is about 1:1 (w/w). In other embodiments, the ratio of DS to DOX is about 1:1 (monosaccharide subunit—drug).

DOX Entrapment Efficiency and Loading Efficiency

Entrapment efficiency of DS-DOX complexes was analyzed by centrifugation of complex suspension at 15,000 rpm for 20 min. To make sure that free DOX did not precipitate in centrifugation, free DOX solution was used as control. The concentration of remaining DOX in supernatant was calculated from the fluorescent measurement spectroscopically at excitation wavelength of 470 nm and emission wavelength of 550 nm. The concentration of remaining DS in supernatant was determined through a spectrophotometric method that measures the absorbance of reaction solution at wavelength of 584 nm after 10 min reaction between remaining DS and equal volume of 1 mM toluidine blue.

Dynamic Light Scattering (DLS)

The hydrodynamic mean diameter of DS-DOX complexes was measured through dynamic light scattering (DLS) using a Zetasizer (Malvern Instruments, MA, USA).

In Vitro Release of DOX from DS-DOX Complexes

In vitro drug release profile of DS-DOX complex was investigated. Complex suspension was placed into 1.5 mL centrifuge tube with 450 mL Hanks Balanced Salt Solution (HBSS) as release medium at 37° C. The complexes were then incubated in a 37° C. incubator. Released medium was taken out and replaced by same volume of fresh HBSS every day. The amount of DOX in the release medium was determined by fluorescent reading at an excitation wavelength of 470 nm and emission wavelength of 550 nm through Tecan Infinite M200 plate reader using 96-well black plate.

Fabrication of Hydrogels Loaded with Complex

For agarose hydrogel, agarose powder was dissolved in HBSS at 85° C. at different concentrations depending on complex loading for DOX loading of 50 μg/mL, 100 μg/mL, 150 μg/mL, the agarose concentration was 1.67%, 1.88%, 2.14% respectively. The weight of whole system was measured before and after dissolution, and water was added to replenish the loss of evaporation. Agarose solution was filtered for sterilization by 450 nm filter for sterile agarose hydrogel preparation. Agarose solution was then cooled down to 37° C. to allow DOX keeping its bioactivity. DS-DOX complexes were made by mixing equal volume of 1 mg/mL DS and DOX solution followed by vortexing for 10 s. The final concentration of DS and DOX in the mixture was 0.5 mg/mL. Then the mixture solution (for DOX loading of 50 μg/mL, 100 μg/mL, 150 μg/mL, the ratio of complexes mixture solution to agarose solution was 1:9, 1:4, 3:7, respectively) was well mixed with agarose solution. The final concentration agarose hydrogel was fixed at 1.5% w/v. The sample was put into 4° C. refrigerator to allow agarose hydrogel solidifying.

For agarose/MC hydrogel, MC powder was added in agarose solution while stirring in 85° C. At temperature above 80° C., the MC is insoluble and can easily be dispersed throughout the liquid. After well distributed into a white well-dispersed suspension, the mixture was quickly cooled down in ice water bath for 10 min with rapid stirring to form an agarose/MC solution. Then agarose/MC solution was centrifuged at 3,000 rpm for 3 min to remove bubble. 10 min Ultraviolet radiation was given for sterile agarose/MC solution. Then DS-DOX complex solution was well mixed with the agarose/MC solution. The final concentration of agarose was 1.5% w/v and the final concentration of MC was 7% w/v. The hydrogel solidified at 37° C.

Mechanical Properties and Gelation Time of Hydrogel

The rheological measurements were done with a Weissenberg Rheogoniometer (Metravib. Instruments. Inc.) using a cone and plane geometry (radius 2.5 cm) in oscillatory shear. A cover was used in order to avoid evaporation in 30 min measurement. Temperature was kept in room temperature 25° C. when the sample was loaded. The complex modulus G and storage modulus G' were measured every 20 s for 40 min After that loss modulus G" was calculated and gelation time was determined at time point G'=G".

Cell Culture

The human breast carcinoma cell line MDA-MB-231 was cultured in Sodium Pyruvate (SP) free Dulbecco's Modification of Eagle's Medium (DMEM) containing 10% fetal bovine serum (FBS), 1% penicillin/streptomycin (P/S), in a 5% $CO_2$, humidified incubator. The NIH 3T3 cell line was cultured in DMEM with SP containing 10% FBS, 1% P/S, in a 95% air, 5% $CO_2$, humidified incubator.

For hydrogel treatment, cells were seeded at $2\times10^4$ cells per well in 24-well tissue culture plates. For fresh DOX treatment and released DOX treatment, cells were seeded at $3\times10^3$ cells per well in 96 well tissue culture plates. One day after seeding, the medium was removed, then fresh medium with various concentrations of doxorubicin hydrochloride was added. In parallel, fresh medium without gel or free therapeutic agent was served for control group. The medium was changed every 24 hr.

Cytotoxicity of Released DOX

100 μL hydrogel was released in 450 μL HBSS. The released HBSS medium was collected every day. The concentration of released doxorubicin was calculated from its fluorescent reading. Released HBSS medium was mixed with DMEM medium (with 20% FBS and 2% P/S) in ratio of 1:1 for MDA-MB-231 cell treatment. Cells cultured in HBSS/DMEM (1:1) medium without any DOX were treated as negative control. MDA-MB-231 cell line was seeded in 96-well plate in density of 3,000 cells per well and cultured in HBSS/DMEM medium overnight. Then medium was removed and HBSS/DMEM medium with DOX was given and incubated for 3 days. In each control group, fresh DOX in HBSS/DMEM (1:1) medium with same concentration was used to treat cell.

Cytotoxicity of Complex-Loaded Gel

150 μg/mL DOX was loaded as non-ion DS-DOX complex in agarose hydrogel. Gel was washed in HBSS for 3 days. Cell (MDA-MB-231 cell line and NIH 3T3 cell line) was seeded in 24-well plates in density of $2\times10^4$ cells per well and cultured overnight. One day after seeding, the medium was removed and various volumes of gel samples were injected to the center of well quickly. Then fresh medium was given and refreshed every 24 h. Images of cells were taken every day under phase contrast microscope.

Formation of DS-DOX Complexes

DS-DOX complexes self-assembled without any visible aggregates upon mixing of DOX solution and DS solution in the absence of metal ions (non-ion DS-DOX complex). While in the presence of $Ca^{2+}$ or $Mg^{2+}$ ions, DS-metal ion-DOX complex quickly formed large red-colored aggregates visible by eye, denoted as $Ca^{2+}$-DS-DOX complex or $Mg^{2+}$-DS-DOX complex. In all entrapment efficiency studies, the concentration of DOX was kept at 0.05 μg/mL, HMWDS was used, and mass ratio of DOX/DS was adjusted by varying DS concentration.

Figure 35:
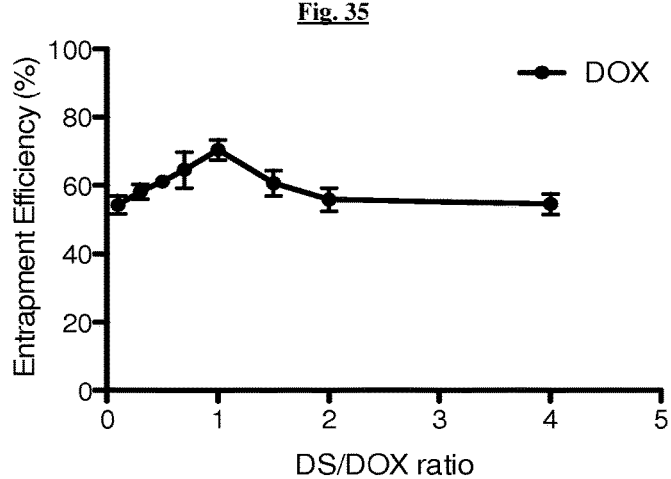
FIG. 35 is a graph illustrating the relationship between entrapment efficiency and DS/DOX ratio.

FIG. 35 illustrates the finding that the entrapment efficiency of DOX in non-ion DS-DOX complex increased with the DOX/DS ratio up to 1 (70.4%), after which the entrapment efficient started to decrease. Based on this result, DS/DOX ratio of 1 was used for the formulation of DS-DOX complex in the subsequent study.

Entrapment Efficiency of DS-DOX Complexes with and without Metal Ions

Figure 36:
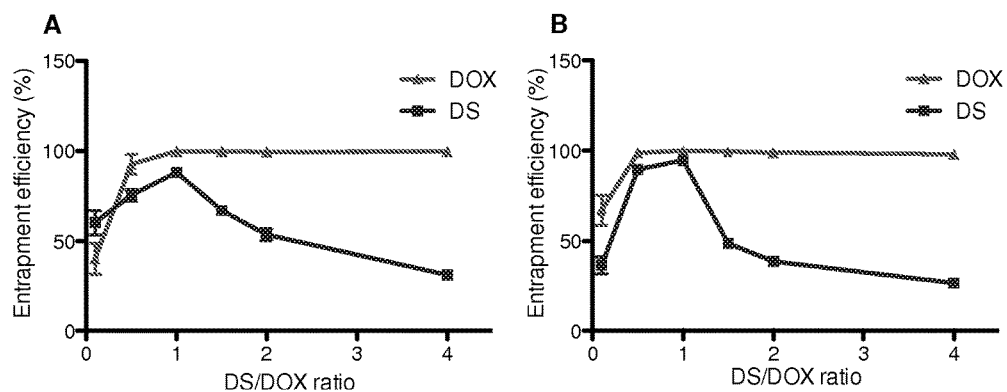
FIG. 36, comprising

The effect of DS/DOX ratio on DOX entrapment efficiency was studied in DS-metal ion-DOX complexes. In this study the concentrations of $Ca^{2+}$ and $Mg^{2+}$ ions were kept at 2.7 mM. The strong divalent metal ion-mediated interactions enabled the complexes to load DOX with very high entrapment efficiency. As illustrated in FIG. 36A, the entrapment efficiency of DOX in $Ca^{2+}$-based complex increased rapidly to 92.6% at a DS/DOX ratio of 0.5, and reached a plateau of 99.7% at a ratio of 1. FIG. 36B illustrating the finding that the entrapment efficiency of DOX versus DS/DOX ratio in $Mg^{2+}$-based complex followed the same pattern and increased rapidly to 98.7% at DS/DOX ratio of 0.5, after which it reached plateau of 100.0% at a ratio of 1. For both $Ca^{2+}$ and $Mg^{2+}$-based complexes the entrapment efficiencies of DS reached maximum (75.4% and 94.1%) when the ratio was 1.

Figure 37:
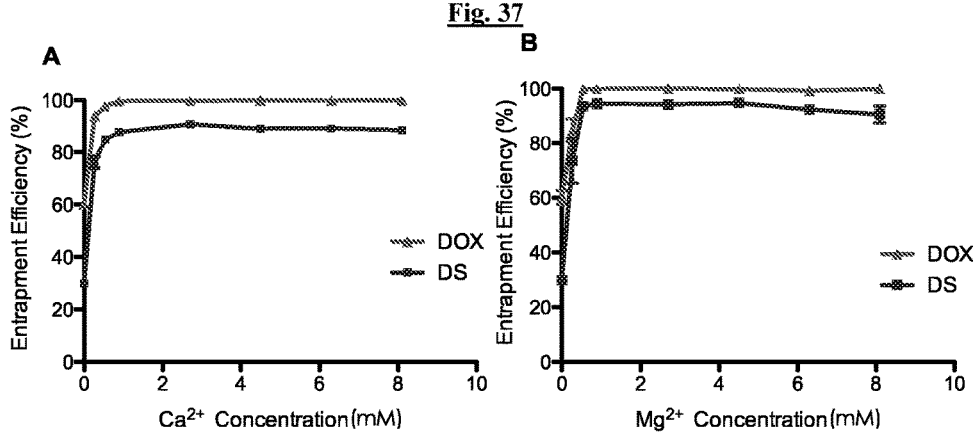
FIG. 37, comprising

The entrapment efficiency of DOX and DS was also affected by metal ion concentration. As illustrated in FIG. 37A, for $Ca^{2+}$-based complex the entrapment efficiencies of DOX and DS increased rapidly with $Ca^{2+}$ concentration till 0.54 mM (97.7% and 84.8%), after which further increasing $Ca^{2+}$ concentration only slightly increased the entrapment efficiencies of DOX and DS to 100.0% and 88.8% at $Ca^{2+}$ concentration of 8.1 mM, respectively. Figure illustrates the finding that for $Mg^{2+}$-based complex the entrapment efficiencies of DOX and DS versus $Mg^{2+}$ concentration showed similar pattern, except that they reached plateau (100% and 94.6%) at $Mg^{2+}$ concentration of 0.54 mM. In addition, when the entrapment efficiencies of DOX and DS versus metal ion concentration reached plateau, the loading efficiency of DOX reached plateau as well. Formed with 0.54 mM of divalent metal ion, $Ca^{2+}$-based complex and $Mg^{2+}$-based complex had similar loading efficiency of DOX (52.5% and 53.5%).

DLS Measurement

Figure 38:
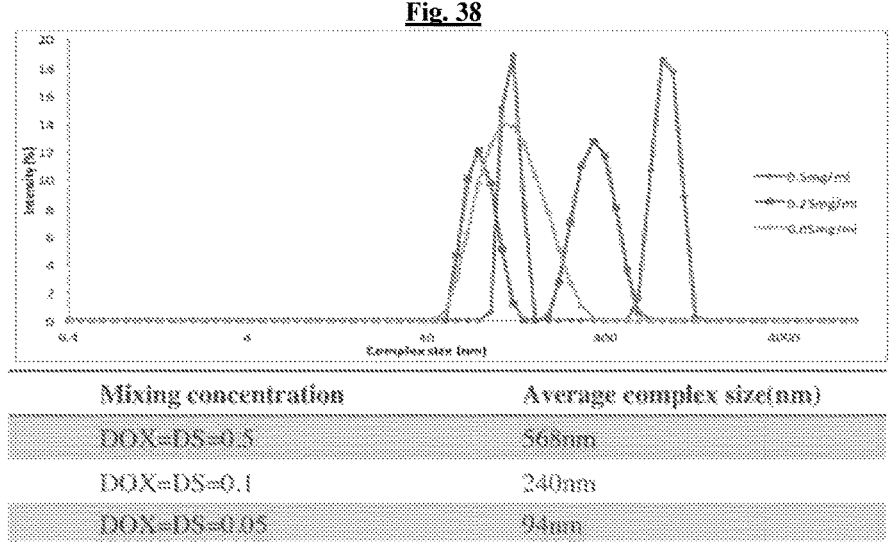
FIG. 38 is a graph illustrating DLS measurements.

The hydrodynamic mean diameter of non-ion DS-DOX complex was measured through DLS. HMWDS was used in this study. FIG. 38 illustrates the finding that the hydrodynamic diameter of the complex decreased with the concentration of DS and DOX during complex formation. This result suggests that the complex size can be controlled by adjusting DOX and DS concentrations. In certain embodiments, DOX release from larger complex is slower. Thus, the release rate of DOX can potentially be controlled by changing DOX and DS concentrations. In the presence of $Ca^{2+}$ or $Mg^{2+}$ ions, DS-metal ion-DOX complex quickly formed large aggregates that cannot be measured by DLS.

Effect of Metal Ion on DOX Release

Figure 39:
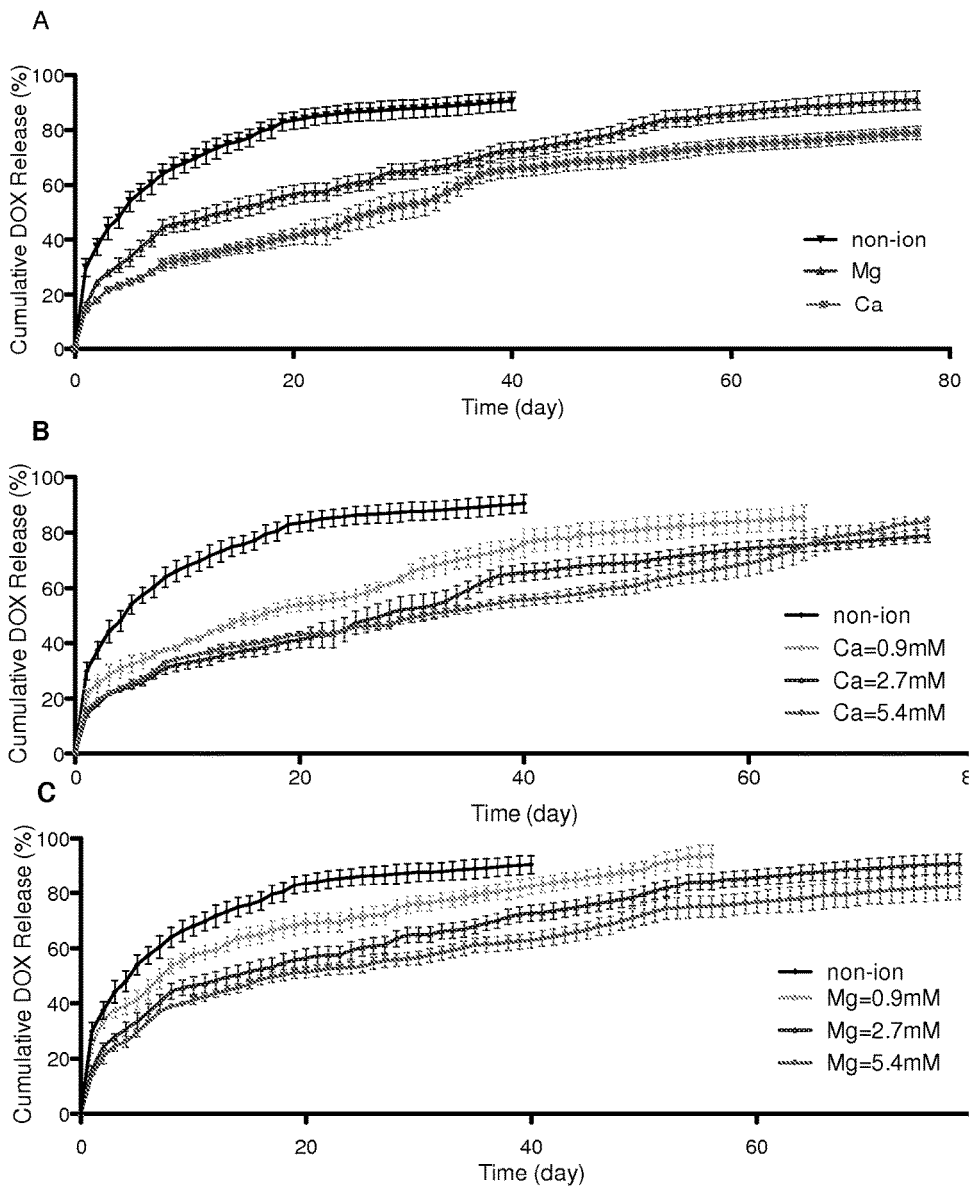
FIG. 39, comprising

HMWDS was used in this study. The initial total loading of DOX was 15 μg. Divalent metal ions increased the entrapment efficiency of DOX, suggesting that metal ions enhance the interaction between DS and DOX in complex. Consistent with this result, FIG. 39A illustrates that DOX release from $Ca^{2+}$ or $Mg^{2+}$-based complex (metal ion concentration of 2.7 mM) was prolonged from 40 to over 80 days compare with non-ion complex.

Various concentrations of metal ions were used for complex formation to investigate the effect of metal ion concentration on DOX release. The entrapment efficiency of DOX was 99% at a $Ca^{2+}$ concentration of 0.9 mM (FIG. 39A), suggesting a stronger binding for DOX. Likewise, release was prolonged from 40 to 65 days (FIG. 39B) when added 0.9 mM $Ca^{2+}$ in complex formation. Further, increasing $Ca^{2+}$ concentration to 2.7 mM and 5.4 mM prolonged the duration of release to more than 80 days (FIG. 39B). For $Mg^{2+}$-based complex, the effect of $Mg^{2+}$ concentration on DOX release followed same pattern: DOX release was prolonged from 40 to 58 days when 0.9 mM $Mg^{2+}$ was added during complex formation. Further, increasing $Mg^{2+}$ concentration to 2.7 mM and 5.4 mM also prolonged the release to more than 80 days (FIG. 39C). For all the conditions, the release of DOX followed near zero-order release kinetics after the initial burst. Higher concentration of metal ions decreased initial burst and prolonged the release.

Release of DOX from Complex Loaded Hydrogel

Figure 40:
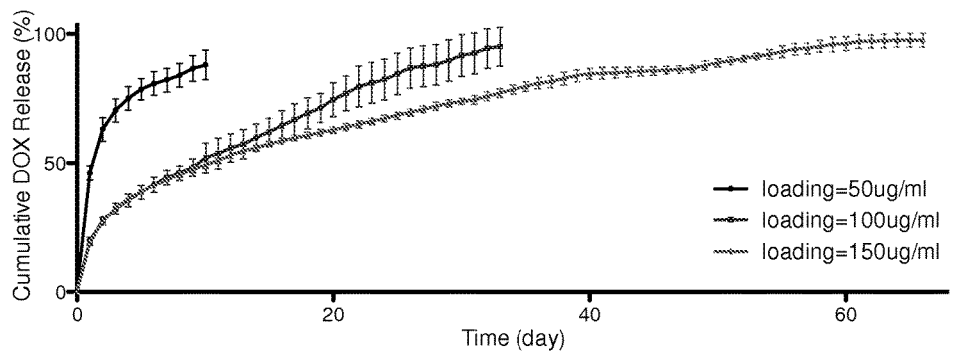
FIG. 40 is a graph illustrating the effect of loading on cumulative DOX release.

Effect of DOX Loading:

Agarose hydrogel was loaded with different amount of $Ca^{2+}$ based complexes. The final DOX loading was 50, 100, and 150 μg/mL, respectively, corresponding to 10, 33, and 66 days of drug release (FIG. 40). This result demonstrates increasing DOX loading in the hydrogel can prolong DOX release. The initial bust release was greatly reduced at higher loadings.

Effect of pH:

Reduced extracellular pH (6.6 to 7.2) is commonly found in tumor tissue (Gerweck & Seetharaman, 1996, Cancer Research 56(6):1194-1198). To simulate pathological and physiological conditions, HBSS with pH of 6.5 and 7.4 were used as release media. Non-ion complexes made from HMWDS and DOX were used in this study.

Figure 41:
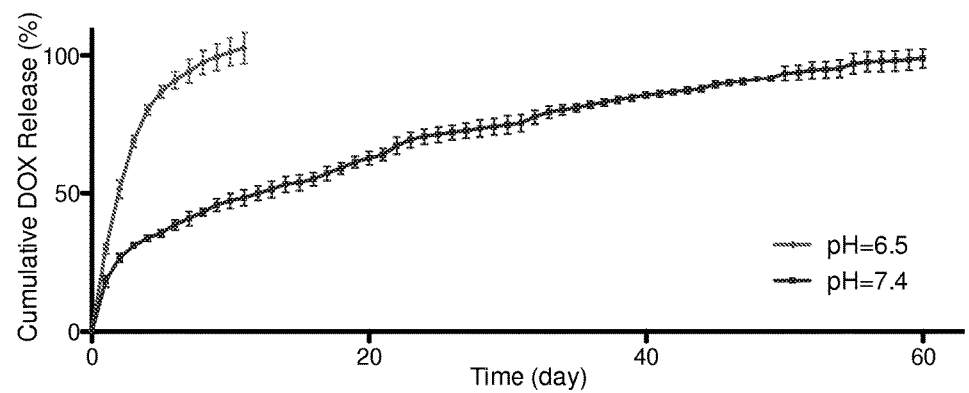
FIG. 41 is a graph illustrating the effect of pH on cumulative DOX release.

As illustrated in FIG. 41, 100% of DOX was released from non-ion DS-DOX complexes in 11 days at pH 6.5, versus 60 days at pH 7.4. This result suggests that the DS-DOX complex can be used as a "smart" drug delivery system to actively deliver MH in response to the tumor-induced tissue acidosis. In certain embodiments, release rate gradually decreased with increased pH. Since pH 6.5 represents an extreme condition, DOX release from the complex may take much longer in most tumor conditions.

Figure 42:
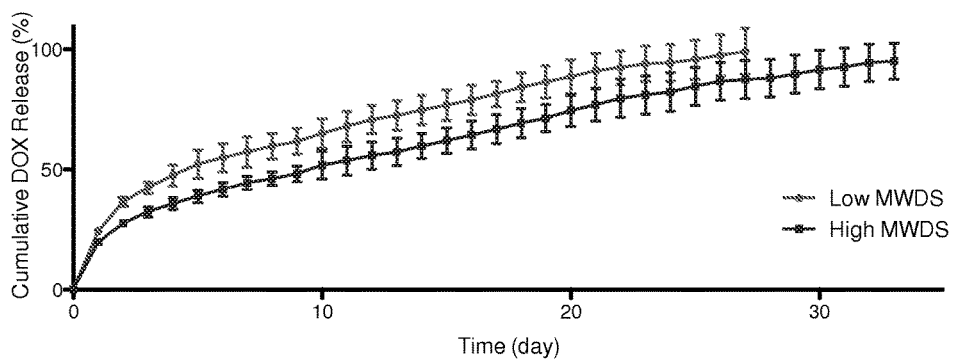
FIG. 42 is a graph illustrating the effect of DS molecular weight on cumulative DOX release.

Effect of Molecular Weight of DS:

The DS-DOX complexes were fabricated using LMWDS (MW of 6,500-10,000) and HMWDS (MW>50,000) respectively to evaluate the effect of DS molecular weight on DOX release. The DOX loading in the hydrogel was 10 μg. No metal ion was used in this study. FIG. 42 illustrates the HMWDS mildly prolonged DOX release from 28 to 33 days and decreased the initial burst.

Formation of Agarose/Methylcellulose Hydrogel

Gelation Time:

The agarose/MC hydrogel were viscous liquids at 4° C., less viscous liquids at room temperature, and solid species at 37° C. Agarose hydrogel could hold its 3D morphology immediately after injection because it was already solidified in advance. On the other hand, agarose/MC hydrogel were more fluid after injection, which allowed for the agarose/MC hydrogel to better conform to the irregular geometry of the injury cavity.

Figure 43:
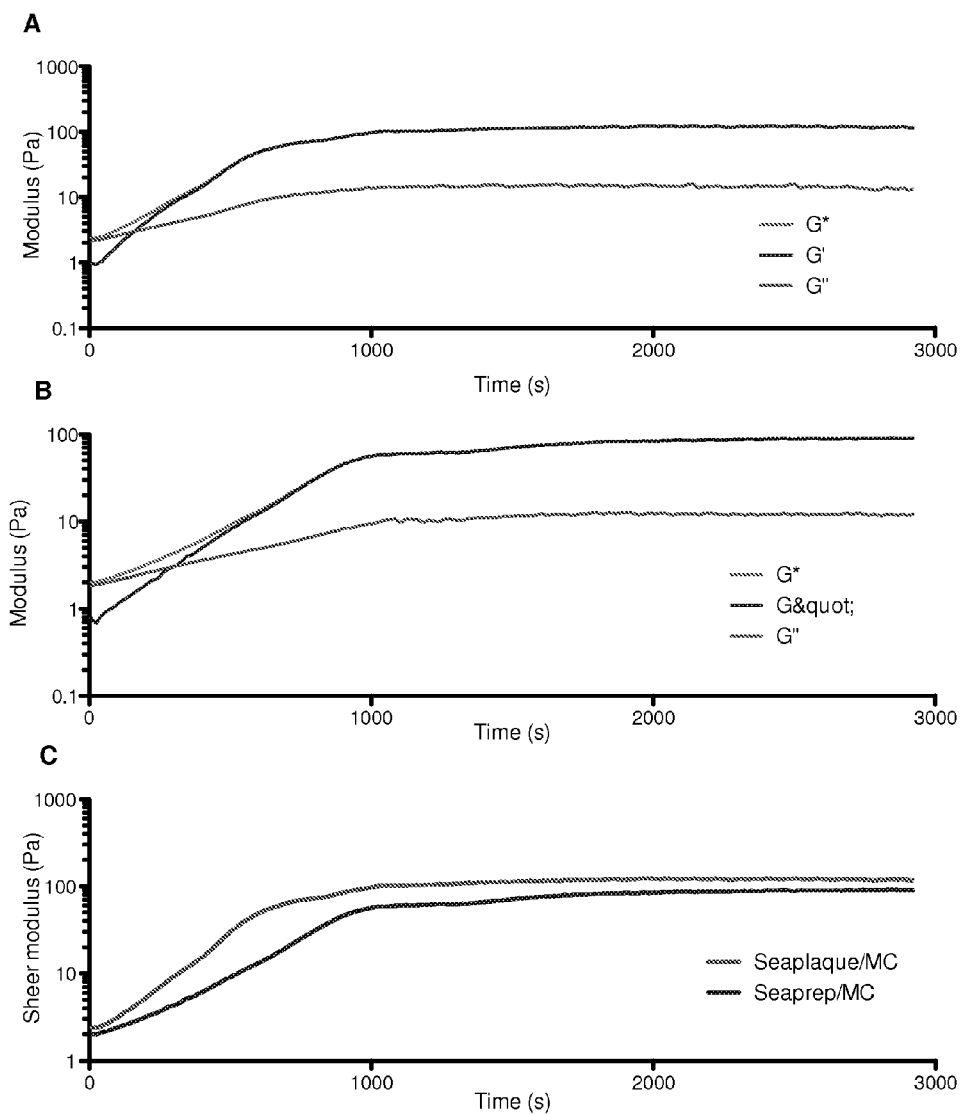
FIG. 43, comprising

Rheological data (FIG. 43) shows that the elastic modulus of the agarose/MC hydrogel rapidly increased at 37° C., and then slowly over the course of 15 min Both of the agarose/MC hydrogels had similar increasing modulus curves. As illustrated in the FIG. 43A, at 192 s, the storage modulus was higher than loss modulus, indicating solidification of the Seaplaque/MC hydrogel, while for Seaprep/MC hydrogel (FIG. 43B) the gelation time was 325 s. Based on all above, the gelation time of Seaplaque/MC hydrogel was around 3 min, less than that of Seaprep/MC hydrogel, 5.5 min, showing of Seaplaque/MC hydrogel solidify faster.

FIG. 43C illustrates the Seaprep/MC hydrogel had smaller shear modulus, which indicated it is softer than Seaplaque/MC hydrogel. The shear modulus of breast tissue is around 150 Pa (Levental, et al., 2007, Soft Matter 3(3): 299-306), which is higher than shear modulus of both Seaplaque/MC and Seaprep/MC hydrogel. Seaplaque/MC hydrogel had higher shear modulus more close to that of breast tissue. In certain embodiments, through modulating the agarose/MC ratio or adding other chemical compound might increase the shear modulus to desired range.

DOX Release from Formulations of Agarose/MC Hydrogel

Figure 44:
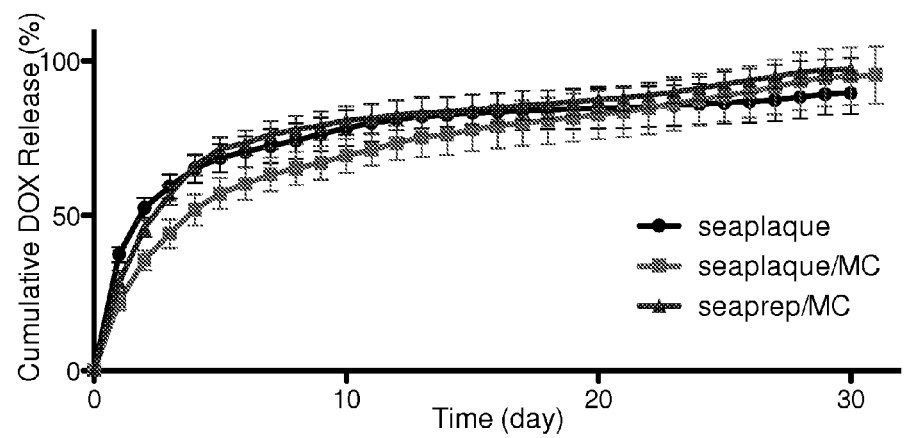
FIG. 44 is a graph illustrating the time-dependent cumulative DOX release for various formulations of agarose/MC hydrogel.

Four hydrogel formulations were used in this study: 1.5% w/v Seaplaque® agarose (Seaplaque), 1.5% w/v Seaplaque® agarose+7.6% w/v MC (Seaplaque/MC), 1.5% w/v Seaprep® agarose (Seaprep), 1.5% w/v Seaprep® agarose+7.6% w/v MC (Seaprep/MC). The hydrogels were loaded with non-ion DOX-HMWDS complex. DOX loading in the hydrogel was 50 μg/mL. DOX release from Seaprep® agarose hydrogel was not illustrated because the material broke into pieces in 4 days due to low stiffness. DOX release from Seaplaque and Seaprep/MC showed similar pattern and time-span of 30 days (FIG. 44), while that from Seaplaque/MC showed decreased initial burst at first 6 days, and a faster release rate after that. DOX release lasted for 31 days in Seaplaque/MC hydrogel.

Hydrogel stability was studied to in vitro. 30% Seaprep/MC and 10% Seaplaque/MC degraded after 30 days of release, while Seaplaque hydrogel did not show volume reduction.

Bioactivity of Released DOX

DOX hydrochloride is very stable in the solid state, and may be stored for years at room temperature without any loss in potency or indications of degradation. However, the stability of DOX in aqueous solution can be affected by many factors, such as pH, buffer concentrations, temperature, and light. Doxorubicin stock solution is stable at 4 degree for 1 month. However, based on the instruction booklets of Adriamycin® (Doxorubicin HCl) injection, DOX solution is stable for only 7 days at room temperature. It is reported that 30%-40% of DOX was degraded in cell culture medium at 37° C. in only 4 days (Janssen et al., 1985, Int'l J. Pharm. 23(1):1-11).

Figure 45:
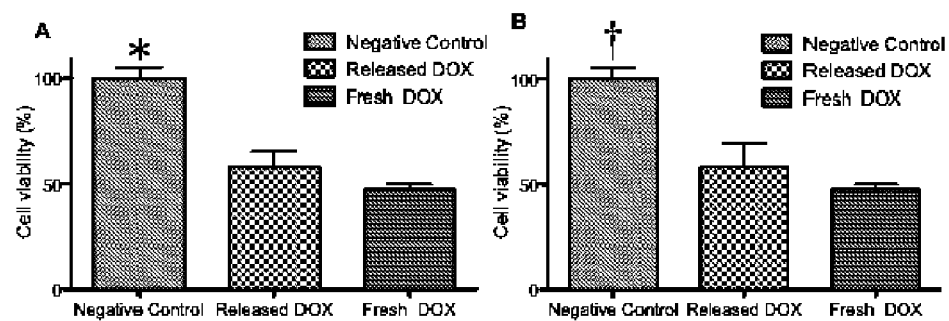
FIG. 45, comprising

Since the present drug delivery system is designed for long term local treatment in human body, it must maintain the stability of DOX at 37° C. during the course of treatment. In this study, hydrogels loaded with 150 μg/mL high MW DS-DOX complex with and without $Ca^{2+}$ were incubated at 37° C. in HBSS. The anticancer activity of released DOX was examined using the human breast cancer cell line MDA-MB-231. DOX release from non-ion complex $Ca^{2+}$- based complex lasted over 49 and 78 days, respectively. The release during a 24 h period on day 32 from non-ion complex and day 39 from $Ca^{2+}$-based complex was 0.58 µg/mL, which was diluted to 0.3 µg/mL and added to MDA-MB-231 cell cultures. The cell viability in these cultures was compared to that in the culture treated with 0.3 µg/mL fresh DOX. FIG. 45 illustrates the finding that DOX released from either complex significantly reduced cell viability to the same degree as fresh DOX, indicating that the present drug delivery system can maintain long term stability of DOX in the aqueous environment of human body at 37° C.

Anticancer Activity of Complex-Loaded Hydrogel

Figure 46:
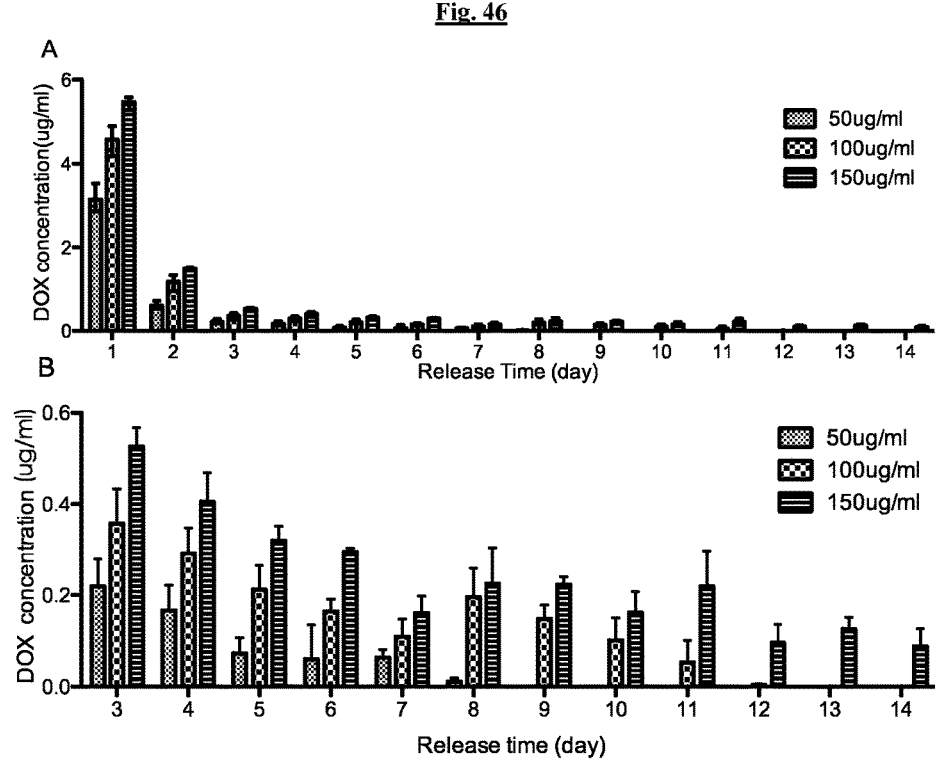
FIG. 46, comprising

This study was designed to mimic in vivo treatment with hydrogel loaded with DOX complex as a postoperative local chemotherapy. Based on the results from the dose-dependent and time-dependent study, a DOX release profile within a concentration range of 0.1-0.4 µg/mL for 5-9 days can effectively kill cancer cells with minimal fibroblast cytotoxicity. Therefore, non-ion complexes, which have the shortest release profile, were selected. Agarose hydrogel was loaded with 50, 100, and 150 µg/mL non-ion DOX-HMWDS complex. 50 µl hydrogel were injected into blank wells of a 24 well plate and incubated in 450 µl HBSS. FIG. 46A illustrates that for all three loading the concentrations of DOX released in the first two days were above the optimum dose range of 0.1-0.4 µg/mL. Hence, for the anticancer assay the gels were washed for 2 days in DMEM medium to eliminate the initial burst before treatment, then 50 µl hydrogel with different loading were injected into a 24 well plate seeded with MDA-MB-231 cells. 450 µl culture medium were added into each well. As illustrated in FIG. 46B, after removing DOX released in the first 2 days, hydrogels loaded with 50, 100, and 150 µg/mL complexes released therapeutic levels (0.26-0.17 µg/mL, 0.36-0.14 µg/mL, 0.53-0.16 µg/mL) of DOX for 2, 7, and 9 days.

Figure 47:
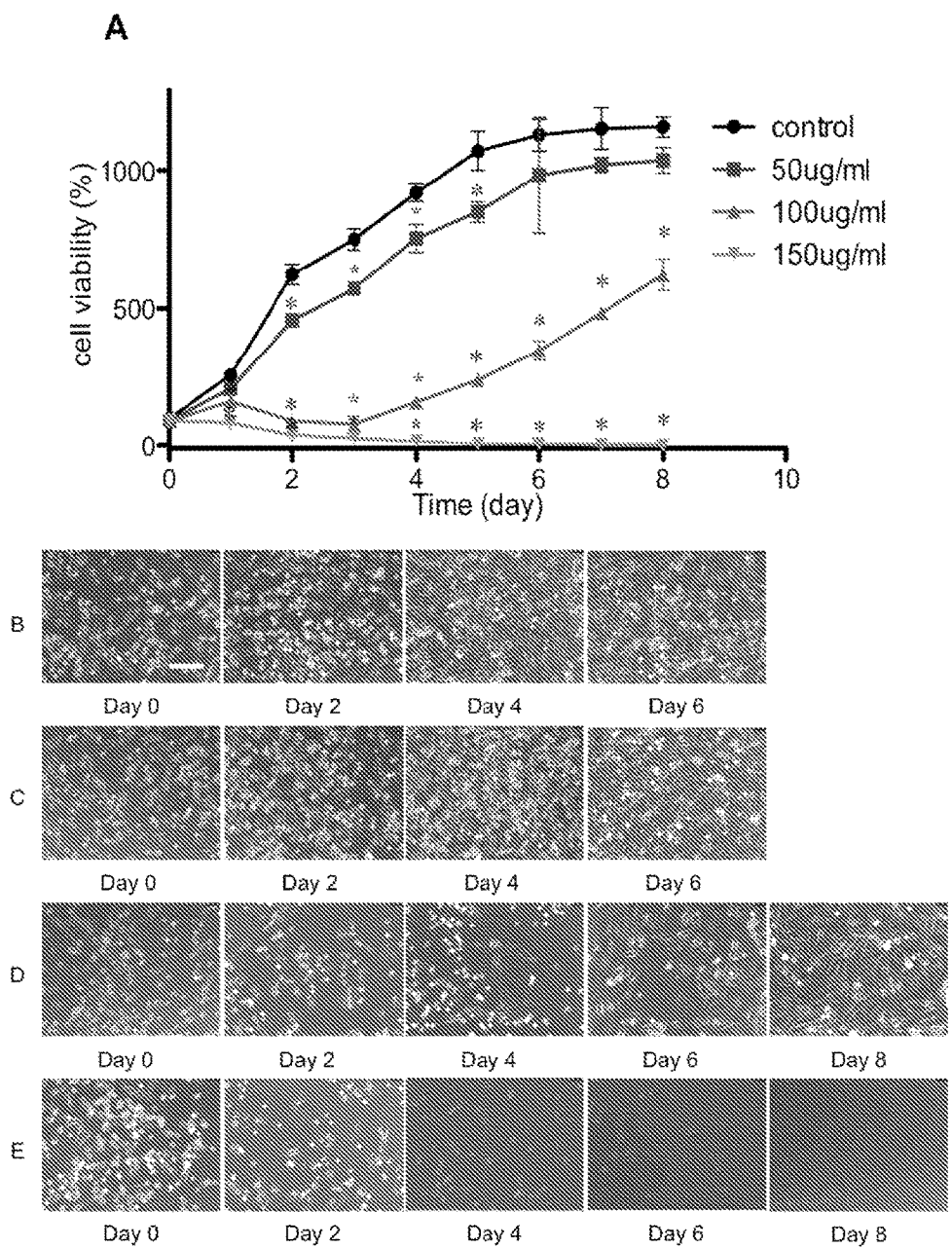
FIG. 47, comprising

Alamar blue assay (FIG. 47A) shows that the number of untreated MDA-MB-231 cells kept increasing with time and the cells reached confluence in 4 days (FIG. 47B), indicating that they were actively proliferating. Cells treated with hydrogel loaded with 50 µg/mL complex showed similar pattern although the cell number was slightly reduced compared with untreated control (FIGS. 47A and 47C). When treated with hydrogel loaded 100 µg/mL complex, the number of MDA-MB-231 cells initially decreased with time in the first 3 days, then it started to increase and the cells became confluent in 8 days (FIGS. 47A and 47D). This result indicates that at the loading of 100 µg/mL the dose and duration of DOX release was not sufficient to inhibit cancer cell proliferation. At the loading of 150 µg/mL, the number of cancer cells decreased with time and reached 0 at day 7 (FIG. 47A). Microscopic images confirmed that all MDA-MB-231 was killed in 8 days (FIG. 47E). At this loading the concentrations of DOX released during day 3 to 9 (corresponding to 7 days of DOX treatment for cancer cells) were above 0.2 µg/mL except for day 7 (0.16 µg/mL) (FIG. 47B), and at the dose of 0.2 µg/mL all the cancer cells were completely killed in 8 days (FIG. 47A). These results help explain the finding that the released DOX killed all the cancer cells in 7 to 8 days.

Safety of Complex-Loaded Hydrogel

Figure 48:
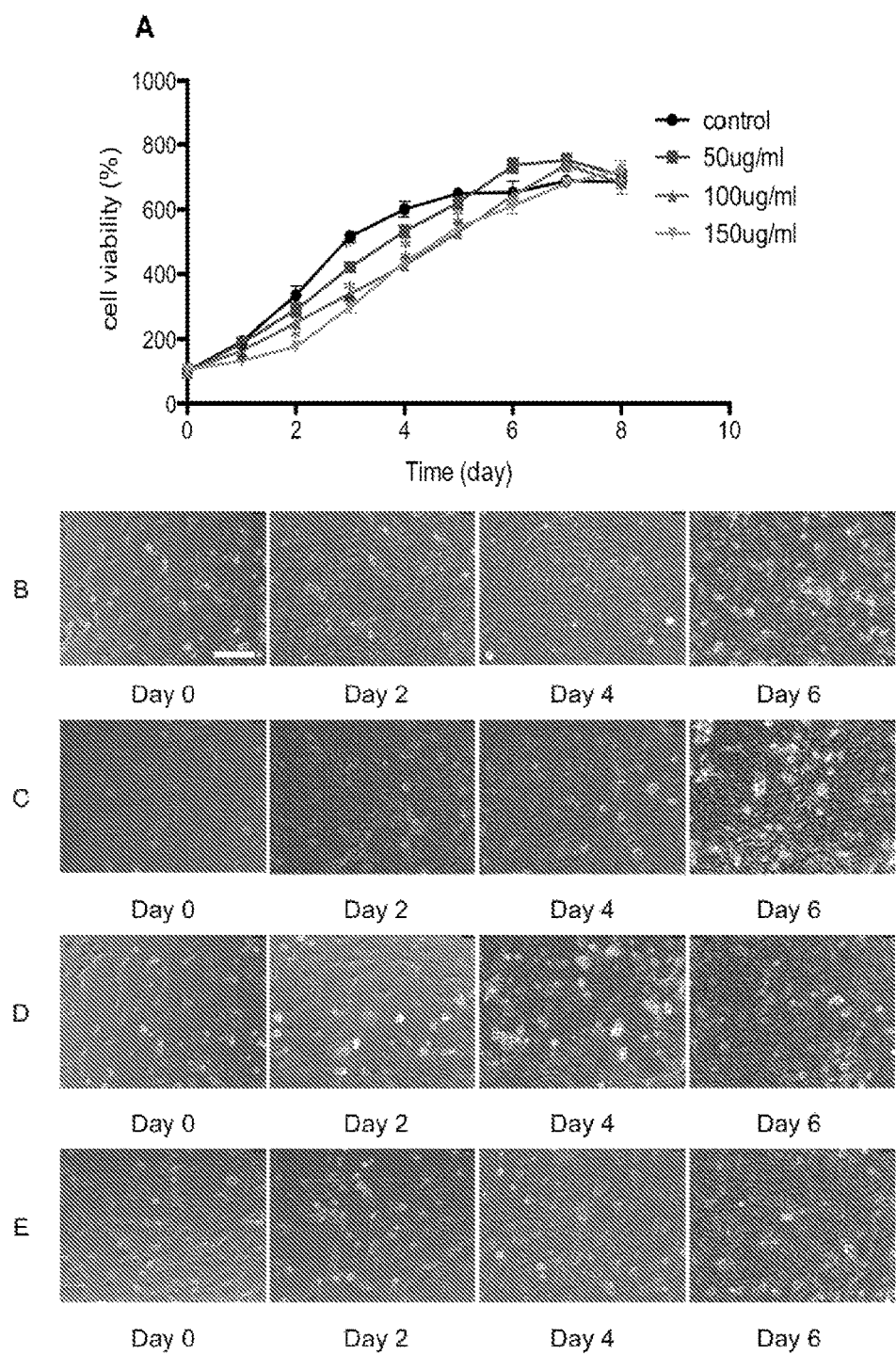
FIG. 48, comprising

FIG. 48A illustrates that at the loading of 50 µg/mL the viability of NIH 3T3 cells was not significantly different from that of untreated control except on day 3, indicating that this DOX loading has minimum toxicity to fibroblasts. Increasing the loading to 100 and 150 µg/mL significantly reduced cell viability compared with control in the first 5 days, after that the cell viability in both groups was not significantly different from control. Microscopic images conformed this result (FIGS. 48B-48E). Moreover, the morphology of hydrogel-treated NIH 3T3 cell was comparable to that of untreated control. These results revealed that the DOX released from all three loadings did not have long term toxic effect. FIG. 48B illustrates that for these two loadings (100 and 150 µg/mL) DOX released after 5-day treatment was close to 0.2 µg/mL and reduced with time. Nine-day treatment with 0.2 µg/mL DOX did not significantly reduce the cell viability of fibroblasts compared with untreated control. This helps explain the finding that after 5-day treatment the released DOX stopped showing cytotoxicity. Collectively, in certain embodiments 150 µg/mL may be the optimum loading because it caused complete kill of cancer cells in 7-8 days, while did not show long term cytotoxicity for NIH 3T3 fibroblasts.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A composition comprising a therapeutic agent or a salt thereof, a polyelectrolyte, and a polyvalent metal ion,
   wherein the polyvalent metal ion is selected from the group consisting of $Ca^{2+}$ and $Mg^{2+}$;
   wherein the therapeutic agent is minocycline, or a salt or solvate thereof;
   wherein the therapeutic agent chelates at least a fraction of the polyvalent metal ion to form a chelate adduct;
   wherein the polyvalent metal ion-therapeutic agent chelate adduct crosslinks at least a portion of the polyelectrolyte;
   wherein the composition is capable of sustained release of the therapeutic agent over a period of at least 24 days; and
   wherein the polyelectrolyte comprises dextran sulfate.

2. The composition of claim 1, wherein the composition further comprises a polycation selected from the group consisting of chitosan and gelatin type A (GA).

3. A particle comprising the composition comprising a therapeutic agent or a salt thereof, a polyelectrolyte, and a polyvalent metal ion; wherein the polyvalent metal ion is selected from the group consisting of $Ca^{2+}$ and $Mg^{2+}$; wherein the therapeutic agent is minocycline, or a salt or solvate thereof; wherein the therapeutic agent chelates at least a fraction of the polyvalent metal ion to form a chelate adduct; wherein the polyvalent metal ion-therapeutic agent chelate adduct crosslinks at least a portion of the polyelectrolyte; wherein the composition is capable of sustained release of the therapeutic agent over a period of at least 24 days; and wherein the polyelectrolyte comprises dextran sulfate, wherein the particle comprises a nanoparticle.

4. A biocompatible hydrogel comprising at least one selected from the group consisting of the composition of claim 1 and the particle of claim 3.

5. The hydrogel of claim 4, further comprising agarose, alginate, alginate sulfate, dextran sulfate, hyaluronan, chitosan, collagen, pectin, carrageenan, gelatin, or any combinations thereof.

6. A biocompatible layer-by-layer (LbL) assembly comprising two or more overlaid multilayer units, wherein each multilayer unit independently comprises a composition comprising a therapeutic agent or a salt thereof, a polyelectrolyte, a polyvalent metal ion, and optionally a polycation;

wherein the polyvalent metal ion is selected from the group consisting of $Ca^{2+}$ and $Mg^{2+}$, wherein the therapeutic agent is minocycline, or a salt or solvate thereof;

wherein the therapeutic agent chelates at least a fraction of the polyvalent metal ion to form a chelate adduct;

wherein the polyvalent metal ion-therapeutic agent chelate adduct crosslinks at least a portion of the polyelectrolyte;

wherein the composition is capable of sustained release of the therapeutic agent over a period of at least 24 days; and wherein the polyelectrolyte comprises dextran sulfate.

7. The LbL assembly of claim 6, wherein each multilayer unit is independently a bilayer or trilayer unit.

8. The LbL assembly of claim 6, wherein the thickness of the two or more overlaid multilayer units is equal to or less than about 10 µm.

9. A method of treating or ameliorating a disease or disorder in a subject in need thereof, the method comprising administering to the subject a therapeutically effective amount of at least one biocompatible composition selected from the group consisting of:

(a) a particle comprising a composition comprising a therapeutic agent or a salt thereof, a polyelectrolyte, and a polyvalent metal ion; wherein the polyvalent metal ion is selected from the group consisting of $Ca^{2+}$ and $Mg^{2+}$; wherein the therapeutic agent is minocycline, or a salt or solvate thereof; wherein the therapeutic agent chelates at least a fraction of the polyvalent metal ion to form a chelate adduct; wherein the polyvalent metal ion-therapeutic agent chelate adduct crosslinks at least a portion of the polyelectrolyte; wherein the composition is capable of sustained release of the therapeutic agent over a period of at least 24 days; and wherein the polyelectrolyte comprises dextran sulfate;

(b) a hydrogel comprising a composition comprising a therapeutic agent or a salt thereof, a polyelectrolyte, and a polyvalent metal ion; wherein the polyvalent metal ion is selected from the group consisting of $Ca^{2+}$ and $Mg^{2+}$; wherein the therapeutic agent is minocycline, or a salt or solvate thereof; wherein the therapeutic agent chelates at least a fraction of the polyvalent metal ion to form a chelate adduct; wherein the polyvalent metal ion-therapeutic agent chelate adduct crosslinks at least a portion of the polyelectrolyte; wherein the composition is capable of sustained release of the therapeutic agent over a period of at least 24 days; and wherein the polyelectrolyte comprises dextran sulfate; and, (c) a layer-by-layer (LbL) assembly comprising a composition comprising a therapeutic agent or a salt thereof, a polyelectrolyte, and a polyvalent metal ion; wherein the polyvalent metal ion is selected from the group consisting of $Ca^{2+}$ and $Mg^{2+}$; wherein the therapeutic agent is minocycline, or a salt or solvate thereof; wherein the therapeutic agent chelates at least a fraction of the polyvalent metal ion to form a chelate adduct; wherein the polyvalent metal ion-therapeutic agent chelate adduct crosslinks at least a portion of the polyelectrolyte; wherein the composition is capable of sustained release of the therapeutic agent over a period of at least 24 days; and wherein the polyelectrolyte comprises dextran sulfate;

wherein the biocompatible composition is essentially free of a polycation or further comprises a polycation.

10. The method of claim 9, wherein the at least one biocompatible composition is inserted, implanted or injected in the subject.

11. The method of claim 10, wherein the at least one biocompatible composition is fluid at the temperature used for insertion, implantation or injection, and is a gel at the subject's body temperature.

12. The method of claim 9, wherein the disease or disorder is selected from the group consisting of chronic inflammation, auto-immune disease, spinal cord injury, stroke, myocardial infarction, chronic heart failure, diabetes, circulatory shock, chronic inflammatory disease, cancer, neurodegenerative disorder, traumatic brain injury, severing of a peripheral nerve, nerve root impingement, traumatic injury, and any combinations thereof.

13. A technological device, wherein the device is used for insertion, implantation or injection into a subject, wherein at least a portion of the surface of the device to be inserted, implanted or injected into the subject is coated with a layer-by-layer (LbL) assembly comprising a composition comprising a therapeutic agent or a salt thereof, a polyelectrolyte, and a polyvalent metal ion; wherein the polyvalent metal ion is selected from the group consisting of $Ca^{2+}$ and $Mg^{2+}$; wherein the therapeutic agent is minocycline, or a salt or solvate thereof; wherein the therapeutic agent chelates at least a fraction of the polyvalent metal ion to form a chelate adduct; wherein the polyvalent metal ion-therapeutic agent chelate adduct crosslinks at least a portion of the polyelectrolyte; wherein the composition is capable of sustained release of the therapeutic agent over a period of at least 24 days; wherein the polyelectrolyte comprises dextran sulfate and wherein the composition is essentially free of a polycation or further comprises a polycation.

14. The device of claim 13, wherein the device is selected from the group consisting of a medical implant, cosmetic implant, vascular implant, auditory implant, cochlear implants, orthopedic implant, bone plate, screw, joint prosthetic, breast implant, artificial larynx implant, maxillofacial prosthetic, dental implant, pacemaker, cardiac defibrillator, penile implant, drug pump, drug delivery device, sensors, monitor, neurostimulator, incontinence alleviating device, intraocular lens, water transporting sack, electrolyte transporting sack, glucose transporting sack, oxygen transporting sack, cells replacing a lost or damaged function of the human body, tissues replacing a lost or damaged function of the human body, neural prosthetic, recording electrode, cochlear implant, and any combinations thereof.

15. A method of derivatizing a technological device, wherein the device is used for insertion, implantation or injection into a subject, wherein the method comprises coating at least a portion of the surface of the device to be inserted, implanted or injected into the subject with a layer-by-layer (LbL) assembly comprising a composition comprising a therapeutic agent or a salt thereof, a polyelectrolyte, and a polyvalent metal ion; wherein the polyvalent metal ion is selected from the group consisting of $Ca^{2+}$ and $Mg^{2+}$; wherein the therapeutic agent is minocycline, or a salt or solvate thereof; wherein the therapeutic agent chelates at least a fraction of the polyvalent metal ion to form a chelate adduct wherein the polyvalent metal ion-therapeutic agent chelate adduct crosslinks at least a portion of the polyelectrolyte; wherein the composition is capable of sustained release of the therapeutic agent over a period of at least 24 days; wherein the polyelectrolyte comprises dextran sulfate, and wherein the composition is essentially free of a polycation or further comprises a polycation.

* * * * *